United States Patent [19]
Vlasuk et al.

[11] Patent Number: 5,864,009
[45] Date of Patent: Jan. 26, 1999

[54] NEMATODE-EXTRACTED ANTICOAGULANT PROTEIN

[75] Inventors: George Phillip Vlasuk, Carlsbad, Calif.; Patrick Eric Hugo Stanssens, St-Martens-Latem, Belgium; Joris Hilda Lieven Messens, Antwerp, Belgium; Marc Jozef Lauwereys, Haaltert, Belgium; Yves René Laroche, Brussels, Belgium; Laurent Stéphane Jespers, Tervuren, Belgium; Yannick Georges Jozef Gansemans, Bredene, Belgium

[73] Assignee: Corvas International, Inc., San Diego, Calif.

[21] Appl. No.: 480,478

[22] Filed: Jun. 6, 1995

Related U.S. Application Data

[63] Continuation of Ser. No. 326,110, Oct. 18, 1994.

[51] Int. Cl.$^6$ ............................ C07K 14/81; C12P 21/02
[52] U.S. Cl. ........................ 530/324; 530/350; 435/69.2
[58] Field of Search .................................. 530/350, 324; 435/69.2

[56] References Cited

U.S. PATENT DOCUMENTS

| | | | |
|---|---|---|---|
| 4,458,066 | 7/1984 | Caruthers, et al. | 536/27 |
| 4,683,293 | 7/1987 | Craig | 530/359 |
| 4,745,051 | 5/1988 | Smith et al. | 435/68 |
| 4,777,242 | 10/1988 | Nelles | 530/351 |
| 4,808,537 | 2/1989 | Stroman et al. | 435/6 |
| 4,812,405 | 3/1989 | Lair et al. | 435/255 |
| 4,818,700 | 4/1989 | Cregg et al. | 435/252.33 |
| 4,837,148 | 6/1989 | Cregg | 435/172.3 |
| 4,855,231 | 8/1989 | Stroman et al. | 435/68 |
| 4,857,467 | 8/1989 | Sreekrishna et al. | 435/255 |
| 4,879,231 | 11/1989 | Stroman et al. | 435/172.3 |
| 4,882,279 | 11/1989 | Cregg | 435/172.3 |
| 4,885,242 | 12/1989 | Cregg | 435/68 |
| 4,895,800 | 1/1990 | Tschopp et al. | 435/69.3 |
| 5,002,876 | 3/1991 | Sreekrishma et al. | 435/69.5 |
| 5,004,688 | 4/1991 | Craig et al. | 435/69.3 |
| 5,023,236 | 6/1991 | Edgington et al. | 514/18 |
| 5,032,516 | 7/1991 | Cregg | 435/172.3 |
| 5,106,833 | 4/1992 | Broze et al. | 514/12 |
| 5,122,465 | 6/1992 | Cregg et al. | 435/172.3 |
| 5,135,868 | 8/1992 | Cregg | 435/255 |
| 5,166,329 | 11/1992 | Cregg | 536/27 |
| 5,189,019 | 2/1993 | Palladino et al. | 514/12 |
| 5,204,261 | 4/1993 | Prevatt et al. | 435/255 |
| 5,239,058 | 8/1993 | Vlasuk et al. | 530/524 |
| 5,239,059 | 8/1993 | Zasloff et al. | 530/325 |
| 5,268,273 | 12/1993 | Buckholz | 435/69.1 |
| 5,330,901 | 7/1994 | Prevatt et al.. | 435/69.6 |
| 5,427,937 | 6/1995 | Cappello et al. | 435/212 |
| 5,525,477 | 6/1996 | Hassouna | 435/13 |
| 5,601,571 | 2/1997 | Lyle et al. | 424/1.41 |
| 5,605,671 | 2/1997 | Lyle et al. | 424/1.41 |

FOREIGN PATENT DOCUMENTS

| | | |
|---|---|---|
| 0255771 | 2/1988 | European Pat. Off. . |
| 0419099 | 3/1991 | European Pat. Off. . |
| 0439442 | 7/1991 | European Pat. Off. . |
| 0454372 | 10/1991 | European Pat. Off. . |
| 88/09811 | 12/1988 | WIPO . |
| 91/02753 | 3/1991 | WIPO . |
| 94/25000 | 11/1994 | WIPO . |
| 95/12615 | 5/1995 | WIPO . |
| 96/04378 | 2/1996 | WIPO . |
| 96/12021 | 4/1996 | WIPO . |
| 96/04377 | 2/1997 | WIPO . |

OTHER PUBLICATIONS

Aoki, Y., et al., "Effects of Recombinant Human Soluble Thrombomodulin (rhs–TM) on a Rat Model of Disseminated Intravascular Coagulation with Decreased Levels of Plasma Antithrombin" *Thrombosis and Hemostasis* 71(4):452–455 (1994).

Babin et al., "The Isoinhibitors of Chymotrypsin/Elastase from Ascaris lumbricoides: The Primary Structure" *Arch. of Biochem. and Biophy.* 232(1):143–161 (1984).

Beaucage et al., "Deoxynucleoside Phosphoramidites–A New Class of Key Intermediates for Deoxypolynucleotide Synthesis" *Tetrahedron Letters*, 22(20):1859–1862 (1981).

Bernard, et al., "The Serine Protease Inhibitor Family from Ascaris Suum: Chemical Determination of the Five Disulfide Bridges" *Arch. Biochem. Biophys.*, 303(2):367–376 (1993).

Bock, P.E. et al. "Isolation of Human Coagulation a–Factor $X_a$ by Soybean Trypsin Inhibitor–Sepharose Chromatography and Its Active–Site Titration with Fluorescein Mono–p–guanidinobenzoate" *Archives of Biochem. Biophys.* 273(2):375–388 (1989).

Bolivar et al., "Construction and Characterization of New Cloning Vehicles" *Gene*, 2:95–113 (1977).

Broach, J. et al., "Transformation In Yeast:Development of a Hybrid Cloning Vector and Isolation of the CAN1 Gene" *Gene*, 8:121–133 (1978).

Brown, E. et al., "Chemical Synthesis and Cloning of a Tyrosine tRNA Gene" *Methods in Enzymology*, 68, 109–151 (1979).

Bullock et al., "XL1–Blue:A High Efficiency Plasmid Transforming recA *Escherichia coli* Strain with Beta–Galactosidase Selection" *Biotechniques* 5(4):376–379 (1987).

Cairns et al., "Antithrombotic Agents in Coronary Artery Disease" *Chest* 102:456S–481S (1992).

Crameri et al., "Display of Biologically Active Proteins on the Surface of Filamentous Phages: a cDNA Cloning System for Selection of Functional Gene Products Linked to the Genetic Information Responsible for their Production" *Gene*, 137:69–75 (1993).

(List continued on next page.)

*Primary Examiner*—Kawai Lau
*Attorney, Agent, or Firm*—Lyon & Lyon LLP

[57] ABSTRACT

Proteins which are potent anticoagulants and have at least one NAP domain and are described. These proteins having anticoagulant activity can be isolated from natural sources such as nematodes, chemically synthesized or made by recombinant methods using various DNA expression systems.

37 Claims, 28 Drawing Sheets

OTHER PUBLICATIONS

Cappello et al., "Ancylostoma Factor Xa Inhibitor: Partial Purification and Its Identification as a Major Hookworm–Derived Anticoagulant In Vitro" *J. Infect. Diseases*, 167:1474–1477 (1993).

Cappello et al., "Ancylostoma caninum anticoagulant peptide: A hookworm–derived Inhibitor of Human Coagulation Factor Xa," *Proc. Natl. Acad Sci. U.S.A.* 92:6152–6156 (1995).

Carroll et al., "The Anticoagulant Effects of the Hookworm, Ancylostoma Ceylanicum: Observations on Human and Dog Blood In Vitro and Infected Dogs In Vivo" *Thromb. Haemostas.* (Stuttgart), 51(2):222–227 (1984).

Carson, "Computerized Analysis of Enzyme Cascade Reactions Using Continuous Rate Data Obtained with an ELISA Reader" *Comput. Prog. Biomed* 19:151–157 (1985).

Clements et al., "Secretion of Human Epidermal Growth Factor from Saccharomyces Cerevisiae Using Synthetic Leader Sequences" *Gene* 106:267–272 (1991).

Cohen, Nonchromosomal Antibiotic Resistance in Bacteria: Genetic Transformation of *Escherichia coli* by R–Factor DNA *Proc. Natl. Acad. Sci. USA*, 69(8):2110–2114 (1972).

Crawford, et al., "Inhibition of Human Blood Clotting By Extracts of Ascaris Suum" *J. Parasitol.*, 68(6):1044–1047 (1982).

Curtis, *Biology Fourth ed.* N.Y. Worth Publishers, Inc. pp. 500–501 (1983).

Depicker et al., "Nopaline Synthase: Transcript Mapping and DNA Sequence" *J. Mol. Appl. Gen.*, 1(6):561–573 (1978).

Despreaux et al., "The dac A Gene of Bacillus Stearothermophilus Coding for D–Alanine Carboxypeptidase: Cloning, Structure and Expression in *Escherichia Coli* and *Pichia Pastoris*" *Gene* 131:35–41 (1993).

Fiers, et al., "Complete Nucleotide Sequence of SV40 DNA" *Nature*, 273:113–120 (1978).

Fuster, V. The Pathogenesis of Coronary Artery Disease and the Acute Coronary Syndromes *New Engl. J. Med.* 326(5):310–318 (1992).

Glaser–Wuttke, G., "Pore–Forming Properties of the Adsorption protein of *Filamentous Phage fd*" *Biochem. Biophys. Acta*, 985:239–247 (1989).

Glover, "Gene Cloning: The Mechanics of DNA Manipulation" 1–20 (1984).

Goeddel et al., "Synthesis of Human Fibroblast Interferon by *E. Coli*" *Nucleic Acids Res.*, 8(18):4057–4074 (1980).

Gold et al., "Evidence for a Rebound Coagulation Phenomenon After Cessation of a 4–hour Infusion of a Specific Thrombin Inhibitor in Patients with Unstable Angina Pectoris" *JACC* 21(5):1039–1047 (1993).

Grasberger et al., "High–Resolution Structure of Ascaris Trypsin Inhibitor in Solution: Direct Evidence for a pH–induced Conformational Transition in the Reactive Site" *Structure*, 2:669–678 (1994).

Hemker et al., "Feedback Mechanisms in Coagulation" *Hemostasis* 21:189–196 (1991).

Hirsh, J., "Heparin" *N.Engl.J.Med* 324(22):1565–1574 (1992).

Hitzeman et al., "Isolation and Characterization of the Yeast 3–Phosphoglycerokinase Gene (PGK) by an Immunological Screening Technique" *J. Biol. Chem.*, 255(24):12073–12080 (1980).

Holland et al., "The Primary Structures of Two Yeast Enolase Genes" *J. Biol. Chem.*, 256(3):1385–1395 (1981).

Houghten, "General Method for the Rapid Solid–Phase Synthesis of Large Numbers of Peptides: Specificity of Antigen–Antibody Interaction at the level of Individual Amino Acids" *Proc. Natl. Acad. Sci.*, 82:5131–5135 (1985).

Hsiao, C.L. et al.,. "High–Frequency Transformation of Yeast by Plasmids Containing the Cloned Yeast ARG4 Gene" *Proc. Natl. Acad. Sci. USA* 76(8):3829–3833 (1979).

Huang et al., "The Molecular Structure of the Complex of the Complex of Ascaris Chymotrypsin/Elastase Inhibitor with Porcine Elastase" *Structure* 2:679–689 (1994).

Itakura et al., "Expression in *Escherichia Coli* of a Chemically Synthesized Gene for the Hormone Somatostatin" *Science* 198:1056–1063 (1977).

Kasten, B.L., "Specimen Collection", *Laboratory Test Handbook*, 2nd Edition, Lexi–Comp Inc., Cleveland pp. 16–17 (Edits. Jacobs, D.S. et al. 1990).

Kessler, C. "The Pharmacology of Aspirin, Heparin, Coumarin and Thrombolytic Agents" *Chest* 99:97S–112S (1991).

Kurz, K.D., et al., "Rat Model of Arterial Thrombosis Induced by Ferric Chloride" *Thromb. Res.* 60:269–280 (1990).

Lawson et al., "A Model for the Tissue Factor Pathway to Thrombin" *J. Biol. Chem.* 269(37):23357–23366 (1994).

Levine et al., "Hemorrhagic Complications of Anticoagulant Treatment" *Chest* 102:352S–363S (1992).

Lidon et al., "Initial Experience with Direct Antithrombin Hirulog, in Unstable Angina" *Circulation* 88(4):1495–1501 (1993).

Loeb et al., "The Presence of a Substance Inhibiting the Coagulation of the Blood in Ancylostoma" *Proc. Pathol. Soc. of Philadelphia*, 7(6):173–178 (1904).

Lucchesi et al., "Prevention of Thrombosis and Rethrombosis and Enhancement of the Thrombolytic Actions of Recombinant Tissue–Type Plasminogen Activator in the Canine Heart by DMP728, A Glycoprotein Iib/IIIa Antagonist" *Brit. J. Pharmacol.* 113:1333–1343 (1994).

Maniatis et al., "Molecular Cloning: A Laboratory Manual" *Cold Spring Harbor Press* pp. 254–255 (1982).

Mann et al., "Surface–Dependant Hemostasis" *Sem. Hematology* 29(3):213–226 (1992).

Mann et al., Blood 76(1):1–16 (1990).

Merrifield, "Solid Phase Peptide Synthesis. I. The Synthesis of a Tetrapeptide" *J. Amer. Chem. Soc.* 85:2149–2154 (1963).

Messing et al., "A System for Shotgun DNA Sequencing" *Nucleic Acids Res.* 9(2):309–321 (1981).

*Methods of Enzymology*, 65:499–560 (1980).

Mizushima et al., "pEF–BOS, A Powerful Mammalian Expression Vector" *Nucl. Acids Res.*, 18(17):5322 (1990).

Morrison et al., "The Behavior and Significance of Slow––Binding Enzyme Inhibitors" *C.T. Adv. Enzymol.* 61:201–301 (1988).

Maruyama et al., "Lambda foo:a λ phage vector for the expression of foreign proteins" *Proc. Nat'l. Acad. Sci., USA* 91:8273–8277 (1994).

Narang et al., "Improved Phosphotriester Method for the Synthesis of Gene Fragments" *Methods in Enzymol* 68:90–109 (1979).

Nawa et al., "The Glycosaminoglycan of Recombinant Human Soluble Thrombomodulin Affects Antithrombotic Activity in a Rat Model of Tissue Factor–Induced Disseminated Intravascular Coagulation" *Thrombosis and Hemostasis* 67(3):366–370 (1992).

Nutt et al., "The Amino Acid Sequence of Antistasin" *J. Biol. Chem*, 263(21):10162–10167 (1988).

Oklahoma Medical Research Foundation, "Thrombin–binding polypeptides as antithrombotic agent for artificial organs or other surfaces" *Chemical Abstracts* 113:18 abstract No. 158738 (1990).

"Principles and Applications for DNA Amplification" *PCR Technology* (1989) New York:Stockton Press (complete volume).

Pritchard D., "The Anti–haemostatic Strategies of the Human Hookworm Necator Americanus" *Thromb. Haemost.* 73(3):546 (1995).

"The Source for Discovery" *Protocols and Applications Guide 3rd ed.* Promega Corp. USA (1996) (complete volume).

Rappaport, S., "Initiation and Regulation of Tissue Factor–Dependent Blood Coagulation" *Arteriosclerosis and Thrombosis* 12(10):1111–1121 (1992).

Roberts et al., "Directed Evolution of a Potent Neutrophil Elastase Inhibitors Displayed on M13 Fusion Phage " *Proc. Nat'l Acad. Sci., USA* 89:2429–2433 (1992).

Ruf et al., "Mutational Analysis of Receptor and Cofactor Function of Tissue Factor" *Methods in Enzymol.* 222, 209–224 (1993).

Salvensen et al., "Proteinase Inhibitors: a–Macroglobulins, Serpins and Kunins", *Hemostasis and Thrombosis Third ed.* 251–253 (1994) J.B. Lippincott Comp.

Sambrook et al., "Molecular Cloning, A Laboratory Manual", Second Edition, vol. 1 to 3, *Cold Spring Harbor Laboratory Press* (1989) pp. xi–xxxviii.

Sanger et al., "DNA Sequencing with Chain–Terminating Inhibitors" *Proc. Natl. Acad. Sci. USA*, 74(12):5463–5467 (1977).

Sharma et al., "Usefulness and Tolerability of Hirulog, a Direct Thrombin–Inhibitor, in Unstable Angina Pectoris" *Am. J. of Cardiol.* 72:1357–1360 (1993).

Shaw et al., "A General Method for the Transfer of Cloned Genes to Plant Cells" *Gene*, 23:15–330 (1983).

Shimatake et al., "Purified λ Regulatory Protein cII Positively Activates Promoters for Lysogenic Development" *Nature*, 292:128–132 (1981).

Shulman et al., "Platelet Dynamics" *Hemostasis and Thrombosis: Basic Principles and Clinical Practice* 251–253 (1982) J.B. Lipoincott Comp., Philadelphia Sikela et al., "Screening an Expression Library with a Ligand Probe: Isolation and Sequence of a cDNA Corresponding to a Brain Calmodulin–Binding Protein" *Proc. Nat'l. Acad. Sci.*, USA 84:3038–3042 (1987).

Smith et al., "Libraries of Peptides and Proteins Displays on Filamentous Phage" *Methods of Enzomol.* 217, 228–257 (1993).

Soumillion et al., "Selection of β–lactamase on Filamentous Bacteriophage by Catalytic Activity" *J. Mol. Biol.* 237:415–422 (1994).

Spellman et al., "Antiocoagulant Activity of Dog Hookworm" *Am. J. Physiol.* 220(4):922–927 (1971).

Stanssens et al., "Anticoagulant Repertoire of the Hookworm Ancylostoma Caninum" *Proc. Natl. Acad. Sci. U.S.A.* 93:2149–2154 (1996).

Taylor, "Identification of Protein Sequence Homology by Consensus Templae Alignment" *J. Mol. Biol.* 188:233–258 (1986).

Tuszynski et al., "Isolation and Characterization of Antistatin" *J. Biol. Chem*, 262(20):9718–9723 (1987).

Van Solingen et al., "Fusion of Yeast Spheroplasts" *J. Bacter.* 130:946–947 (1977).

Van Lenten et al., "Studies on the Chemical and Enzymatic Modification of Glycoproteins" *J. of Biol. Chem.* 246(6):1889–1894 (1971).

Vieira et al., "Production of Single–Stranded Plasmid DNA" *Methods in Enzymol.* 153, 3–11 (1987).

Vlasuk, et al., "Structural and Functional Characterization of Tick Anticoagulant Peptide (TAP): A Potent and Selective Inhibitor of Blood Coagulation Factor Xa" *Thromb. Haemostas.* 70(1):212–216 (1993).

Vrijsen et al., "Resolution of the Major Poliovirus Polypeptides into Doublets" *Virology*, 86:546–555 (1978).

Waxman et al., "Tick Anticoagulant Peptide (TAP) Is a Novel Inhibitor of Blood Coagulation Factor Xa" *Science* 248:593–596 (1990).

Weitz et al., "New Anticoagulant Strategies" *J. Lab. Clin. Med.* 22(4):364–373 (1993).

Zell et al., "DNA Mismatch–Repair in *Escherichia Coli* Counteracting the Hydrolytic Deamination of 5–Mehtyl–Cytosine Residues" *Embo J.*, 6(6):1809–1815 (1987).

Hotez and Pritchard, "Hookworm Infection", *Sci. Am.*, Jun. 1995, pp. 68–74.

Cappello et al., "Ancylostoma caninum anticoagulant peptide: cloning by PCR and expression of soluble, active protein in *E. coli* ", *Molec. Biochem. Parasitol.* 80:113–117 (1996).

Jespers et al., "Surface Expression and Ligand–Based Selection of cDNAs Fused to Fileamentous Phage Gene VI", *Bio/Technoogy* 13:378–382 (1995).

Jock Friedly, "New Anticoagulant Prompt Bad Blood Between Partners", *Science* 271:1800–1801 (1996).

May 10, 1996 letter from David Kabakoff to *Science* ; not published.

May 13, 1996 fax from Yale Univesity to Corvas including letter (5/10/96) said to have been sent to *Science* ; not published Jul. 16, 1996 e–mail from Science to Jean Ellis noting receipt of 5/10/96 Kabakoff letter.

Sep. 17, 1996 e–mail from *Science* to Jean Ellis noting Science decision to not publish 5/10/96 Kabakoff letter.

Sep. 26, 1996 letter from Randall Woods to *Science* ; not published.

Apr. 21, 1995 letter from George Vlasuk to *Thrombosis and Haemostasis* ; not published.

Cappello, M. et al. (1993) "Ancylostoma factor Xa inhibitor: partial purification and its identification as a major hookworm–derived anticoagulant in vitro" J. Inf. Dis. 167:1474–1477, Jun. 1993.

Curtis, H. (1983) Biology, Fourth Edition. New York: Worth Publishers, Inc., pp. 500–501, 1983.

Fig. 1

```
          1            10              20             30
          *            *               *              *
G AATTCCGCTA CTACTCAACA ATG AAG ATG CTT TAC GCT ATC GCT
                       Met Lys Met Leu Tyr Ala Ile Ala 40            50              60             70
      *             *               *              *
ATA ATG TTT CTC CTG GTA TCA TTA TGC AGC GCA AGA ACA GTG
Ile Met Phe Leu Leu Val Ser Leu Cys Ser Ala Arg Thr Val 80            90             100            110           120
  *             *               *              *             *
AGG AAG GCA TAC CCG GAG TGT GGT GAG AAT GAA TGG CTC GAC
Arg Lys Ala Tyr Pro Glu Cys Gly Glu Asn Glu Trp Leu Asp 130            140            150            160
            *              *              *              *
GAC TGT GGA ACT CAG AAG CCA TGC GAG GCC AAG TGC AAT GAG
Asp Cys Gly Thr Gln Lys Pro Cys Glu Ala Lys Cys Asn Glu 170            180            190            200
         *              *              *              *
GAA CCC CCT GAG GAG GAA GAT CCG ATA TGC CGC TCA CGT GGT
Glu Pro Pro Glu Glu Glu Asp Pro Ile Cys Arg Ser Arg Gly 210            220            230            240
         *              *              *              *
TGT TTA TTA CCT CCT GCT TGC GTA TGC AAA GAC GGA TTC TAC
Cys Leu Leu Pro Pro Ala Cys Val Cys Lys Asp Gly Phe Tyr 250            260            270            280
         *              *              *              *
AGA GAC ACG GTG ATC GGC GAC TGT GTT AGG GAA GAA GAA TGC
Arg Asp Thr Val Ile Gly Asp Cys Val Arg Glu Glu Glu Cys 290            300            310            320           330
      *              *              *              *             *
GAC CAA CAT GAG ATT ATA CAT GTC TGA ACGAGAAAGC AACAATAACC
Asp Gln His Glu Ile Ile His Val 340            350            360            370           380
      *              *              *              *             *
AAAGGTTCCA ACTCTCGCTC TGCAAAATCG CTAGTTGGAT GTCTCTTTTG 390            400            410            420           430
      *              *              *              *             *
CGTCCGAATA GTTTTAGTTG ATGTTAAGTA AGAACTCCTG CTGGAGAGAA 440            450
      *              *
TAAAGCTTTC CAACTCC poly(A)
```

Fig. 2

Lys Ala Tyr Pro Glu Cys Gly Glu Asn Glu Trp Leu Asp Asp
1               5                       10

Cys Gly Thr Gln Lys Pro Cys Glu Ala Lys Cys Asn Glu Glu
15              20                      25

Pro Pro Glu Glu Glu Asp Pro Ile Cys Arg Ser Arg Gly Cys
    30              35                      40

Leu Leu Pro Pro Ala Cys Val Cys Lys Asp Gly Phe Tyr Arg
        45              50                      55

Asp Thr Val Ile Gly Asp Cys Val Arg Glu Glu Cys Asp
            60              65                  70

Gln His Glu Ile Ile His Val
            75

Fig. 3

```
          1           10              20              30
          *           *               *               *
G AATTCCGCTA CTACTCAACA ATG AAG ATG CTT TAC GCT ATC GCT
                       Met Lys Met Leu Tyr Ala Ile Ala 40              50              60              70
  *               *               *               *
ATA ATG TTT CTC CTG GTG TCA TTA TGC AGC ACA AGA ACA GTG
Ile Met Phe Leu Leu Val Ser Leu Cys Ser Thr Arg Thr Val 80              90             100             110             120
  *               *               *               *               *
AGG AAG GCA TAC CCG GAG TGT GGT GAG AAT GAA TGG CTC GAC
Arg Lys Ala Tyr Pro Glu Cys Gly Glu Asn Glu Trp Leu Asp 130             140             150             160
              *               *               *               *
GTC TGT GGA ACT AAG AAG CCA TGC GAG GCC AAG TGC AGT GAG
Val Cys Gly Thr Lys Lys Pro Cys Glu Ala Lys Cys Ser Glu 170             180             190             200
           *               *               *               *
GAA GAG GAG GAA GAT CCG ATA TGC CGA TCA TTT TCT TGT CCG
Glu Glu Glu Glu Asp Pro Ile Cys Arg Ser Phe Ser Cys Pro 210             220             230             240
           *               *               *               *
GGT CCC GCT GCT TGC GTA TGC GAA GAC GGA TTC TAC AGA GAC
Gly Pro Ala Ala Cys Val Cys Glu Asp Gly Phe Tyr Arg Asp 250             260             270             280
       *               *               *               *
ACG GTG ATC GGC GAC TGT GTT AAG GAA GAA GAA TGC GAC CAA
Thr Val Ile Gly Asp Cys Val Lys Glu Glu Glu Cys Asp Gln 290             300             310             320             330
   *               *               *               *               *
CAT GAG ATT ATT CAT GTC TGA ACGAGAGAGC AGTAATAACC
His Glu Ile Ile His Val 340        350        360        370        380
              *          *          *          *          *
AAAGGTTCCA ACTTTCGCTC TACAAAATCG CTAGTTGGAT TTCTCCTTTG 390        400        410        420        430
              *          *          *          *          *
CGTGCGAATA GTTTTAGTTG ATATTAAGTA AAACCTCCTG TTGAAGAGAA

440
              *
TAAAGCTTTC CAACTTC poly(A)
```

Fig. 4

```
Lys Ala Tyr Pro Glu Cys Gly Glu Asn Glu Trp Leu Asp Val
 1               5                   10

Cys Gly Thr Lys Lys Pro Cys Glu Ala Lys Cys Ser Glu Glu
15               20                  25

Glu Glu Glu Asp Pro Ile Cys Arg Ser Phe Ser Cys Pro Gly
    30                  35                  40

Pro Ala Ala Cys Val Cys Glu Asp Gly Phe Tyr Arg Asp Thr
        45              50                      55

Val Ile Gly Asp Cys Val Lys Glu Glu Glu Cys Asp Gln His
            60              65                      70

Glu Ile Ile His Val
                 75
```

Fig. 5

```
Arg Thr Val Arg Lys Ala Tyr Pro Glu Cys Gly Glu Asn Glu
                 1               5                   10

Trp Leu Asp Asp Cys Gly Thr Gln Lys Pro Cys Glu Ala Lys
                15              20

Cys Asn Glu Glu Pro Pro Glu Glu Glu Asp Pro Ile Cys Arg
25                  30                  35

Ser Arg Gly Cys Leu Leu Pro Pro Ala Cys Val Cys Lys Asp
    40                  45                  50

Gly Phe Tyr Arg Asp Thr Val Ile Gly Asp Cys Val Arg Glu
        55                  60                      65

Glu Glu Cys Asp Gln His Glu Ile Ile His Val
            70                  75
```

Fig. 6

Arg Thr Val Arg Lys Ala Tyr Pro Glu Cys Gly Glu Asn Glu
            1                   5                      10

Trp Leu Asp Val Cys Gly Thr Lys Lys Pro Cys Glu Ala Lys
            15                      20

Cys Ser Glu Glu Glu Glu Asp Pro Ile Cys Arg Ser Phe
25              30                  35

Ser Cys Pro Gly Pro Ala Ala Cys Val Cys Glu Asp Gly Phe
    40              45                  50

Tyr Arg Asp Thr Val Ile Gly Asp Cys Val Lys Glu Glu Glu
        55              60                  65

Cys Asp Gln His Glu Ile Ile His Val
            70              75

Fig. 7A-1

```
1           10          20                  30              40
*           *           *                   *               *
GAATTCACTA  TTATCCAACA  ATG GCG GTG CTT TAT TCA GTA GCA
EcoRI                   Met Ala Val Leu Tyr Ser Val Ala 50              60              70              80
     *               *               *               *
ATA GCG TTA CTA CTG GTA TCA CAA TGC AGT GGG AAA CCG AAC
Ile Ala Leu Leu Leu Val Ser Gln Cys Ser Gly Lys Pro Asn 90              100             110             120
  *               *               *               *
AAT GTG ATG ACT AAC GCT TGT GGT CTT AAT GAA TAT TTC GCT
Asn Val Met Thr Asn Ala Cys Gly Leu Asn Glu Tyr Phe Ala 130             140             150             160             170
*               *               *               *               *
GAG TGT GGC AAT ATG AAG GAA TGC GAG CAC AGA TGC AAT GAG
Glu Cys Gly Asn Met Lys Glu Cys Glu His Arg Cys Asn Glu 180             190             200             210
         *               *               *               *
GAG GAA AAT GAG GAA AGG GAC GAG GAA AGA ATA ACG GCA TGC
Glu Glu Asn Glu Glu Arg Asp Glu Glu Arg Ile Thr Ala Cys 220             230             240             250
     *               *               *               *
CTC ATC CGT GTG TGT TTC CGT CCT GGT GCT TGC GTA TGC AAA
Leu Ile Arg Val Cys Phe Arg Pro Gly Ala Cys Val Cys Lys 260             270             280             290
     *               *               *               *
GAC GGA TTC TAT AGA AAC AGA ACA GGC AGC TGT GTG GAA GAA
Asp Gly Phe Tyr Arg Asn Arg Thr Gly Ser Cys Val Glu Glu 300             310             320             330
  *               *               *               *
GAT GAC TGC GAG TAC GAG AAT ATG GAG TTC ATT ACT TTT GCA
Asp Asp Cys Glu Tyr Glu Asn Met Glu Phe Ile Thr Phe Ala 340             350             360             370             380
*               *               *               *               *
CCA GAA GTA CCG ATA TGT GGT TCC AAC GAA AGG TAC TCC GAC
Pro Glu Val Pro Ile Cys Gly Ser Asn Glu Arg Tyr Ser Asp 390             400             410             420
         *               *               *               *
TGC GGC AAT GAC AAA CAA TGC GAG CGC AAA TGC AAC GAG GAC
Cys Gly Asn Asp Lys Gln Cys Glu Arg Lys Cys Asn Glu Asp 430             440             450             460
     *               *               *               *
GAT TAT GAG AAG GGA GAT GAG GCA TGC CGC TCA CAT GTT TGT
Asp Tyr Glu Lys Gly Asp Glu Ala Cys Arg Ser His Val Cys
```

Fig. 7A-2

```
      470              480              490              500
       *                *                *                *
GAA  CGT  CCT  GGT  GCC  TGT  GTA  TGC  GAA  GAC  GGG  TTC  TAC  AGA
Glu  Arg  Pro  Gly  Ala  Cys  Val  Cys  Glu  Asp  Gly  Phe  Tyr  Arg 510              520              530              540
       *                *                *                *
AAC  AAA  AAA  GGT  AGC  TGT  GTG  GAA  AGC  GAT  GAC  TGC  GAA  TAC
Asn  Lys  Lys  Gly  Ser  Cys  Val  Glu  Ser  Asp  Asp  Cys  Glu  Tyr 550              560              570              580              590
       *                *                *                *                *
GAT  AAT  ATG  GAT  TTC  ATC  ACT  TTT  GCA  CCA  GAA  ACC  TCA  CGA
Asp  Asn  Met  Asp  Phe  Ile  Thr  Phe  Ala  Pro  Glu  Thr  Ser  Arg 600         610         620         630         640
           *           *           *           *           *
    TAA  CCAAAGATGC  TACCTCTCGT  ACGCAACTCC  GCTGATTGAGGTTGATTC 650         660         670         680         690
         *           *           *           *           *
    ACTCCCTTGCATCTCAACATTTTTTTTGTGATGCTGTGCATCTGAGCTTAACCTG 700         710
     *           *
ATAAAGCCTATGGTG poly(A)
```

Fig. 7B

```
1          10         20         30         40
*          *          *          *          *
GAATTCCGC ATG CGG ACG CTC TAC CTC ATT TCT ATC TGG TTG
EcoRI     Met Arg Thr Leu Tyr Leu Ile Ser Ile Trp Leu 50          60         70         80
       *           *          *          *
TTC CTC ATC TCG CAA TGT AAT GGA AAA GCA TTC CCG AAA TGT
Phe Leu Ile Ser Gln Cys Asn Gly Lys Ala Phe Pro Lys Cys 90         100        110        120
    *          *          *          *
GAC GTC AAT GAA AGA TTC GAG GTG TGT GGC AAT CTG AAG GAG
Asp Val Asn Glu Arg Phe Glu Val Cys Gly Asn Leu Lys Glu 130        140        150        160
    *          *          *          *
TGC GAG CTC AAG TGC GAT GAG GAC CCT AAG ATA TGC TCT CGT
Cys Glu Leu Lys Cys Asp Glu Asp Pro Lys Ile Cys Ser Arg 170        180        190        200        210
*          *          *          *          *
GCA TGT ATT CGT CCC CCT GCT TGC GTA TGC GAT GAC GGA TTC
Ala Cys Ile Arg Pro Pro Ala Cys Val Cys Asp Asp Gly Phe 220        230        240        250
       *          *          *          *
TAC AGA GAC AAA TAT GGC TTC TGT GTT GAA GAA GAC GAA TGT
Tyr Arg Asp Lys Tyr Gly Phe Cys Val Glu Glu Asp Glu Cys 260        270        280        290
    *          *          *          *
AAC GAT ATG GAG ATT ATT ACT TTT CCA CCA GAA ACC AAA TGA
Asn Asp Met Glu Ile Ile Thr Phe Pro Pro Glu Thr Lys 300        310        320        330        340
    *          *          *          *          *
TGACCGAAGC TTCCACCTTT CTATACATAT CTTCACTGCTTGACAGGCTTCT 350        360        370        380        390        400
    *          *          *          *          *          *
CGACAATTTAGAAGTTCTGCTTGACTTTGTCTATTTGAAATTGTTCACACTAATG 410        420
         *          *
GGGGAAGTAAAGCATTTTCACGAC poly(A)
```

Fig. 7C

```
  1           10            20              30            40
  *           *             *               *             *
GAATTCCGCT ACATTTTCAA CA ATG TCG ACG CTT TAT GTT ATC
EcoRI                      Met Ser Thr Leu Tyr Val Ile 50            60            70            80
       *             *             *             *
GCA ATA TGT TTG CTG CTT GTT TCG CAA TGC AAT GGA AGA ACG
Ala Ile Cys Leu Leu Leu Val Ser Gln Cys Asn Gly Arg Thr 90           100            110          120
     *             *              *            *
GTG AAG AAG TGT GGC AAG AAT GAA AGA TAC GAC GAC TGT GGC
Val Lys Lys Cys Gly Lys Asn Glu Arg Tyr Asp Asp Cys Gly 130          140            150           160
 *            *              *             *
AAT GCA AAG GAC TGC GAG ACC AAG TGC GGT GAA GAG GAA AAG
Asn Ala Lys Asp Cys Glu Thr Lys Cys Gly Glu Glu Glu Lys 170          180            190          200           210
 *            *              *            *             *
GTG TGC CGT TCG CGT GAG TGT ACT AGT CCT GGT GCC TGC GTA
Val Cys Arg Ser Arg Glu Cys Thr Ser Pro Gly Ala Cys Val 220           230           240           250
         *             *             *             *
TGC GAA CAA GGA TTC TAC AGA GAT CCG GCT GGC GAC TGT GTC
Cys Glu Gln Gly Phe Tyr Arg Asp Pro Ala Gly Asp Cys Val 260           270           280           290
         *             *             *             *
ACT GAT GAA GAA TGT GAT GAA TGG AAC AAT ATG GAG ATC ATT
Thr Asp Glu Glu Cys Asp Glu Trp Asn Asn Met Glu Ile Ile 300           310           320           330           340
         *             *             *             *             *
ACT ATG CCA AAA CAG TAG TGCGAAGTTC CCTTCTTTCT CCAAATCTG
Thr Met Pro Lys Gln 350           360           370           380           390
             *             *             *             *             *
           C TCCGTGCTCAATTATCACACACCTCCACTAGTTAAGATTGACTGACTCTCTTG 400           410           420           430           440           450
    *             *             *             *             *             *
CATTGTAGTATTTTCGCTTGACTCTGTGCATTTAAGCATGAGATACTACTAGGGA 460           470
           *             *
GAATAAAAATTACTAACTAC poly(A)
```

Fig. 7D

```
1             10            20            30            40
*             *             *             *             *
GAATTCCGG AAA TGT CCT ACC GAT GAA TGG TTC GAT TGG TGT
EcoRI     Lys Cys Pro Thr Asp Glu Trp Phe Asp Trp Cys 50            60            70            80
        *             *             *             *
GGA ACT TAC AAG CAT TGC GAA CTC AAG TGC GAT AGG GAG CTA
Gly Thr Tyr Lys His Cys Glu Leu Lys Cys Asp Arg Glu Leu 90           100           110           120
        *             *             *             *
ACT GAG AAA GAA GAG CAG GCA TGT CTC TCA CGT GTT TGT GAG
Thr Glu Lys Glu Glu Gln Ala Cys Leu Ser Arg Val Cys Glu 130           140           150           160
        *             *             *             *
AAG TCC GCT TGC GTA TGC AAT GAC GGA TTA TAC AGA GAC AAG
Lys Ser Ala Cys Val Cys Asn Asp Gly Leu Tyr Arg Asp Lys 170           180           190           200           210
     *             *             *             *             *
TTT GGC AAC TGT GTT GAA AAA GAC GAA TGC AAC GAT ATG GAG
Phe Gly Asn Cys Val Glu Lys Asp Glu Cys Asn Asp Met Glu 220           230           240           250
             *             *             *             *
ATT ATT ACT TTT GCA CCA GAA ACC AAA TAA TGGCCTAAGG TTCC
Ile Ile Thr Phe Ala Pro Glu Thr Lys 260           270           280           290           300
          *             *             *             *             *
AAACCT TGCTACACAC CGTCAGTGCTTTACTGTTTCCTCTACGTGTTAGTAGT 310           320           330           340           350           360
     *             *             *             *             *             *
TTTGCTTGACTCTGTGTATTTAAGCATTGTCTACTAATGGGCAAAGTAAAGCATT 370           380           390
         *             *             *
GTAAGGACATAATAATGAGTAAACCTTCTGATTT poly(A)
```

Fig. 7E-1

```
  1          10           20                30              40
  *           *            *                 *               *
GAATTCCGGG CGGCAGAAAG ATG CGA ATG CTC TAC CTT GTT CCT
EcoRI                 Met Arg Met Leu Tyr Leu Val Pro 50              60              70              80
         *               *               *               *
ATC TGG TTG CTG CTC ATT TCG CTA TGC AGT GGA AAA GCT GCG
Ile Trp Leu Leu Leu Ile Ser Leu Cys Ser Gly Lys Ala Ala 90             100             110             120
       *               *               *               *
AAG AAA TGT GGT CTC AAT GAA AGG CTG GAC TGT GGC AAT CTG
Lys Lys Cys Gly Leu Asn Glu Arg Leu Asp Cys Gly Asn Leu 130             140             150             160             170
     *               *               *               *               *
AAG CAA TGC GAG CCC AAG TGC AGC GAC TTG GAA AGT GAG GAG
Lys Gln Cys Glu Pro Lys Cys Ser Asp Leu Glu Ser Glu Glu 180             190             200             210
             *               *               *               *
TAT GAG GAG GAA GAT GAG TCG AAA TGT CGA TCA CGT GAA TGT
Tyr Glu Glu Glu Asp Glu Ser Lys Cys Arg Ser Arg Glu Cys 220             230             240             250
           *               *               *               *
TCT CGT CGT GTT TGT GTA TGC GAT GAA GGA TTC TAC AGA AAC
Ser Arg Arg Val Cys Val Cys Asp Glu Gly Phe Tyr Arg Asn 260             270             280             290
           *               *               *               *
AAG AAG GGC AAG TGT GTT GCA AAA GAT GTT TGC GAG GAC GAC
Lys Lys Gly Lys Cys Val Ala Lys Asp Val Cys Glu Asp Asp 300             310             320             330
         *               *               *               *
AAT ATG GAG ATT ATC ACT TTT CCA CCA GAA GAC GAA TGT GGT
Asn Met Glu Ile Ile Thr Phe Pro Pro Glu Asp Glu Cys Gly 340             350             360             370             380
     *               *               *               *               *
CCC GAT GAA TGG TTC GAC TAC TGT GGA AAT TAT AAG AAG TGC
Pro Asp Glu Trp Phe Asp Tyr Cys Gly Asn Tyr Lys Lys Cys 390             400             410             420
           *               *               *               *
GAA CGC AAG TGC AGT GAG GAG ACA AGT GAG AAA AAT GAG GAG
Glu Arg Lys Cys Ser Glu Glu Thr Ser Glu Lys Asn Glu Glu 430             440             450             460
           *               *               *               *
GCA TGC CTC TCT CGT GCT TGT ACT GGT CGT GCT TGC GTA TGC
Ala Cys Leu Ser Arg Ala Cys Thr Gly Arg Ala Cys Val Cys
```

Fig. 7E-2

```
      470           480           490           500
       *             *             *             *
AAA GAC GGA TTG TAC AGA GAC GAC TTT GGC AAC TGT GTT CCA
Lys Asp Gly Leu Tyr Arg Asp Asp Phe Gly Asn Cys Val Pro 510           520           530           540
       *             *             *             *
CAT GAC GAA TGC AAC GAT ATG GAG ATC ATC ACT TTT CCA CCG
His Asp Glu Cys Asn Asp Met Glu Ile Ile Thr Phe Pro Pro 550           560           570           580           590
       *             *             *             *             *
GAA ACC AAA CAT TGA CCAGAGGCTC CAACTCTCGC TACACAACGT CA
Glu Thr Lys His 600         610         620         630         640         650
       *           *           *           *           *           *
GGGCTAGAATGGCCCCTCTGCGAGTTAGTAGTTTTGCTTGACTCTGCTTATTTGA 660         670         680
            *           *           *
GCACTTTCTATTGATGGCGAAAATAAAGCATTTAAAAC poly(A)
```

Fig. 7F

```
        1          10         20         30         40
        *          *          *          *          *
       GAATTCCGCG CACCTGAGAG GTGAGCTACG CAAGTCTTCG CTGGTACA
       EcoRI 50         60         70         80         90
   *          *          *          *          *
  ATG ATC CGA AAG CTC GTT CTG CTG ACT GCT ATC GTC ACG GTG
  Met Ile Arg Lys Leu Val Leu Leu Thr Ala Ile Val Thr Val 100        110        120        130
              *          *          *          *
  GTG CTA AGT GCG AAG ACC TGT GGA CCA AAC GAG GAG TAC ACT
  Val Leu Ser Ala Lys Thr Cys Gly Pro Asn Glu Glu Tyr Thr 140        150        160        170
         *          *          *          *
  GAA TGC GGG ACG CCA TGC GAG CCG AAG TGC AAT GAA CCG ATG
  Glu Cys Gly Thr Pro Cys Glu Pro Lys Cys Asn Glu Pro Met 180        190        200        210
         *          *          *          *
  CCA GAC ATC TGT ACT CTG AAC TGC ATC GTG AAC GTG TGT CAG
  Pro Asp Ile Cys Thr Leu Asn Cys Ile Val Asn Val Cys Gln 220        230        240        250
         *          *          *          *
  TGC AAA CCC GGC TTC AAG CGC GGA CCG AAA GGA TGC GTC GCC
  Cys Lys Pro Gly Phe Lys Arg Gly Pro Lys Gly Cys Val Ala 260        270        280        290        300
    *          *          *          *          *
  CCC GGA CCA GGC TGT AAA TAG TTCTCCACCT GCCCTTTCGT TGGAA
  Pro Gly Pro Gly Cys Lys 310        320        330        340
         *          *          *          *
  CAAAT GGCTGTCTTTTTACATTCTGAATCAATAAAGCCGAACGGT poly(A)
```

Fig. 8A

```
1          10          20          30          40
*          *           *           *           *
AAGCTTTGCT AACATACTGC GTAATAAGGA GTCTTAATC ATG CCA GTT
HindIII                                      Met Pro Val 50         60          70          80          90
*          *           *           *           *
CTT TTG GGT ATT CCG TTA TTA TTG CGT TTC CTC GGT TTC CTT
Leu Leu Gly Ile Pro Leu Leu Leu Arg Phe Leu Gly Phe Leu 100         110         120         130
            *           *           *           *
CTG GTA ACT TTG TTC GGC TAT CTG CTT ACT TTC CTT AAA AAG
Leu Val Thr Leu Phe Gly Tyr Leu Leu Thr Phe Leu Lys Lys 140         150         160         170
      *           *           *           *
GGC TTC GGT AAG ATA GCT ATT GCT ATT TCA TTG TTT CTT GCT
Gly Phe Gly Lys Ile Ala Ile Ala Ile Ser Leu Phe Leu Ala 180         190         200         210
      *           *           *           *
CTT ATT ATT GGG CTT AAC TCA ATT CTT GTG GGT TAT CTC TCT
Leu Ile Ile Gly Leu Asn Ser Ile Leu Val Gly Tyr Leu Ser 220         230         240         250
      *           *           *           *
GAT ATT AGC GCA CAA TTA CCC TCT GAT TTT GTT CAG GGC GTT
Asp Ile Ser Ala Gln Leu Pro Ser Asp Phe Val Gln Gly Val 260         270         280         290         300
*           *           *           *           *
CAG TTA ATT CTC CCG TCT AAT GCG CTT CCC TGT TTT TAT GTT
Gln Leu Ile Leu Pro Ser Asn Ala Leu Pro Cys Phe Tyr Val 310         320         330         340
            *           *           *           *
ATT CTC TCT GTA AAG GCT GCT ATT TTC ATT TTT GAC GTT AAA
Ile Leu Ser Val Lys Ala Ala Ile Phe Ile Phe Asp Val Lys 350         360         370         380
            *           *           *           *
CAA AAA ATC GTT TCT TAT TTG GAT TGG GAT AAA GGT GGA GGC
Gln Lys Ile Val Ser Tyr Leu Asp Trp Asp Lys Gly Gly Gly 390         400         410         420         430
      *           *           *           *           *
TCA GGC GGA GGCCAAGTCGGCC ATCCCATATCAC GCGGCCGC GGATCC
Ser Gly Gly     SfiI                   NotI     BamHI
```

Fig. 8B

```
1          10         20         30         40
*          *          *          *          *
AAGCTTTGCT AACATACTGC GTAATAAGGA GTCTTAATC ATG CCA GTT
HindIII                                     Met Pro Val 50             60             70             80             90
*              *              *              *              *
CTT TTG GGT ATT CCG TTA TTA TTG CGT TTC CTC GGT TTC CTT
Leu Leu Gly Ile Pro Leu Leu Leu Arg Phe Leu Gly Phe Leu 100            110            120            130
            *              *              *              *
CTG GTA ACT TTG TTC GGC TAT CTG CTT ACT TTC CTT AAA AAG
Leu Val Thr Leu Phe Gly Tyr Leu Leu Thr Phe Leu Lys Lys 140            150            160            170
        *              *              *              *
GGC TTC GGT AAG ATA GCT ATT GCT ATT TCA TTG TTT CTT GCT
Gly Phe Gly Lys Ile Ala Ile Ala Ile Ser Leu Phe Leu Ala 180            190            200            210
    *              *              *              *
CTT ATT ATT GGG CTT AAC TCA ATT CTT GTG GGT TAT CTC TCT
Leu Ile Ile Gly Leu Asn Ser Ile Leu Val Gly Tyr Leu Ser 220            230            240            250
*              *              *              *
GAT ATT AGC GCA CAA TTA CCC TCT GAT TTT GTT CAG GGC GTT
Asp Ile Ser Ala Gln Leu Pro Ser Asp Phe Val Gln Gly Val 260            270            280            290            300
*              *              *              *              *
CAG TTA ATT CTC CCG TCT AAT GCG CTT CCC TGT TTT TAT GTT
Gln Leu Ile Leu Pro Ser Asn Ala Leu Pro Cys Phe Tyr Val 310            320            330            340
        *              *              *              *
ATT CTC TCT GTA AAG GCT GCT ATT TTC ATT TTT GAC GTT AAA
Ile Leu Ser Val Lys Ala Ala Ile Phe Ile Phe Asp Val Lys 350            360            370            380
        *              *              *              *
CAA AAA ATC GTT TCT TAT TTG GAT TGG GAT AAA GGT GGA GGC
Gln Lys Ile Val Ser Tyr Leu Asp Trp Asp Lys Gly Gly Gly 390            400            410            420            430
    *              *              *              *              *
TCA GGC GGA G GGCCAAGTCGGCC ATCCCATATCAC GCGGCCGC GGATCC
Ser Gly Gly       SfiI                   NotI      BamHI
```

Fig. 8C

```
1          10         20         30         40
*          *          *          *          *
AAGCTTTGCT AACATACTGC GTAATAAGGA GTCTTAATC ATG CCA GTT
HindIII                                    Met Pro Val 50             60             70             80             90
*              *              *              *              *
CTT TTG GGT ATT CCG TTA TTA TTG CGT TTC CTC GGT TTC CTT
Leu Leu Gly Ile Pro Leu Leu Leu Arg Phe Leu Gly Phe Leu 100            110            120            130
            *              *              *              *
CTG GTA ACT TTG TTC GGC TAT CTG CTT ACT TTC CTT AAA AAG
Leu Val Thr Leu Phe Gly Tyr Leu Leu Thr Phe Leu Lys Lys 140            150            160            170
        *              *              *              *
GGC TTC GGT AAG ATA GCT ATT GCT ATT TCA TTG TTT CTT GCT
Gly Phe Gly Lys Ile Ala Ile Ala Ile Ser Leu Phe Leu Ala 180            190            200            210
        *              *              *              *
CTT ATT ATT GGG CTT AAC TCA ATT CTT GTG GGT TAT CTC TCT
Leu Ile Ile Gly Leu Asn Ser Ile Leu Val Gly Tyr Leu Ser 220            230            240            250
    *              *              *              *
GAT ATT AGC GCA CAA TTA CCC TCT GAT TTT GTT CAG GGC GTT
Asp Ile Ser Ala Gln Leu Pro Ser Asp Phe Val Gln Gly Val 260            270            280            290            300
*              *              *              *              *
CAG TTA ATT CTC CCG TCT AAT GCG CTT CCC TGT TTT TAT GTT
Gln Leu Ile Leu Pro Ser Asn Ala Leu Pro Cys Phe Tyr Val 310            320            330            340
            *              *              *              *
ATT CTC TCT GTA AAG GCT GCT ATT TTC ATT TTT GAC GTT AAA
Ile Leu Ser Val Lys Ala Ala Ile Phe Ile Phe Asp Val Lys 350            360            370            380
        *              *              *              *
CAA AAA ATC GTT TCT TAT TTG GAT TGG GAT AAA GGT GGA GGC
Gln Lys Ile Val Ser Tyr Leu Asp Trp Asp Lys Gly Gly Gly 390            400            410            420            430
        *              *              *              *              *
TCA GGC GGA TC GGCCAAGTCGGCC ATCCCATATCAC GCGGCCGC GGATCC
Ser Gly Gly         SfiI                   NotI     BamHI
```

Fig. 9

```
1          10              20              30              40
*          *               *               *               *
GAATTCCGG  CTG GTW TCC TAC TGC AGT GGA AAA GCA ACG ATG
EcoRI      Leu Val Ser Tyr Cys Ser Gly Lys Ala Thr Met 50              60              70              80
      *               *               *               *
CAG TGT GGT GAG AAT GAA AAG TAC GAT TCG TGC GGT AGC AAG
Gln Cys Gly Glu Asn Glu Lys Tyr Asp Ser Cys Gly Ser Lys 90              100             110             120
      *               *               *               *
GAG TGC GAT AAG AAG TGC AAA TAT GAC GGA GTT GAG GAG GAA
Glu Cys Asp Lys Lys Cys Lys Tyr Asp Gly Val Glu Glu Glu 130             140             150             160
      *               *               *               *
GAC GAC GAG GAA CCT AAT GTG CCA TGC CTA GTA CGT GTG TGT
Asp Asp Glu Glu Pro Asn Val Pro Cys Leu Val Arg Val Cys 170             180             190             200             210
*               *               *               *               *
CAT CAA GAT TGC GTA TGC GAA GAA GGA TTC TAT AGA AAC AAA
His Gln Asp Cys Val Cys Glu Glu Gly Phe Tyr Arg Asn Lys 220             230             240             250
      *               *               *               *
GAT GAC AAA TGT GTA TCA GCA GAA GAC TGC GAA CTT GAC AAT
Asp Asp Lys Cys Val Ser Ala Glu Asp Cys Glu Leu Asp Asn 260             270             280             290
      *               *               *               *
ATG GAC TTT ATA TAT CCC GGA ACT CGA AAC TGA ACGAAGGCTC
Met Asp Phe Ile Tyr Pro Gly Thr Arg Asn 300             310             320             330             340
      *               *               *               *               *
CATTCTTGCT GCACAAGATC GATTGTCTCTCCCCTGCATCTCAGTAGTTTTGC 350         360         370         380         390         400
*           *           *           *           *           *
TACATTGTATATGGTAGCAAAAAATTAGCTTAGGGAGAATAAAATCTTTACCTAT 410         420         430
      *           *           *
ATTTAATCAATGAAGTATTCTCTTTCT poly(A)
```

Figure 11-1

| | | | | | | | | | | | |
|---|---|---|---|---|---|---|---|---|---|---|---|
| NAP5 | Met | Lys | Met | Leu | Tyr | Ala | Ile | Ala | Ile | Met | Phe | Leu | Leu | Val |
| NAP6 | Met | Lys | Met | Leu | Tyr | Ala | Ile | Ala | Ile | Met | Phe | Leu | Leu | Val |
| NAPc2 | | | | | | | | | | | | Leu | Val |
| AceNAP5 | Met | Arg | Thr | Leu | Tyr | Leu | Ile | Ser | Ile | Trp | Leu | Phe | Leu | Ile |
| AceNAP7 | Met | Ser | Thr | Leu | Tyr | Val | Ile | Ala | Ile | Cys | Leu | Leu | Leu | Val |
| AceNAP4d1 | Met | Ala | Val | Leu | Tyr | Ser | Val | Ala | Ile | Ala | Leu | Leu | Leu | Val |
| AceNAP4d2 | | | | | | | | | | | | | |
| AduNAP4 | | | | | | | | | | | | | |
| AduNAP7d1 | Met | Arg | Met | Leu | Tyr | Leu | Val | Pro | Ile | Trp | Leu | Leu | Leu | Ile |
| AduNAP7d2 | | | | | | | | | | | | | |
| HpoNAP5 | Met | Ile | Arg | Lys | Leu | Val | Leu | Leu | Thr | Ala | Ile | Val | Thr |

Figure 11-2

| | | | | | | | | | | | | | | |
|---|---|---|---|---|---|---|---|---|---|---|---|---|---|---|
| NAP5 | Ser | Leu | Cys | Ser | Ala | Arg | Thr | Val | Arg | Lys | Ala | Tyr | Pro | Glu |
| NAP6 | Ser | Leu | Cys | Ser | Thr | Arg | Thr | Val | Arg | Lys | Ala | Tyr | Pro | Glu |
| NAPc2 | Ser | Tyr | Cys | Ser | Gly | - - - | - - - | - - - | - - - | Lys | Ala | Thr | Met | Gln |
| AceNAP5 | Ser | Gln | Cys | Asn | Gly | - - - | - - - | - - - | - - - | Lys | Ala | Phe | Pro | Lys |
| AceNAP7 | Ser | Gln | Cys | Asn | Gly | - - - | - - - | - - - | - - - | Arg | Thr | Val | Lys | Lys |
| AceNAP4d1 | Ser | Gln | Cys | Ser | Gly | Lys | Pro | Asn | Asn | Val | Met | Thr | Asn | Ala |
| AceNAP4d2 | | | | | | | | Val | Pro | Ile | | | | |
| AduNAP4 | | | | | | | | | | Lys | | | | |
| AduNAP7d1 | Ser | Leu | Cys | Ser | Gly | - - - | - - - | - - - | - - - | Lys | Ala | Ala | Lys | Lys |
| AduNAP7d2 | | | | | | | | | | | | | Asp | Glu |
| HpoNAP5 | Val | Val | Leu | Ser | Ala | - - - | - - - | - - - | - - - | - - - | - - - | - - - | Lys | Thr |

Figure 11-3

| | 1 | | | | | | | | | 2 | | | |
|---|---|---|---|---|---|---|---|---|---|---|---|---|---|
| NAP5 | Cys | Gly | Glu | Asn | Glu | Trp | Leu | Asp | Asp | Cys | Gly | Thr | Gln |
| NAP6 | Cys | Gly | Glu | Asn | Glu | Trp | Leu | Asp | Val | Cys | Gly | Thr | Lys |
| NAPc2 | Cys | Gly | Glu | Asn | Glu | Lys | Tyr | Asp | Ser | Cys | Gly | Ser | Lys |
| AceNAP5 | Cys | Asp | Val | Asn | Glu | Arg | Phe | Glu | Val | Cys | Gly | Asn | Leu |
| AceNAP7 | Cys | Gly | Lys | Asn | Glu | Arg | Tyr | Asp | Asp | Cys | Gly | Asn | Ala |
| AceNAP4d1 | Cys | Gly | Leu | Asn | Glu | Tyr | Phe | Ala | Glu | Cys | Gly | Asn | Met |
| AceNAP4d2 | Cys | Gly | Ser | Asn | Glu | Arg | Tyr | Ser | Asp | Cys | Gly | Asn | Asp |
| AduNAP4 | Cys | Pro | Thr | Asp | Glu | Trp | Phe | Asp | Trp | Cys | Gly | Thr | Tyr |
| AduNAP7d1 | Cys | Gly | Leu | Asn | Glu | Arg | Leu | Asp | --- | Cys | Gly | Asn | Leu |
| AduNAP7d2 | Cys | Pro | Asp | Asn | Glu | Trp | Phe | Asp | Tyr | Cys | Gly | Asn | Tyr |
| HpoNAP5 | Cys | Gly | Pro | Asn | Glu | Glu | Tyr | Thr | Glu | Cys | Gly | Thr | --- |

Figure 11-4

| | | | 3 | | | | 4 | | | | | | | |
|---|---|---|---|---|---|---|---|---|---|---|---|---|---|---|
| NAP5 | Lys | Pro | Cys | Glu | Ala | Lys | Cys | --- | --- | --- | --- | Asn | Glu | Glu |
| NAP6 | Lys | Pro | Cys | Glu | Ala | Lys | Cys | --- | --- | --- | --- | Ser | Glu | Glu |
| NAPc2 | Glu | --- | Cys | Asp | Lys | Lys | Cys | Lys | Tyr | Asp | Gly | --- | --- | --- |
| AceNAP5 | Lys | Glu | Cys | Glu | Leu | Lys | Cys | --- | --- | --- | --- | --- | --- | --- |
| AceNAP7 | Lys | Asp | Cys | Glu | Thr | Lys | Cys | --- | --- | --- | --- | --- | Gly | --- |
| AceNAP4d1 | Lys | Glu | Cys | Glu | His | Arg | Cys | Asn | Glu | Glu | Glu | Asn | Glu | Glu |
| AceNAP4d2 | Lys | Gln | Cys | Glu | Arg | Lys | Cys | Asn | Glu | Asp | Asp | Tyr | Glu | Lys |
| AduNAP4 | Lys | His | Cys | Glu | Leu | Lys | Cys | Asp | Arg | Glu | Leu | Thr | Glu | Lys |
| AduNAP7d1 | Lys | Gln | Cys | Glu | Pro | Lys | Cys | Ser | Asp | Leu | Glu | Ser | Glu | Glu |
| AduNAP7d2 | Lys | Lys | Cys | Glu | Arg | Lys | Cys | Ser | Glu | Thr | Ser | Glu | Glu | Lys |
| HpoNAP5 | --- | Pro | Cys | Glu | Pro | Lys | Cys | --- | --- | --- | --- | --- | --- | --- |

Figure 11-5

| | | | | | | | | | | | 5 | | | |
|---|---|---|---|---|---|---|---|---|---|---|---|---|---|---|
| NAP5 | Pro | Pro | Glu | Glu | Glu | Asp | Pro | Ile | --- | --- | Cys | Arg | Ser | Arg |
| NAP6 | --- | --- | Glu | Glu | Glu | Asp | Pro | Ile | --- | --- | Cys | Arg | Ser | Phe |
| NAPc2 | --- | Glu | Asp | Asp | Glu | Glu | Pro | Asn | Val | Pro | Cys | Leu | Val | Arg |
| AceNAP5 | --- | --- | Asp | Asp | Asp | Pro | --- | --- | --- | --- | Cys | --- | Ser | Arg |
| AceNAP7 | --- | --- | Glu | Glu | Glu | --- | --- | Lys | --- | Val | Cys | Arg | Ser | Arg |
| AceNAP4d1 | Arg | --- | Asp | Glu | Glu | --- | --- | Arg | Ile | Thr | Ala | Cys | Leu | Ile | Arg |
| AceNAP4d2 | Gly | --- | Asp | Glu | --- | --- | --- | --- | --- | --- | Ala | Cys | Arg | Ser | His |
| AduNAP4 | --- | --- | Glu | Glu | --- | --- | --- | Gln | --- | --- | Ala | Cys | Leu | Ser | Arg |
| AduNAP7d1 | Tyr | --- | Glu | Asp | Glu | Asp | Glu | Ser | Lys | --- | --- | Cys | Arg | Ser | Arg |
| AduNAP7d2 | Asn | --- | Glu | Glu | --- | --- | --- | --- | --- | --- | Ala | Cys | Leu | Ser | Arg |
| HpoNAP5 | --- | --- | Asn | Glu | Pro | Met | Pro | Asp | Ile | --- | --- | Cys | --- | Thr | Leu |

Figure 11-6

| | 6 | | | | | 7 | | 8 | | |
|---|---|---|---|---|---|---|---|---|---|---|
| NAP5 | Gly Cys | Leu | Leu | Pro | Pro | Ala Cys | Val | Cys | Lys | Asp |
| NAP6 | Ser Cys | Pro | Gly | Pro | Ala | Ala Cys | Val | Cys | Glu | Asp |
| NAPc2 | Val Cys | His | Gln | Asp | - - - | Cys | Val | Cys | Glu | Glu |
| AceNAP5 | Ala Cys | Ile | Arg | Pro | Ala | Ala Cys | Val | Cys | Asp | Asp |
| AceNAP7 | Glu Cys | Thr | Ser | Pro | Gly | Ala Cys | Val | Cys | Glu | Gln |
| AceNAP4d1 | Val Cys | Phe | Arg | Pro | Gly | Ala Cys | Val | Cys | Lys | Asp |
| AceNAP4d2 | Val Cys | Glu | Arg | Pro | Gly | Ala Cys | Val | Cys | Glu | Asp |
| AduNAP4 | Val Cys | Glu | Lys | - - - | Ser | Ala Cys | Val | Cys | Asn | Asp |
| AduNAP7d1 | Glu Cys | Ser | Arg | Arg | - - - | Val Cys | Val | Cys | Asp | Glu |
| AduNAP7d2 | Ala Cys | Thr | Gly | Arg | - - - | Ala Cys | Val | Cys | Lys | Asp |
| HpoNAP5 | Asn Cys | Ile | Val | Asn | - - - | Val Cys | Gln | Cys | Lys | Pro |

Figure 11-7

|          |     |     |     |     |     |     |     |     |     | 9   |     |     |     |
|----------|-----|-----|-----|-----|-----|-----|-----|-----|-----|-----|-----|-----|-----|
| NAP5     | Gly | Phe | Tyr | Arg | Asp | Thr | Val | Ile | Gly | Asp | Cys | Val | Arg | Glu |
| NAP6     | Gly | Phe | Tyr | Arg | Asp | Thr | Val | Ile | Gly | Asp | Cys | Val | Lys | Glu |
| NAPc2    | Gly | Phe | Tyr | Arg | Asn | Lys | --- | Asp | Asp | Lys | Cys | Val | Ser | Ala |
| AceNAP5  | Gly | Phe | Tyr | Arg | Asp | Lys | Tyr | --- | Gly | Phe | Cys | Val | Glu | Glu |
| AceNAP7  | Gly | Phe | Tyr | Arg | Asp | Pro | Ala | --- | Gly | Asp | Cys | Val | Thr | Asp |
| AceNAP4d1 | Gly | Phe | Tyr | Arg | Asn | Arg | Thr | --- | Gly | Ser | Cys | Val | Glu | Glu |
| AceNAP4d2 | Gly | Phe | Tyr | Arg | Asn | Lys | Lys | --- | Gly | Ser | Cys | Val | Glu | Ser |
| AduNAP4  | Gly | Phe | Tyr | Arg | Asp | Lys | Phe | --- | Gly | Asn | Cys | Val | Glu | Lys |
| AduNAP7d1 | Gly | Leu | Tyr | Arg | Asn | Lys | Lys | --- | Gly | Lys | Cys | Val | Ala | Lys |
| AduNAP7d2 | Gly | Phe | Tyr | Arg | Asp | Asp | Phe | --- | Gly | Asn | Cys | Val | Pro | His |
| HpoNAP5  | Gly | Phe | Lys | Arg | Gly | Pro | Lys | --- | Gly | --- | Cys | Val | Ala | Pro |

Figure 11-8

|  |  |  | 10 |  |  |  |  |  |  |  |  |  |
|---|---|---|---|---|---|---|---|---|---|---|---|---|
| NAP5 | Glu | Glu | Cys | Asp | Gln | His | --- | --- | --- | Glu | Ile | Ile | His |
| NAP6 | Glu | Glu | Cys | Asp | Gln | His | --- | --- | --- | Glu | Ile | Ile | His |
| NAPc2 | Glu | Asp | Cys | Glu | --- | Leu | Asp | Asn | Met | Asp | Phe | Ile | Tyr |
| AceNAP5 | Asp | Glu | Cys | Asn | Asp | --- | --- | --- | Met | Glu | Ile | Ile | Thr |
| AceNAP7 | Glu | Glu | Cys | Asp | Glu | Trp | Asn | Asn | Met | Glu | Ile | Ile | Thr |
| AceNAP4d1 | Asp | Asp | Cys | Glu | --- | Tyr | Glu | Asn | Met | Glu | Phe | Ile | Thr |
| AceNAP4d2 | Asp | Asp | Cys | Glu | --- | Tyr | Asp | Asn | Met | Glu | Ile | Ile | Thr |
| AduNAP4 | Asp | Glu | Cys | Asn | Asp | --- | --- | --- | Met | Glu | Ile | Ile | Thr |
| AduNAP7d1 | Asp | Val | Cys | Glu | Asp | --- | Asp | Asn | Met | Glu | Phe | Ile | Thr |
| AduNAP7d2 | Asp | Glu | Cys | Asn | Asp | --- | --- | --- | Met | Glu | Ile | Ile | Thr |
| HpoNAP5 | Gly | Pro | Gly | Cys | Lys | end | | | | | | | |

Figure 11-9

NAP5        Val end

NAP6        Val end

NAPc2       Pro Gly Thr Arg Asn end

AceNAP5     Phe Pro Pro Glu Thr Lys end

AceNAP7     Met Pro Lys Gln end

AceNAP4d1   Phe Ala Pro Glu

AceNAP4d2   Phe Ala Pro Glu Thr Ser Arg end

AduNAP4     Phe Ala Pro Glu Thr Lys end

AduNAP7d1   Phe Pro Pro Glu

AduNAP7d2   Phe Pro Pro Glu Thr Lys His end

HpoNAP5

```
<----5'AOX1------><--------PHO1 secretion signal (S)--
......TTATTCGAAACGATGTTCTCTCCAATTTTGTCCTTGGAAATTATTTTA -------------------------><----Pro Sequence (P)---------
GCTACTTTGCAATCTGTCTTCGCCCAGCCAGTTATCTCCACTACCGTTGGTTCC -------------------------><-Multi-Cloning Site (MCS)
GCTGCCGAGGGTTCTTTGGACAAGAGGCCTATCCGCGGAATTCAGATCTGAAT
                           StuI    SacIIEcoRI BglII -------------------------><---3'T---->
GCGGCCGCTCGAGACTAGTGGATCCTTAGACA...
NotI  XhoI  SpeI  BamHI
 EagI
```

NEMATODE-EXTRACTED ANTICOAGULANT PROTEIN

This is a continuation Ser. No. 08/326,110, filed Oct. 18, 1994.

FIELD OF THE INVENTION

The present invention relates to specific proteins as well as recombinant versions of these proteins which are potent anticoagulants in human plasma. These proteins include certain proteins extracted from nematodes. In another aspect, the present invention relates to compositions comprising these proteins, which are useful as potent and specific inhibitors of blood coagulation in vitro and in vivo, and methods for their use as in vitro diagnostic agents, or as in vivo therapeutic agents, to prevent the clotting of blood. In a further aspect, the invention relates to nucleic acid sequences, including mRNA and DNA, encoding the proteins and their use in vectors to transfect or transform host cells and as probes to isolate certain related genes in other species and organisms.

BACKGROUND OF AND INTRODUCTION TO THE INVENTION

Normal hemostasis is the result of a delicate balance between the processes of clot formation (blood coagulation) and clot dissolution (fibrinolysis). The complex interactions between blood cells, specific plasma proteins and the vascular surface, maintain the fluidity of blood unless injury occurs. Damage to the endothelial barrier lining the vascular wall exposes underlying tissue to these blood components. This in turn triggers a series of biochemical reactions altering the hemostatic balance in favor of blood coagulation which can either result in the desired formation of a hemostatic plug stemming the loss of blood or the undesirable formation of an occlusive intravascular thrombus resulting in reduced or complete lack of blood flow to the affected organ.

The blood coagulation response is the culmination of a series of amplified reactions in which several specific zymogens of serine proteases in plasma are activated by limited proteolysis. This series of reactions results in the formation of an insoluble matrix composed of fibrin and cellular components which is required for the stabilization of the primary hemostatic plug or thrombus. The initiation and propagation of the proteolytic activation reactions occurs through a series of amplified pathways which are localized to membranous surfaces at the site of vascular injury (Mann, K. G., Nesheim, M. E., Church, W. R., Haley, P. and Krishnaswamy, S. (1990) Blood 76: 1–16, and Lawson, J. H., Kalafatis, M., Stram, S., and Mann, K. G. (1994) J. Biol. Chem. 269: 23357–23366).

Initiation of the blood coagulation response to vascular injury follows the formation of a catalytic complex composed of serine protease factor VIIa and the non-enzymatic co-factor, tissue factor (TF)(Rappaport, S. I. and Rao, L. V. M. (1992) Arteriosclerosis and Thrombosis 12: 1112–1121). This response appears to be exclusively regulated by the exposure of subendothelial TF to trace circulating levels of factor VIIa and its zymogen factor VII, following a focal breakdown in vascular integrity. Autoactivation results in an increase in the number of factor VIIa/TF complexes which are responsible for the formation of the serine protease factor Xa. It is believed that in addition to the factor VIIa/TF complex, the small amount of factor Xa which is formed primes the coagulation response through the proteolytic modification of factor IX to factor IX$_{alpha}$ which in turn is converted to the active serine protease factor IXa$_b$ by the factor VIIa/TF complex (Mann, K. G., Krishnaswamy, S. and Lawson, J. H. (1992) Sem. Hematology 29: 213–226.). It is factor IXa$_b$ in complex with activated factor VIIIa, which appears to be responsible for the production of significant quantities of factor Xa which subsequently catalyzes the penultimate step in the blood coagulation cascade; the formation of the serine protease thrombin.

Factor Xa catalyzes the formation of thrombin following the assembly of the prothrombinase complex which is composed of factor Xa, the non-enzymatic co-factor Va and the substrate prothrombin (factor II) assembled in most cases, on the surface of activated platelets which are adhered at the site of injury (Fuster, V., Badimon, L., Badimon, J. J. and Chesebro, J. H. (1992) New Engl. J. Med. 326: 310–318). In the arterial vasculature, the resulting amplified "burst" of thrombin generation catalyzed by prothrombinase results locally high levels of this protease which is responsible for the formation of fibrin and the further recruitment of additional platelets as well as the covalent stabilization of the clot through the activation of the transglutaminase zymogen factor XIII. In addition, the coagulation response is further propagated through the thrombin-mediated proteolytic feedback activation of the non-enzymatic co-factors V and VIII resulting in more prothrombinase formation and subsequent thrombin generation (Hemker, H. C. and Kessels, H. (1991) Haemostasis 21: 189–196).

Substances which interfere in the process of blood coagulation (anticoagulants) have been demonstrated to be important therapeutic agents in the treatment and prevention of thrombotic disorders (Kessler, C. M. (1991) Chest 99: 97S–112S and Cairns, J. A., Hirsh, J., Lewis, H. D., Resnekov, L., and Theroux, P. (1992) Chest 102: 456S481S). The currently approved clinical anticoagulants have been associated with a number of adverse effects owing to the relatively non-specific nature of their effect on the blood coagulation cascade (Levine, M. N., Hirsh, J., Landefeld, S., and Raskob, G. (1992) Chest 102: 352S–363S). This has stimulated the search for more effective anticoagulant agents which can more effectively control the activity of the coagulation cascade by selectively interfering with specific reactions in this process which may have a positive effect in reducing the complications of anticoagulant therapy (Weitz, J., and Hirsh, J. (1993) J. Lab. Clin. Med. 122: 364–373). In another aspect, this search has focused on normal human proteins which serve as endogenous anticoagulants in controlling the activity of the blood coagulation cascade. In addition, various hematophageous organisms have been investigated because of their ability to effectively anticoagulate the blood meal during and following feeding on their hosts suggesting that they have evolved effective anticoagulant strategies which may be useful as therapeutic agents.

A plasma protein, Lipoprotein-Associated Coagulation Inhibitor (LACI) or recently termed Tissue Factor Pathway Inhibitor (TFPI), containing three consecutive Kunitz domains has been reported to inhibit the enzyme activity of factor Xa directly and, in a factor Xa-dependent manner, inhibit the enzyme activity the factor VIIa-tissue factor complex. Salvensen, G., and Pizzo, S. V., "Proteinase Inhibitors: α-Macroglobulines, Serpins, and Kunis", Hemostasis and Thrombosis, Third Edition, pp. 251–253, J. B. Lippincott Company (Edit. R. W. Colman et al. 1994). A cDNA sequence encoding TFPI has been reported, and the cloned protein was reported to have a molecular weight of 31,950 daltons and contain 276 amino acids. Broze, G. J. and Girad, T. J., U.S. Pat. No. 5,106,833, col. 1, (1992). Various recombinant proteins derived from TFPI have been reported. Girad, T. J. and Broze, G. J., EP 439,442 (1991); Rasmussen, J. S. and Nordfand, O. J., WO 91/02753 (1991); and Broze, G. J. and Girad, T. J., U.S. Pat. No. 5,106,833, col. 1, (1992).

Antistasin, a protein comprised of 119 amino acids and found in the salivary gland of the Mexican leech, *Haementeria officinalis*, has been reported to inhibit the enzyme activity of factor X*a*. Tuszynski et al., J. Biol. Chem, 262:9718 (1987); Nutt, et al., J. Biol. Chem, 263:10162 (1988). A 6,000 daltons recombinant protein containing 58 amino acids with a high degree homology to antistasin's amino-terminus amino acids 1 through 58 has been reported to inhibit the enzyme activity of factor X*a*. Tung, J. et al., EP 454,372 (Oct. 30, 1991); Tung, J. et al., U.S. Pat. No. 5,189,019 (Feb. 23, 1993).

Tick Anticoagulant Protein (TAP), a protein comprised of 60 amino acids and isolated from the soft tick, *Ornithodoros moubata*, has been reported to inhibit the enzyme activity of factor X*a* but not factor VIIA. Waxman, L. et al., Science, 248:593 (1990). TAP made by recombinant methods has been reported. Vlausk, G. P. et al., EP 419,099 (1991) and Vlausk, G. P. et al., U.S. Pat. No. 5,239,058 (1993).

The dog hookworm, *Ancylostoma caninum*, which can also infect humans, has been reported to contain a potent anticoagulant substance. A. caninum was reported to contain substance which inhibited coagulation of blood in vitro. Loeb, L. and Smith, A. J., Proc. Pathol. Soc. Philadelphia, 7:173–178 (1904). Extracts of *A. caninum* were reported to prolong prothrombin time and partial thromboplastin time in human plasma with the anticoagulant effect being reported attributable to inhibition of factor X*a* but not thrombin. Spellman, Jr., J. J. and Nossel H. L., Am. J. Physiol., 220:922–927 (1971). More recently, soluble protein extracts of *A. caninum* were reported to prolong prothrombin time and partial thromboplastin time in human plasma in vitro. The anticoagulant effect was reported to be attributable to inhibition of human factor X*a* but not thrombin. Cappello, M, et al., J. Infect. Diseases, 167:1474–1477 (1993).

The human hookworm, *Ancylostoma ceylanicum*, has also been reported to contain an anticoagulant. Extracts of *A. ceylanicum* have been reported to prolong prothrombin time and partial thromboplastin time in dog and human plasma in vitro. Carroll, S. M., et al., Thromb. Haemostas. (Stuttgart), 51:222–227 (1984).

Soluble extracts of the parasite, *Ascaris suum*, have been reported to contain an anticoagulant. These extracts were reported to prolong the clotting of whole blood, as well as clotting time in the kaolin-activated partial thromboplastin time test but not in the prothrombin time test. Crawford, G. P. M. et al., J. Parasitol., 68: 1044–1047 (1982). Chymotrypsin/elastase inhibitor-1 and its major isoforms, trypsin inhibitor-1 and chymotrypsin/elastase inhibitor-4, isolated from *Ascaris suum*, were reported to be serine protease inhibitors and share a common pattern of five-disulfide bridges. Bernard, V. D. and Peanasky, R. J., Arch. Biochem. Biophys., 303:367–376 (1993); Huang, K. et al., Structure, 2:679–689 (1994); and Grasberger, B. L. et al., Structure, 2:669–678 (1994). There was no indication that the reported serine protease inhibitors had anticoagulant activity.

SUMMARY OF THE INVENTION

The present invention is directed to isolated proteins having anticoagulant activity and including at least one NAP domain. We refer to these proteins as Nematode-extracted Anticoagulant Proteins or "NAPs". "NAP domain" refers to a sequence of the isolated protein or NAP believed to have anticoagulant activity. The anticoagulant activity of these proteins may be assessed by their activities in increasing clotting time of human plasma in the prothrombin time (PT) and activated partial thromboplastin time (aPTT) assays. It is believed that the NAP domain is responsible for the observed anticoagulent activity of these proteins. Certain of these proteins have at least one NAP domain which is an amino acid sequence having a molecular weight of about 5.0 to 8.0 kilodaltons and containing 10 cysteine amino acid residues.

In another aspect, the present invention is directed to a method of preparing and isolating a recombinant cDNA molecule encoding a recombinant protein exhibiting anticoagulant activity and having a NAP domain, and to a cDNA molecule made by this method. This method comprises the steps of: (a) isolating a cDNA library from a species of nematode; (b) ligating said cDNA library into a cloning vector; (c) introducing said cloning vector containing said CDNA library into a host cell; (d) contacting the CDNA molecules of said host cell with a solution containing a hybridization probe having a nucleic acid sequence comprising AAR GCi TAY CCi GAR TGY GGi GAR AAY GAR TGG [SEQ. ID. NO. 1], wherein R is A or G, Y is T or C, and i is inosine; (e) detecting a recombinant cDNA molecule which hybridizes to said probe; and (f) isolating said recombinant cDNA molecule.

In another aspect, the present invention is directed to method of making a recombinant protein which has anticoagulant activity and which includes a NAP domain and to recombinant proteins made by this method. This method comprises the steps of: (a) isolating a cDNA library from a species of nematode; (b) ligating said cDNA library into a cloning vector; (c) introducing said cloning vector containing said cDNA library into a first host cell; (d) contacting the cDNA molecules of said first host cell with a solution containing a hybridization probe having a nucleic acid sequence comprising AAR GCi TAY CCi GAR TGY GGi GAR AAY GAR TGG [SEQ. ID. NO. 1], wherein R is A or G, Y is T or C, and i is inosine; (e) detecting a recombinant cDNA molecule which hybridizes to said probe; (f) isolating said recombinant cDNA molecule; (g) ligating the nucleic acid sequence of said cDNA molecule which encodes said recombinant protein into an expression vector; (h) transforming a second host cell with said expression vector containing said nucleic acid sequence of said cDNA molecule which encodes said recombinant protein; (i) culturing the transformed second host cell; and (j) isolating said recombinant protein expressed by said second host cell. It is noted that when describing production of recombinant proteins in certain expression systems such as COS cells, the term "transfection" is conventionally used in place of (and sometimes interchangeably with) "transformation".

In another aspect, the present invention is directed to a method of making a recombinant cDNA encoding a recombinant protein having anticoagulant activity and having a NAP domain, comprising the steps of: (a) isolating a cDNA library from a nematode;(b) ligating said cDNA library into a cloning vector; (c) introducing said cloning vector containing said cDNA library into a host cell; (d) contacting the cDNA molecules of said host cells with a solution comprising first and second hybridization probes, wherein said first hybridization probe has the nucleic acid sequence comprising AAG GCA TAC CCG GAG TGT GGT GAG AAT GAA TGG CTC GAC GAC TGT GGA ACT CAG AAG CCA TGC GAG GCC AAG TGC AAT GAG GAA CCC CCT GAG GAG GAA GAT CCG ATA TGC CGC TCA CGT GGT TGT TTA TTA CCT CCT GCT TGC GTA TGC AAA GAC GGA TTC TAC AGA GAC ACG GTG ATC GGC GAC TGT GTT AGG GAA GAA GAA TGC GAC CAA CAT GAG ATT ATA CAT GTC TGA [SEQ. ID. NO. 2], and said second hybridization probe has the nucleic acid sequence comprising AAG GCA TAC CCG GAG TGT GGT GAG AAT GAA TGG CTC GAC GTC TGT GGA ACT AAG AAG CCA TGC GAG GCC AAG TGC AGT GAG GAA GAG GAG GAA GAT CCG ATA TGC CGA TCA TTT TCT TGT CCG GGT CCC GCT GCT TGC GTA TGC GAA GAC GGA TTC TAC AGA GAC ACG GTG ATC GGC GAC TGT GTT AAG GAA GAA GAA TGC GAC CAA CAT GAG ATT ATA CAT GTC TGA [SEQ. ID. NO. 3]; (e) detecting a recombinant CDNA molecule which hybridizes to said mixture of said probes; and (f) isolating said recombinant cDNA molecule.

In yet another aspect, the present invention is directed to a method of making a recombinant cDNA encoding a protein having anticoagulant activity and which encodes a NAP domain, comprising the steps of: (a) isolating a cDNA library from a nematode; (b) ligating said cDNA library into a phagemid vector; (c) transforming host cells with said vector containing said cDNA library; (d) culturing said host cells; (e) infecting said host cells with a helper phage; (f) separating phage containing said cDNA library from said host cells; (g) combining a solution of said phage containing said cDNA library with a solution of biotinylated human factor X$a$; (h) contacting a streptavidin-coated solid phase with said solution containing said phages containing said cDNA library, and said biotinylated human factor X$a$; (i) isolating phages which bind to said streptavidin-coated solid phase, and (j) isolating the recombinant cDNA molecule from phages which bind to said streptavidin-coated solid phase.

In one preferred aspect, the present invention is directed to a recombinant cDNA having a nucleic acid sequence selected from the nucleic acid sequences depicted in FIG. 7A, FIG. 7B, FIG. 7C, FIG. 7D, FIG. 7E and FIG. 7F.

In an alternate preferred aspect, the present invention is directed to a recombinant cDNA having the nucleic acid sequence depicted in FIG. 9.

DEFINITIONS

The term "amino acid" refers to the natural L-amino acids. Natural L-amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val).

The term "amino acid residue" refers to radicals having the structure: (1) —NH—CH(R)C(=O)—, wherein R is the alpha-carbon side-chain group of an L-amino acid, except for L-proline; or (2)

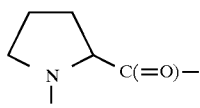

for L-proline.

The term "peptide" refers to a sequence of amino acids linked together through their alpha-amino and carboxylate groups by peptide bonds. Such sequences as shown herein are presented in the amino to carboxy direction, from left to right.

The term "protein" refers to a molecule comprised of one or more peptides.

The term "cDNA" refers to complementary DNA.

The term "nucleic acid" refers to polymers in which bases (e.g., purines or pyrimidines) are attached to a sugar phosphate backbone. Nucleic acids include DNA and RNA.

The term "nucleic acid sequence" refers to the sequence of nucleosides comprising a nucleic acid. Such sequences as shown herein are presented in the 5' to 3' direction, from left to right.

The term "recombinant DNA molecule" refers to a DNA molecule created by ligating together pieces of DNA that are not normally continguous.

The term "mRNA" refers to messenger ribonucleic acid.

The term "homology" refers to the degree of similarity of DNA or peptide sequences.

BRIEF DESCRIPTION OF THE DRAWINGS

FIG. 1 depicts the nucleotide sequence of the NAP5 cDNA [SEQ. ID. NO. 32]. The numbering starts at the first nucleotide of the cDNA. Translation starts at the first ATG codon (position 14); a second in frame ATG is present at position 20.

FIG. 2 depicts the amino acid sequence of mature NAP isoform 5 [SEQ. ID. NO. 33].

FIG. 3 depicts the nucleotide sequence of the NAP6 CDNA [SEQ. ID. NO. 34]. The numbering starts at the first nucleotide of the CDNA. Translation starts at the first ATG codon (position 14); a second in frame ATG is present at position 20.

FIG. 4 depicts the amino acid sequence of mature NAP isoform 6 [SEQ. ID. NO. 35]. Amino acids that differ from NAP isoform 5 are underlined. In addition to these amino acid substitutions, NAP isoform 6 contains a two amino acid deletion (Pro-Pro) when compared to NAP isoform 5.

FIG. 5 depicts the amino acid sequence of Pro-NAP isoform 5 [SEQ. ID. NO. 36].

FIG. 6 depicts the amino acid sequence of Pro-NAP isoform 6 [SEQ. ID. NO. 37]. Amino acids that differ from Pro-NAP isoform 5 are underlined. In addition to these amino acid substitutions, Pro-NAP isoform 6 contains a two amino acid deletion (Pro-Pro) when compared to Pro-NAP isoform 5.

FIGS. 7A-1 through 7F depict the nucleotide sequences of the cDNAs and deduced amino acid sequences of certain NAP proteins isolated from *Ancylostoma ceylanicum, Ancylostoma duodenale*, and *Heligmosomoides polygryrus*. FIGS. 7A-1 to 7A-2 depict sequences for the recombinant cDNA molecule, AceNAP4, isolated from *Ancylostoma ceylanicum* [SEQ. ID. NO. 38]. FIG. 7B depicts sequences for the recombinant cDNA molecule, AceNAP5, isolated from *Ancylostoma ceylanicum* [SEQ. ID. NO. 39]. FIG. 7C depicts sequences for the recombinant cDNA molecule, AceNAP7, isolated from *Ancylostom ceylanicum* [SEQ. ID. NO. 40]. FIG. 7D depicts sequences for the recombinanct CDNA molecule, AduNAP4, isolated from *Ancylostoma duodenale* [SEQ. ID. NO. 41]. FIGS. 7E-1 to 7E-2 depict sequences for the recombinant cDNA molecule, AduNAP7, isolated from *Ancylostoma duodenale* [SEQ. ID. NO. 42]. FIG. 7F depicts sequences for the recombinant cDNA molecule, HpoNAP5, isolated from *Heligmosomoides polygyrus* [SEQ. ID. NO. 43]. The EcoRI site, corresponding to the 5'-end of the recombinant cDNA molecule, is indicated in all cases (underlined). Numbering of each sequence starts at this EcoRI site. AceNAP4 and AduNAP7, each encode a protein which has two NAP domains; all other clones code for a protein having a single NAP domain. The AduNAP4 cDNA clone is not full-length, i.e., the recombinant cDNA molecule lacks the 5'-terminal part of the coding region based on comparison with other isoforms.

FIGS. 8A through 8C depict the nucleotide sequence of the vectors, pDONG61 (FIG. 8A) [SEQ. ID. NO. 44], pDONG62 (FIG. 8B) [SEQ. ID. NO. 45], and pDONG63 (FIG. 8C) [SEQ. ID. NO. 46]. The HindIII-BamHI fragment which is shown is located between the HindIII and BamHI sites of pUC119. The vectors allow the cloning of cDNAs, as SfiI-NotI fragments, in the three different reading frames downstream of the filamentous phage gene 6. All relevant restriction sites are indicated. The AAA Lys-triplet at position 373–375 is the last codon of gene 6. The gene 6 encoded protein is followed by a Gly-Gly-Gly-Ser-Gly-Gly [SEQ. ID. NO. 4] linker sequence.

FIG. 9 depicts the nucleotide sequence of the recombinant CDNA molecule, NAPc2 cDNA [SEQ. ID. NO. 47]. The EcoRI site, corresponding to the 5'-end of the cDNA, is indicated (underlined). Numbering starts at this EcoRI site. The deduced amino acid sequence is also shown; the translational reading frame was determined by the gene 6 fusion partner. The NAPc2 cDNA lacks the 5'-terminal part of the coding region; the homology with the NAP isoforms 5 and 6 predicts that the first seven amino acid residues belong to the secretion signal.

FIGS. 11-1 to 11-9 depict the alignment of the amino acid sequences encoded by NAP cDNAs isolated from various nematodes. NAP5 [SEQ. ID. NO. 48], NAP6 [SEQ. ID. NO. 49], and NAPc2 [SEQ. ID. NO. 50] were isolated from *Ancylostoma caninum*. AceNAP5 [SEQ. ID. NO. 51], AceNAP7 [SEQ. ID. NO. 52], and AceNAP4 [SEQ. ID. NOS. 53 and 54] were isolated from *Ancylostoma ceylanicum*. AduNAP4 [SEQ. ID. NO. 55] and AduNAP7 [SEQ. ID. NOS. 56 and 57] were isolated from *Ancylostoma duodenale*. HpoNAP5 [SEQ. ID. NO. 58] was isolated from *Heligmosomoides polygrus*. The amino acid sequences shown in this figure are as given in FIGS. 1, 3, 7A-1 through 7F, and 9. The sequences of mature NAP isoforms 5 and 6 (see FIGS. 2 and 4) are characterized by ten cysteine residues (numbered one through ten and shown in bold). The region comprising these ten cysteines defines a NAP-domain. In addition to NAP5 and NAP6, all other derived amino acid sequences shown have at least one such NAP-domain. All of these amino acid sequences contain at least one NAP domain. The AceNAP4 cDNA consists of two adjacent regions, named AceNAP4d1 [SEQ. ID. NO. 53] and AceNAP4d2 [SEQ. ID NO. 54], which encode a first (d1) and second (d2) NAP domain; similarly, the AduNAP7 cDNA contains two adjacent regions, AduNAP7d1 [SEQ. ID. NO. 56] and AduNAP7d2 [SEQ. ID. NO. 57], encoding a first (d1) and second (d2) NAP-domain. The alignment of the amino acid sequences of all NAP-domains is guided by the cysteines; dashes (- - -) were introduced at certain positions to maintain the cysteine alignment and indicate the absence of an amino acid at that position. The carboxy-terminal residue of a cDNA encoded protein is followed by the word "end".

FIG. 12, Part B, depicts the following contiguous DNA sequences which are incorporated in pYAM7SP8: the acid phosphatase (PH01) secretion signal sequence, pro sequence and multicloning site (MCS) sequence. The ATG start codon of the PH01 secretion signal is underlined.

DETAILED DESCRIPTION OF THE INVENTION

Figure 10A:
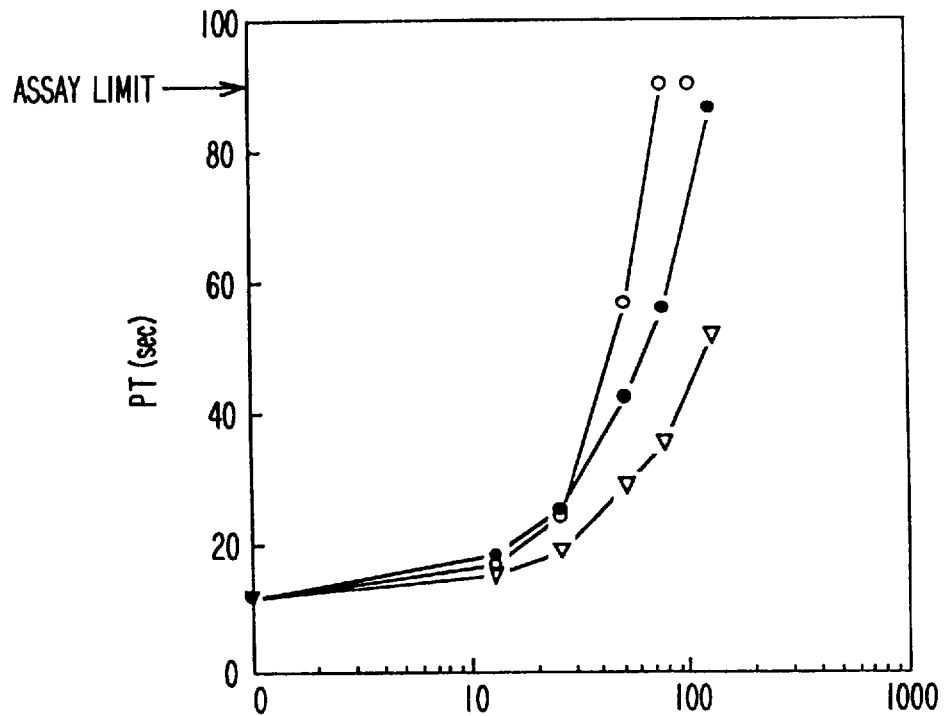
FIGS. 10A and 10B depict the comparative effects of NAP proteins on the prothrombin time (PT) measurement (FIG. 10A) and the activated partial thromboplastin time (aPTT) (FIG. 10B) of normal citrated human plasma. Solid circles, (●), represent Pro-NAP isoform 5; open triangles, (∇), represent NAP isoform 5; and open circles, (○), represent native NAP.

This invention provides a family of proteins, collectively referred to as Nematode-extracted Anticoagulant Proteins (NAPs). These proteins are so designated because the first member originally isolated was extracted from a nematode, the canine hookworm, *Ancyclostoma caninum*. However, the designation NAP or NAP domain should not be considered to limit the proteins of the present invention by this or other natural source.

Individual NAP proteins are characterized by having at least one NAP domain and by having anticoagulant activity. Such anticoagulant activity may be assessed by increases in clotting time in both the PT and aPTT assays described herein. The NAP domain is an amino acid sequence. It is believed that the NAP domain is responsible for the observed anticoagulant activity. Certain representative NAP domains include the amino acid sequences depicted in FIG. 11, particularly the sequences between the cysteines designated as Cysteine 1 and Cysteine 10 in FIG. 11. The characteristics broadly defining this family of proteins, as well as the nucleic acid molecules, including mRNAs sequences and DNA sequences which encode such proteins, are provided. Methods of making these proteins, as well as methods of making nucleic acid molecules encoding such proteins, are also provided. The specific examples provided are exemplary only and other members of the NAP family of proteins, as well as nucleic acid sequences encoding them, can be obtained by following the procedures outlined in these examples and described in herein.

The proteins of the present invention include isolated NAPs which comprise proteins having anticoagulant activity and including at least one NAP domain.

With respect to "anticoagulant activity", the purified proteins of the present invention are active as anticoagulants, and as such, are characterized by inhibiting the clotting of blood which includes the clotting of plasma. In one aspect, the preferred isolated proteins of the present invention include those which increase the clotting time of human plasma as measured in both the prothrombin time (PT) and activated partial thromboplastin time (aPTT) assays.

In the PT assay, clotting is initiated by the addition of a fixed amount of tissue factor-phospholipid micelle complex (thromboplastin) to human plasma. Substances acting as anticoagulants interfere with certain interactions on the surface of this complex and increase the time required to achieve a certain amount of clotting relative to the clotting observed in the absence of the anticoagulant. In the APTT assay, clotting is initiated by the addition of a certain fixed amount of negatively charged phospholipid micelle (activator) to the human plasma. Substances acting as anticoagulants will interfere with certain interactions on the surface of the complex and again increase the time to achieve a certain amount of clotting relative to that observed in the absence of the anticoagulant. Example B describes an example of such PT and APTT assays. These assays can be used to assess anticoagulant activity of the isolated NAPs of the present invention.

The preferred isolated NAPs of the present invention include those which double the clotting time of human plasma in the PT assay when present at a concentration of about 1 to about 500 nanomolar and which also double the clotting time of human plasma in the aPTT assay when present at a concentration of about 1 to about 500 nanomolar. Especially preferably are those proteins which double the clotting time of human plasma in the PT assay when present at a concentration of about 5 to about 100 nanomolar, and which also double the clotting time of human plasma in the aPTT assay when present at a concentration of about 5 to about 200 nanomolar. More especially preferred are those proteins which double the clotting time of human plasma in the PT assay when present at a concentration about 10 to about 50 nanomolar, and which also double the clotting time of human plasma in the aPTT assay when present at a concentration of about 10 to about 100 nanomolar.

With respect to "NAP domain", the isolated proteins (or NAPs) of the present invention include at least one NAP domain in their amino acid sequence. Certain NAP domains have an amino acid sequence having a molecular weight of about 5.0 to 8.0 kilodaltons and containing 10 cysteine amino acid residues.

Certain preferred isolated NAPs of the present invention include those which contain at least one NAP domain, wherein each such NAP domain is further characterized by including the amino acid sequence: Cys-$A_1$-Cys-$A_2$-Cys-$A_3$-Cys-$A_4$-Cys-$A_5$-Cys-$A_6$-Cys-$A_7$-Cys-$A_8$-Cys-$A_9$-Cys, wherein: (a) $A_1$ is an amino acid sequence containing 7 to 8 amino acid residues; (b) $A_2$ is an amino acid sequence containing 2 to 5 amino acid residues; (c) $A_3$ is an amino acid sequence containing 3 amino acid residues; (d) $A_4$ is an amino acid sequence containing 6 to 17 amino acid residues; (e) $A_5$ is an amino acid sequence containing 3 to 4 amino acid residues; (f) $A_6$ is an amino acid sequence containing 3 to 5 amino acid residues; (g) $A_7$ is an amino acid residue; (h) $A_8$ is an amino acid sequence containing 10 to 12 amino acid residues; and (i) $A_9$ is an amino acid sequence containing 5 to 6 amino acid residues. Especially preferred NAP domains include those wherein $A_2$ is an amino acid sequence containing 4 to 5 amino acid residues and $A_4$ is an amino acid sequence containing 6 to 16 amino acid residues. More preferred are NAP domains, wherein: (a) $A_1$ has Glu as its fourth amino acid residue; (b) $A_2$ has Gly as its first amino acid residue; (c) $A_8$ has Gly as its third amino acid residue and Arg as its sixth amino acid residue; and (d) $A_9$ has Val as its first amino acid residue. More preferably, $A_3$ has Asp or Glu as its first amino acid residue and Lys or Arg as its third amino acid residue and $A_7$ is Val or Gln. Also, more preferably $A_8$ has Leu or Phe as its fourth amino acid residue and Lys or Tyr as its fifth amino acid residue. Also preferred are NAP domains where, when $A_8$ has 11 or 12 amino acid residues, Asp or Gly is its penultimate amino acid residue, and, where when $A_8$ has 10 amino acids, Gly is its tenth amino acid residue. For expression of recombinant protein in certain expression systems, a recombinant NAP may additionally include an amino acid sequence for an appropriate secretion signal. Certain representative NAP domains include the sequences depicted in FIG. 11, particularly the sequences between (and including) the cysteines designated as Cysteine 1 and Cysteine 10.

The isolated NAPs of the present invention include those having variations in the disclosed amino acid sequence or sequences, including fragments, naturally occurring mutations, allelic variants, randomly generated artificial mutants and intentional sequence variations, all of which conserve anticoagulant activity. The term "fragments" refers to any part of the sequence which contains fewer amino acids than the complete protein, as for example, partial sequences excluding portions at the amino-terminus, carboxy-terminus or between the aminoterminus and carboxy-terminus of the complete protein.

The isolated NAPs of the present invention also include proteins having a recombinant amino acid sequence or sequences which conserve the anticoagulant activity of the NAP domain amino acid sequence or sequences. These recombinant proteins include hybrid proteins, such as fusion proteins, proteins resulting from the expression of multiple genes within the expression vector, proteins resulting from expression of multiple genes within the chromosome of the host cell, and may include a polypeptide having anticoagulant activity of a disclosed protein linked by peptide bonds to a second polypeptide. The recombinant proteins also include variants of the NAP domain amino acid sequence or sequences of the present invention that differ only by conservative amino acid substitution. Conservative amino acid substitutions are defined as "sets" in Table I of Taylor, W. R., J. Mol. Biol., 188:233 (1986). The recombinant proteins also include variants of the disclosed isolated NAP domain amino acid sequence or sequences of the present invention in which amino acid substitutions or deletions are made which conserve the anticoagulant activity of the isolated NAP domain sequence or sequences.

One preferred embodiment of the present invention is a protein isolated by biochemical methods from the nematode, *Ancylostoma caninum*, as described in Example 1. This protein increases the clotting time of human plasma in the PT and aPTT assays, contains one NAP domain, and is characterized by an N-terminus having the amino acid sequence, Lys-Ala-Tyr-Pro-Glu-Cys-Gly-Glu-Asn-Glu-Trp-Leu-Asp [SEQ. ID. NO. 6], and a molecular weight of about 8.7 kilodaltons to about 8.8 kilodaltons as determined by mass spectrometry.

Further preferred embodiments of the present invention include the proteins having anticoagulant activity made by recombinant methods from the cDNA library isolated from the nematode, *Ancylostoma caninum*, for example, NAP isoform 5, NAP isoform 6, Pro-NAP isoform 5 and Pro-NAP isoform 6, the amino acids sequences of which are shown in FIG. 2, FIG. 4, FIG. 5 and FIG. 6, respectively. Each such preferred embodiment increases the clotting time of human plasma in the PT and aPTT assays and contains one NAP domain. Each is further characterized by an amino acid sequence which includes the amino acid sequence, Lys-Ala-Tyr-Pro-Glu-Cys-Gly-Glu-Asn-Glu-Trp-Leu-Asp [SEQ. ID. NO. 6].

With respect to "isolated proteins", the proteins of the present invention are isolated by methods of protein purification well known in the art, or as disclosed below. They may be isolated from a natural source, from a chemical mixture after chemical synthesis on a solid phase or in solution such as solid-phase automated peptide synthesis, or from a cell culture after production by recombinant methods.

1. NAP Isolated From Natural Sources

The preferred isolated proteins (NAPs) of the present invention may be isolated and purified from natural sources. Preferred as natural sources are nematodes; suitable nematodes include intestinal nematodes such as *Ancylostoma caninum, Ancylostoma ceylanicum, Ancylostoma duodenale, Necator americanus* and *Heligmosomoides polygyrus*. Especially preferred as a natural source is the nematode, the dog hookworm, *Ancylostoma caninum*.

The preferred proteins of the present invention are isolated and purified from their natural sources by methods known in the biochemical arts. These methods include preparing a soluble extract and enriching the extract using chromatographic methods on different solid support matrices. Preferred methods of purification would include preparation of a soluble extract of a nematode in 0.02M Tris-HCl, pH 7.4 buffer containing various protease inhibitors, followed by sequential chromatography of the extract through columns containing Concanvalin-A Sepharose matrix, Poros20 HQ cation-ion exchange matrix, Superdex30 gel filtration matrix and a C18 reverse-phase matrix. The fractions collected from such chromatography columns may be selected by their ability to increase the clotting time of human plasma, as measured by the PT and aPTT assays, or their ability to inhibit factor Xa amidolytic activity as measured in a calorimetric amidolytic assay using purified enzyme. An example of a preferred method of purification of an isolated protein of the present invention would include that as disclosed in Example 1.

The preferred proteins of the present invention, when purified from the natural source, *Ancylostoma caninum*, as described, include those which contain the amino acid sequence: Lys-Ala-Tyr-Pro-Glu-Cys-Gly-Glu-Asn-Glu-Trp-Leu-Asp [SEQ. ID. NO. 6]. Especially preferred are the purified proteins having this amino acid sequence at its amino terminus. More especially preferred are purified proteins having the amino acid sequences shown in FIG. 2 (NAP isoform 5) or FIG. 4 (NAP isoform 6). One preferred protein of the present invention was demonstrated to have the amino acid sequence, Lys-Ala-Tyr-Pro-Glu-Cys-Gly-Glu-Asn-Glu-Trp-Leu-Asp [SEQ. ID. NO. 6] at its aminoterminus and a molecular weight of 8.7 to 8.8 kilodaltons, as determined by mass spectrometry.

2. NAP Made by Chemical Synthesis

The preferred isolated NAPs of the present invention may be synthesized by standard methods known in the chemical arts.

The isolated proteins of the present invention may be prepared using solid-phase synthesis, such as that described by Merrifield, J. Amer. Chem. Soc., 85:2149 (1964) or other equivalent methods known in the chemical arts, such as the method described by Houghten in Proc. Natl. Acad. Sci., 82:5132 (1985).

Solid-phase synthesis is commenced from the C-terminus of the peptide by coupling a protected amino acid or peptide to a suitable insoluble resin. Suitable resins include those containing chloromethyl, bromomethyl, hydroxylmethyl, aminomethyl, benzhydryl, and t-alkyloxycarbonylhydrazide groups to which the amino acid can be directly coupled.

In this solid phase synthesis, the carboxy terminal amino acid, having its alpha amino group and, if necessary, its reactive side chain group suitably protected, is first coupled to the insoluble resin. After removal of the alpha amino protecting group, such as by treatment with trifluoroacetic acid in a suitable solvent, the next amino acid or peptide, also having its alpha amino group and, if necessary, any reactive side chain group or groups suitably protected, is coupled to the free alpha amino group of the amino acid coupled to the resin. Additional suitably protected amino acids or peptides are coupled in the same manner to the growing peptide chain until the desired amino acid sequence is achieved. The synthesis may be done manually, by using automated peptide synthesizers, or by a combination of these.

The coupling of the suitably protected amino acid or peptide to the free alpha amino group of the resin-bound amino acid can be carried out according to conventional coupling methods, such as the azide method, mixed anhydride method, DCC (dicyclohexylcarbodiimide) method, activated ester method (p-nitrophenyl ester or N-hydroxysuccinimide ester), BOP (benzotriazole-1-yl-oxy-tris (diamino) phosphonium hexafluorophosphate) method or Woodward reagent K method.

It is common in peptide synthesis that the protecting groups for the alpha amino group of the amino acids or peptides coupled to the growing peptide chain attached to the insoluble resin will be removed under conditions which do not remove the side chain protecting groups. Upon completion of the synthesis, it is also common that the peptide is removed from the insoluble resin, and during or after such removal, the side chain protecting groups are removed.

Suitable protecting groups for the alpha amino group of all amino acids and the omega amino group of lysine include benzyloxycarbonyl, isonicotinyloxycarbonyl, o-chlorobenzyloxycarbonyl, p-nitrophenyloxycarbonyl, p-methoxyphenyloxycarbonyl, t-butoxycarbonyl, t-amyloxycarbonyl, adamantyloxycarbonyl, 2-(4-biphenyl)-2-propyloxycarbonyl, 9-fluorenylmethoxycarbonyl, methylsulfonylethoxylcarbonyl, trifluroacetyl, phthalyl, formyl, 2-nitrophenylsulfphenyl, diphenylphosphinothioyl, dimethylphosphinothioyl, and the like.

Suitable protecting groups for the carboxy group of aspartic acid and glutamic acid include benzyl ester, cyclohexyl ester, 4-nitrobenzyl ester, t-butyl ester, 4-pyridylmethyl ester, and the like.

Suitable protecting groups for the guanidino group of arginine include nitro, p-toluenesulfonyl, benzyloxycarbonyl, adamantyloxycarbonyl, p-methoxybenzenesulfonyl, 4-methoxy-2,6-dimethylbenzenesulfonyl, 1,3,5-trimethylphenylsulfonyl, and the like.

Suitable protecting groups for the thiol group of cysteine include p-methoxybenzyl, triphenylmethyl, acetylaminomethyl, ethylcarbamoyl, 4-methylbenzyl, 2,4,6-trimethylbenzyl, and the like.

Suitable protecting groups for the hydroxy group of serine include benzyl, t-butyl, acetyl, tetrahydropyranyl, and the like.

The completed peptide may be cleaved from the resin by treatment with liquid hydrofluoric acid containing one or more thio-containing scavengers at reduced temperatures. The cleavage of the peptide from the resin by such treatment will also remove all side chain protecting groups from the peptide.

The cleaved peptide is dissolved in dilute acetic acid followed by filtration, then is allowed to refold and establish proper disulfide bond formation by dilution to a peptide concentration of about 0.5 mM to about 2 mM in a 0.1M acetic acid solution. The pH of this solution is adjusted to about 8.0 using ammonium hydroxide and the solution is stirred open to air for about 24 to about 72 hours.

The refolded peptide is purified by chromatography, preferably by high pressure liquid chromatography on a reverse phase column, eluting with gradient of acetonitrile in water (also containing 0.1% trifluoroacetic acid), with the preferred gradient running from 0 to about 80% acetonitrile in water. Upon collection of fractions containing the pure peptide, the fractions are pooled and lyophilized to the solid peptide.

3. NAP Made By Recombinant Methods

Alternatively, the preferred isolated NAPs the present invention may be made by recombinant DNA methods well known in the biological arts. Sambrook, J., Fritsch, E. F. and Maniatis, T., *Molecular Cloning, A Laboratory Manual, Second Edition*, volumes 1 to 3, Cold Spring Harbor Laboratory Press (1989).

Recombinant DNA methods allow segments of genetic information, DNA, from different organisms, to be joined together outside of the organisms from which the DNA was obtained and this hybrid DNA to be incorporated into a cell that will allow the production of the protein for which the original DNA encodes.

Genetic information encoding a protein of the present invention may be obtained from the genomic DNA or mRNA of an organism by methods well known in the art. Preferred methods of obtaining this genetic information include isolating mRNA from an organism, converting it to its complementary DNA (cDNA), incorporating the cDNA into an appropriate cloning vector, and identifying the clone which contains the recombinant cDNA encoding the desired protein by means of hybridization with appropriate oligonucleotide probes constructed from known sequences of the protein.

The genetic information in the recombinant cDNA encoding a protein of the present invention may be ligated into an expression vector, the vector introduced into host cells, and the genetic information expressed as the protein encoded for.

(A) Preparation of cDNA Library.

Preferred natural sources of mRNA from which to construct a cDNA library are nematodes which include intestinal nematodes such as *Ancylostoma caninum, Ancylostoma ceylanicum, Ancylostoma duodenale, Necator americanus* and *Heligmosomoides polygyrus*. Especially preferred as a natural source of mRNA is the nematode, *Ancylostoma caninum*.

Preferred methods of isolating mRNA encoding a protein of the present invention, along with other mRNA, from an organism include chromatography on poly U or poly T affinity gels. Especially preferred methods of isolating the mRNA from nematodes include the procedure and materials provided in the QuickPrep mRNA Purification kit (Pharmacia).

Preferred methods of obtaining double-stranded cDNA from isolated mRNA include synthesizing a single-stranded cDNA on the mRNA template using a reverse transcriptase, degrading the RNA hybridized to the cDNA strand using a ribonuclease (RNase), and synthesizing a complementary DNA strand by using a DNA polymerase to give a double-stranded cDNA. Especially preferred methods include those wherein about 3 micrograms of mRNA isolated from a nematode is converted into double-stranded cDNA making use of Avian Myeloblastosis Virus reverse transcriptase, RNase H, and *E. coli* DNA polymerase and T4 DNA polymerase.

cDNA encoding a protein of the present invention, along with the other cDNA in the library constructed as above, are then ligated into cloning vectors. Cloning vectors include a DNA sequence which accommodates the cDNA from the cDNA library. The vectors containing the cDNA library are introduced into host cells that can exist in a stable manner and provide a environment in which the cloning vector is replicated. Suitable cloning vectors include plasmids, bacteriophages, viruses and cosmids. Preferred cloning vectors include the bacteriophages. Cloning vectors which are especially preferred include the bacteriophage, lambda gt11 Sfi-Not vector.

The construction of suitable cloning vectors containing the cDNA library and control sequences employs standard ligation and restriction techniques which are well known in the art. Isolated plasmids, DNA sequences or synthesized oligonucleotides are cleaved, tailored and religated in the form desired.

With respect to restriction techniques, site-specific cleavage of cDNA is performed by treating with suitable restriction enzyme under conditions which are generally understood in the art, and the particulars of which are specified by the manufacturer of these commercially available restriction enzymes. For example, see the product catalogs of New England Biolabs, Promega and Stratagene Cloning Systems.

Generally, about 1 microgram of the cDNA is cleaved by treatment in about one unit of a restriction enzyme in about 20 microliters of buffer solution. Typically, an excess of restriction enzyme is used to ensure complete cleavage of the cDNA. Incubation times of about 1 to 2 hours at about 37° C. are usually used, though exceptions are known. After each cleavage reaction, the protein may be removed by extraction with phenol/chloroform, optionally followed by chromatography over a gel filtration column, such as Sephadex® G50. Alternatively, cleaved cDNA fragments may be separated by their sizes by electrophoresis in polyacrylamide or agarose gels and isolated using standard techniques. A general description of size separations is found in methods of Enzymology, 65:499–560 (1980).

The restriction enzyme-cleaved cDNA fragments are then ligated into a cloning vector.

With respect to ligation techniques, blunt-end legations are usually performed in about 15 to about 30 microliters of a pH 7.5 buffer comprising about 1 mM ATP and about 0.3 to 0.6 (Weiss) units of T4 DNA ligase at about 14° C. Intermolecular "sticky end" legations are usually performed at about 5 to 100 nanomolar total-end DNA concentrations. Intermolecular blunt-end ligations (usually employing about 10 to 30-fold molar excess of linkers) are performed at about 1 micromolar total-end DNA concentrations.

(B) Preparation of cDNA Encoding NAP.

Cloning vectors containing the cDNA library prepared as disclosed are introduced into host cells, the host cells are cultured, plated, and then probed with a hybridization probe to identify clones which contain the recombinant cDNA encoding a protein of the present invention. Preferred host cells include bacteria when phage cloning vectors are used. Especially preferred host cells include *E. coli* strains such as strain Y1090.

Alternatively, the recombinant cDNA encoding a protein of the present invention may be obtained by expression of such protein on the outer surface of a filamentous phage and then isolating such phage by binding them to a target protein involved in blood coagulation.

An important and well known feature of the genetic code is its redundancy—more than one triplet nucleotide sequence codes for one amino acid. Thus, a number of different nucleotide sequences are possible for recombinant cDNA molecules which encode a particular amino acid sequence for a NAP of the present invention. Such nucleotide sequences are considered functionally equivalent since they can result in the production of the same amino acid sequence in all organisms. Occasionally, a methylated variant of a purine or pyrimidine may be incorporated into a given nucleotide sequence. However, such methylations do not affect the coding relationship in any way.

(1) Using Oligonucleotide Probes.

Hybridization probes and primers are oligonucleotide sequences which are complementary to all or part of the recombinant cDNA molecule that is desired. They may be prepared using any suitable method, for example, the phosphotriester and phosphodiester methods, described respectively in Narang, S. A. et al., Methods in Enzymology, 68:90 (1979) and Brown, E. L. et al., Methods in Enzymology, 68:109 (1979), or automated embodiments thereof. In one such embodiment, diethylphosphoramidites are used as starting materials and may be synthesized as described by Beaucage et al, Tetrahedron Letters, 22:1859–1862 (1981). One method for synthesizing oligonucleotides on a modified solid support is described in U.S. Pat. No. 4,458,066. Probes differ from primers in that they are labelled with an enzyme, such as horseradish peroxidase, or radioactive atom, such as $^{32}$p, to facilitate their detection. A synthesized probe is radiolabeled by nick translation using E. coli DNA polymerase I or by end labeling using alkaline phosphatase and T4 bacteriophage polynucleotide kinase.

Preferred hybridization probes include oligonucleotide sequences which are complementary to a stretch of the single-stranded cDNA encoding a portion of the amino acid sequence of NAP purified from the nematode, the dog hookworm, Ancylostoma caninum. For example, a portion of the amino acid sequence shown in FIG. 2 (NAP isoform 5) or FIG. 4 (NAP isoform 6) can be used. Especially preferred hybridization probes include those wherein their oligonucleotide sequence is complementary to the stretch of the single-stranded cDNA encoding the amino acid sequence: Lys-Ala-Tyr-Pro-Glu-Cys-Gly-Glu-Asn-Glu-Trp [SEQ. ID. NO. 7]. Such hybridization probes include the degenerate probe having the oligonucleotide sequence: AAR GCi TAY CCi GAR TGY GGi GAR AAY GAR TGG [SEQ. ID. NO. 1], wherein R is A or G, Y is T or C, and i is inosine. A preferred recombinant cDNA molecule encoding a protein of the present invention is identified by its ability to hybridize to this probe.

Upon identification of the clone containing the desired cDNA, amplification is used to produce large quantities of a gene encoding a protein of the present invention in the form of a recombinant cDNA molecule.

Preferred methods of amplification include the use of the polymerase chain reaction (PCR). See, e.g., PCR Technology, W. H. Freeman and Company, New York (Edit. Erlich, H. A. 1992). PCR is an in vitro amplification method for the synthesis of specific DNA sequences. In PCR, two oligonucleotide primers that hybridize to opposite strands and flank the region of interest in the cDNA of the clone are used. A repetitive series of cycles involving cDNA denaturation into single strands, primer annealing to the single-stranded cDNA, and the extension of the annealed primers by DNA polymerase results in number of copies of cDNA, whose termini are defined by the 5-ends of the primers, approximately doubling at every cycle. Ibid., p.1. Through PCR amplification, the coding domain and any additional primer encoded information such as restriction sites or translational signals (signal sequences, start codons and/or stop codons) of the recombinant cDNA molecule to be isolated is obtained.

Preferred conditions for amplification of cDNA include those using Taq polymerase and involving 30 temperature cycles of: 1 minute at 95° C.; 1 minute at 50° C.; 1.5 minutes at 72° C. Preferred primers include the oligo(dT)-NotI primer, AATTCGCGGC CGC(T)$_{15}$ [SEQ. ID. NO. 8], obtained from Promega Corp. in combination with either (i) the degenerate primer having the oligonucleotide sequence: AAR GCi TAY CCi GAR TGY GGi GAR AAY GAR TGG [SEQ. ID. NO. 1], wherein R is A or G, Y is T or C, and i is inosine, or (ii) the lambda gt11 primer #1218, GGTGGC-GACG ACTCCTGGAG CCCG [SEQ. ID. NO. 9], obtained from New England Biolabs.

The nucleic acid sequence of a recombinant cDNA molecule made as disclosed is determined by the dideoxy method of Sanger, F. et al., Proc. Natl. Acad. Sci. USA, 74:5463 (1977) as further described by Messing, et al., Nucleic Acids Res., 9:309 (1981).

Preferred recombinant cDNA molecules made as disclosed include those having the nucleic acid sequences of FIG. 1 (NAP5 gene) and FIG. 3 (NAP6 gene).

(2) Using NAP cDNAs As Probes.

Preferred recombinant cDNA molecules made by the above method, but using as hybridization probes fragments derived from the NAP5 gene (FIG. 1) and the NAP6 gene (FIG. 2), include those having the nucleic acid sequences of FIGS. 7A, 7B, 7C, 7D, 7E or 7F.

Also especially preferred as hybridization probes are oligonucleotide sequences encoding substantially all of the amino acid sequence of NAP purified from the nematode, the dog hookworm, Ancylostoma caninum. Especially preferred probes include those having the nucleic acid sequences shown in FIG. 1 (NAP5 gene): AAG GCA TAC CCG GAG TGT GGT GAG AAT GAA TGG CTC GAC GAC TGT GGA ACT CAG AAG CCA TGC GAG GCC AAG TGC AAT GAG GAA CCC CCT GAG GAG GAA GAT CCG ATA TGC CGC TCA CGT GGT TGT TTA TTA CCT CCT GCT TGC GTA TGC AAA GAC GGA TTC TAC AGA GAC ACG GTG ATC GGC GAC TGT GTT AGG GAA GAA GAA TGC GAC CAA CAT GAG ATT ATA CAT GTC TGA [SEQ. ID. NO. 2], or FIG. 3 (NAP6 gene): AAG GCA TAC CCG GAG TGT GGT GAG AAT GAA TGG CTC GAC GTC TGT GGA ACT AAG AAG CCA TGC GAG GCC AAG TGC AGT GAG GAA GAG GAG GAA GAT CCG ATA TGC CGA TCA TTT TCT TGT CCG GGT CCC GCT GCT TGC GTA TGC GAA GAC GGA TTC TAC AGA GAC ACG GTG ATC GGC GAC TGT GTT AAG GAA GAA GAA TGC GAC CAA CAT GAG ATT ATA CAT GTC TGA [SEQ. ID. NO. 3].

(3) Using Phage Display.

Disclosed herein is a method to select cDNAs encoding the proteins of the present invention from whole CDNA libraries making use of filamentous phage display technology. Current display technology with filamentous phage relies on the in-frame insertion of coding regions of interest into gene 3 or gene 8 which code for the attachment protein and major coat protein of the phage, respectively. Those skilled in the art will recognize that various difficulties are inherent in performing this with a vast mixture of cDNAs of unknown sequence and that the most practical way to obtain functional display of cDNA products would consist of fusing the cDNAs through their 5'-end. Indeed, cDNA libraries of sufficient size may contain several cDNAs which derive from the same mRNA but which are 5'-terminally truncated at various positions such that some of them may be expressed as fusion products. A strategy along this line, which relies on the ability of the leucine zippers Jun and Fos to form heterodimers was recently described. See, Crameri, R. and Suter, M., Gene, 137:69–75 (1993).

We have found a novel alternative and direct way to convalently link cDNA gene products to the phage surface; the finding is based on the observation that proteins fused to the C-terminus of phage coat protein 6 can be functionally displayed. This observation has led to the development of a phagemid system as described herein which allows the expression of functionally displayed cDNA products, which in turn permits the affinity-selection of phage particles which contain the cDNA required for the production of the displayed cDNA product. This system provides the basis for the isolation of cDNAs which encode a protein of the present invention. Once isolated, recombinant cDNA molecules containing such cDNA can be used for expression of the proteins of the present invention in other expression systems. The recombinant cDNA molecules made in this way are considered to be within the scope of the present invention.

Recombinant cDNA molecules of the present invention are isolated by preparing a cDNA library from a natural source (as for example, a nematode such as a hookworm), ligating this cDNA library into appropriate phagemid vectors, transforming host cells with these vectors containing the cDNAs, culturing the host cells, infecting the transformed cells with an appropriate helper phage, separating phage from the host cell culture, separating phage expressing a protein of the present invention on its surface, isolating these phage, and isolating a recombinant cDNA molecule from such phage.

The phagemid vectors are constructed using the pUC119 expression vector described by Vieira, J. and Messing, J., Methods in Enzymology, 153:3–11 (1987). The filamentous phage gene 6 encoding a surface protein of the phage is modified on its 5' and 3' ends by the addition of HindIII and SfiI restriction sites, respectively, by use of three forward primers and one backward primer using PCR. This results in three DNA fragments which are further modified by addition to their 3' ends of NotI and BamHI restriction sites by PCR. After separate digestion of the three DNA fragments with HindIII and BamHI, the three DNA fragments are ligated into the pUC119 to give pDONG61, pDONG62 and pDONG63 expression vectors. These vectors permit the insertion of cDNA as SfiI-NotI fragments into them.

cDNA libraries are prepared from natural sources, such as nematodes, as described in Example 2. Preferred nematodes from which to make such libraries include the intestinal nematodes such as *Ancylostoma caninum, Ancylostoma ceylanicum, Ancylostoma duodenale, Necator arnericanus* and *Heligmosomoides polygyrus*.

A cDNA library as SfiI-NotI fragments may be directly directionally ligated into the phagemid vectors pDONG61, pDONG62 and pDONG63. Alternatively, a cDNA library which has been ligated into the lambda gt11 phage vector as described in Example 2 can be recovered by PCR, followed by isolation with electrophoresis and then directional ligation into these vectors. In the latter approach, preferred conditions for PCR use Taq polymerase; the primers, lambda gt11 primer #1218 having the sequence GGTGGCGACG ACTCCTGGAG CCCG [SEQ. ID. NO. 9] (New England Biolabs, Beverly, Mass., USA) and the oligo(dT)-NotI primer having the sequence, AATTCGCGGC CGC(T)$_{15}$ [SEQ. ID. NO. 8] (Promega Corp.); and 20 temperature cycles of 1 minute at 95° C., 1 minute at 50° C., and 3 minutes at 72° C., followed by 10 minutes at 65° C.

Host cells are transformed with the pDONG expression vectors containing a cDNA library. Preferred host cells include *E. coli* strains, with strain TG1 being especially preferred. Preferred methods for the transformation of *E. coli* host cells include electroporation.

The transformed cells are cultured at 37° C. in LB medium supplemented with 1% glucose and 100 micrograms/ml carbenicillin until the optical absorbance at 600 nm reaches the value of 0.5 and then are infected with VCSM13 helper phage (Stratagene) at a multiplicity of infection (moi) of 20.

The phage are separated from the culture by centrifugation, then are purified by precipitations with polyethylene glycol/sodium chloride.

The phage which express a NAP of the present invention on their surface are isolated by taking advantage of the ability of the NAP to bind to a target protein involved in blood coagulation, for example, Factor X*a*.

Preferred methods of isolating such phage include a method comprising the steps of:

(1) combining a solution of factor X*a* labelled to biotin with a solution of such phage;
(2) incubating this mixture;
(3) contacting a solid phase labelled with streptavidin with this mixture;
(4) incubating the solid phase with the mixture;
(5) removing the solid phase from the mixture and contacting the solid phase with buffer to remove unbound phage;
(6) contacting the solid phase with a second buffer to remove the bound phage from the solid phase;
(7) isolating such phage;
(8) transforming host cells with such phage;
(9) culturing the transformed host cells;
(10) infecting transformed host cells with VCSM13 helper phage;
(11) isolating the phage from the host cell culture; and
(12) repeating steps (1) to (11) four more times.

An especially preferred method of isolating such phage include the method as detailed in Example 10. Single-stranded DNA was prepared from the isolated phages and their inserts 3' to the filamentous phage gene 6 sequenced.

FIG. 9 depicts the recombinant cDNA molecule, NAPc2 [SEQ. ID. NO. 47], isolated by the phage display method. The deduced amino acid sequence of the protein of the present invention encoded by NAPc2 is also shown in this figure.

(C) Preparation of Recombinant NAP.

The recombinant cDNA molecules of the present invention when isolated as disclosed are used to obtain expression of the NAPs of the present invention. Generally, a recombinant cDNA molecule of the present invention is incorporated into an expression vector, this expression vector is introduced into an appropriate host cell, the host cell is cultured, and the expressed protein is isolated.

Expression vectors are DNA sequences that are required for the transcription of cloned copies of genes and translation of their mRNAs in an appropriate host. These vectors can express either procaryotic or eucaryotic genes in a variety of cells such as bacteria, yeast, mammalian, plant and insect cells. Proteins may also be expressed in a number of virus systems.

Suitably constructed expression vectors contain an origin of replication for autonomous replication in host cells, or are capable of integrating into the host cell chromosomes. Such vectors will also contain selective markers, a limited number of useful restriction enzyme sites, a high copy number, and strong promoters. Promoters are DNA sequences that direct RNA polymerase to bind to DNA and initiate RNA synthesis; strong promoters cause such initiation at high frequency. The preferred expression vectors of the present invention are operatively linked to a recombinant cDNA molecule of the present invention, i.e., the vectors are capable directing both replication of the attached recombinant cDNA molecule and expression of the protein encoded by the recombinant cDNA molecule. Expression vectors may include, but are not limited to cloning vectors, modified cloning vectors and specifically designed plasmids or viruses.

Suitable host cells for expression of the proteins of the present invention include bacteria, yeast, mammalian, plant and insect cells. With each type of cell and species therein certain expression vectors are appropriate as will be disclosed below.

Procaryotes may be used for expression of the proteins of the present invention. Suitable bacteria host cells include the various strains of *E. coli, Bacillus subtilis,* and various species of Pseudomonas. In these systems, plasmid vectors which contain replication sites and control sequences derived from species compatible with the host are used. Suitable vectors for *E. coli* are derivatives of pBR322, a plasmid derived from an *E. coli* species by Bolivar et al., Gene, 2:95 (1977). Common procaryotic control sequences, which are defined herein to include promoters for transcription, initiation, optionally with an operator, along with ribosome binding site sequences, include the beta-lactamase and lactose promoter systems (Chang et al., Nature, 198:1056 (1977)), the tryptophan promoter system (Goeddel et al., Nucleic Acids Res., 8:4057 (1980)) and the lambda-derived-$P_L$ promoter and N-gene ribosome binding site (Shimatake et al., Nature, 292:128 (1981)). However, any available promoter system compatible with procaryotes can be used. Preferred procaryote expression systems include *E. coli* and their expression vectors.

Eucaryotes may be used for expression of the proteins of the present invention. Eucaryotes are usually represented by the yeast and mammalian cells. Suitable yeast host cells include *Saccharomyces cerevisiae* and *Pichia pastoris*. Suitable mammalian host cells include COS and CHO (Chinese hamster ovary) cells.

Expression vectors for the eucaryotes are comprised of promoters derived from appropriate eucaryotic genes. Suitable promoters for yeast cell expression vectors, include promoters for synthesis of glycolytic enzymes, including those for 3-phosphoglycerate kinase gene in *Saccharomyces cerevisiae* (Hitzman et al., J. Biol. Chem., 255:2073 (1980)) and those for the metabolism of methanol as the alcohol oxidase gene in *Pichia pastoris* (Stroman et al., U.S. Pat. Nos. 4,808,537 and 4,855,231). Other suitable promoters include those from the enolase gene (Holland, M. J. et al., J. Biol. Chem., 256:1385 (1981)) or the Leu2 gene obtained from YEpl3 (Broach, J. et al., Gene, 8:121 (1978)). Preferred yeast expression systems include Pichia pastoris and their expression vectors.

Suitable promoters for mammalian cell expression vectors include the early and late promoters from SV40 (Fiers, et al., Nature, 273:113 (1978)) or other viral promoters such as those derived from polyoma, adenovirus II, bovine papilloma virus or avian sarcoma viruses. Suitable viral and mammalian enhancers may also be incorporated into these expression vectors.

Suitable promoters for plant cell expression vectors include the nopaline synthesis promoter described by Depicker, A. et al., Mol. Appl. Gen., 1:561 (1978).

Suitable promoters for insect cell expression vectors include modified versions of the system described by Smith et al., U.S Pat. No. 4,745,051. The expression vector comprises a baculovirus polyhedrin promoter under whose control a cDNA molecule encoding a protein can be placed.

Host cells are transformed by introduction of expression vectors of the present invention into them. Transformation is done using standard techniques appropriate for each type of cell. The calcium treatment employing calcium chloride described in Cohen, S. N., Proc. Natl. Acad. Sci. USA, 69:2110 (1972), or the RbCl method described in Maniatis et al., *Molecular Cloning: A Laboratory Manual*, p. 254, Cold Spring Harbor Press (1982) is used for procaryotes or other cells which contain substantial cell wall barriers. The transformation of yeast is carried out as described in Van Solingen, P. et al., J. Bacter., 130:946 (1977) and Hsiao, C.L. et al., Proc. Natl. Acad. Sci. USA, 76:3829 (1979). Mammalian cells without much cell wall are transformed using the calcium phosphate procedure of Graham and van der Eb, Virology, 52:546 (1978). Plant cells are transformed by infection with *Agrobacterium tumefaciens* as described in Shaw, C. et al., Gene, 23:315 (1983). Preferred methods of transforming *E. coli* and *Pichia pastoris* with expression vectors include electroporation.

Transformed host cells are cultured under conditions, such as type of media, temperature, oxygen content, fluid motion, etc., well known in the biological arts.

The recombinant proteins of the present invention are isolated from the host cell or media by standard methods well known in the biochemical arts, which include the use chromatography methods. Preferred methods of purification would include sequential chromatography of an extract through columns containing Poros20 HQ anion-ion exchange matrix or Poros20 HS cation exchange matrix, Superdex3O gel filtration matrix and a C18 reverse-phase matrix. The fractions collected after one such chromatography column may be selected by their ability to increase the clotting time of human plasma, as measured by the PT and aPTT assays, or their ability to inhibit factor X$a$ amidolytic activity as measured in a colorimetric assay. Examples of a preferred methods of purification of a recombinant protein of the present invention are disclosed in Examples 3, 5 and 6.

4. Methods of Using NAP

In one aspect, the present invention includes methods of collecting mammalian plasma, comprising adding to a blood collection tube an amount of a protein of the present invention sufficient to inhibit the formation of a clot when mammalian blood is drawn into the tube, adding mammalian blood to said tube, separating the red blood cells from the mammalian plasma, and collecting the mammalian plasma.

Blood collection tubes include stoppered test tubes having a vacuum therein as a means to draw blood obtained by venipuncture into the tubes. Preferred test tubes include those which are made of borosilicate glass, and have the dimensions of, for example, 10.25×47 mm, 10.25×50 mm, 10.25×64 mm, 10.25×82 mm, 13×75 mm, 13×100 mm, 16×75 mm, 16×100 mm or 16×125 mm. Preferred stoppers include those which can be easily punctured by a blood collection needle and which when placed onto the test tube provide a seal sufficient to prevent leaking of air into the tube.

The proteins of the present invention are added to the blood collection tubes in variety of forms well known in the art, such as a liquid composition thereof, a solid composition thereof, or a liquid composition which is lyophilized to a solid in the tube. The amount added to such tubes is that amount sufficient to inhibit the formation of a clot when mammalian blood is drawn into the tube. The proteins of the present invention are added to blood collection tubes in such amounts that, when combined with 2 to 10 ml of mammalian blood, the concentration of such proteins will be sufficient to inhibit clot formation. Typically, this effective concentration will be about 1 to 10,000 nM, with 10 to 1000 nM being preferred. Alternatively, the proteins of the present invention may be added to such tubes in combination with other clot-inhibiting additives, such as heparin salts, EDTA salts, citrate salts or oxalate salts.

After mammalian blood is drawn into a blood collection tube containing either a protein of the present invention or the same in combination with other clot-inhibiting additives, the red blood cells are separated from the mammalian plasma by centrifugation. The centrifugation is performed at g-forces, temperatures and times well known in the medical arts. Typical conditions for separating plasma from red blood cells include centrifugation at a centrifugal force of about 100×g to about 1500×g, at a temperatures of about 5° to about 25° C., and for a time of about 10 to about 60 minutes.

The mammalian plasma may be collected by pouring it off into a separate container, by withdrawing it into a pipette or by other means well known to those skilled in the medical arts.

In another aspect, the present invention includes methods for preventing thrombosis (clot formation) in a mammal, comprising administering to said mammal a therapeutically effective amount of a protein or a pharmaceutical composition of the present invention.

The proteins or pharmaceutical compositions of the present invention are administered in vivo, ordinarily in a mammal, preferably in a human. In employing them in vivo, the proteins or pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably parenteral, such as intravenous on a daily basis. Alternatively, administration is preferably oral, such as by tablets, capsules or elixers taken on a daily basis.

In practicing the methods of the present invention, the proteins or pharmaceutical compositions of the present invention are administered alone or in combination with one another, or in combination with other therapeutic or in vivo diagnostic agents.

As is apparent to one skilled in the medical art, a therapeutically effective amount of the proteins or pharmaceutical compositions of the present invention will vary depending upon the age, weight and mammalian species treated, the particular proteins employed, the particular mode of administration and the desired affects and the therapeutic indication. Because these factors and their relationship to determining this amount are well known in the medical arts, the determination of therapeutically effective dosage levels, the amount necessary to achieve the desired result of preventing thrombosis, will be within the ambit of one skilled in these arts.

Typically, administration of the proteins or pharmaceutical composition of the present invention is commenced at lower dosage levels, with dosage levels being increased until the desired effect of preventing in vivo thrombosis is achieved which would define a therapeutically effective amount. For the proteins of the present invention, alone or as part of a pharmaceutical composition, such doses are between about 0.01 mg/kg and 100 mg/kg body weight, preferably between about 0.01 and 10 mg/kg, body weight.

5. Utility

Proteins of the present invention when made and selected as disclosed are useful as potent inhibitors of blood coagulation in vitro and in vivo. As such, these proteins are useful as in vitro diagnostic reagents to prevent the clotting of blood and are also useful as in vivo pharmaceutical agents to prevent thrombosis in mammals.

The proteins of the present invention are useful as in vitro diagnostic reagents for inhibiting clotting in blood drawing tubes. The use of stoppered test tubes having a vacuum therein as a means to draw blood obtained by venipuncture into the tube is well known in the medical arts. Kasten, B. L., "Specimen Collection", *Laboratory Test Handbook*, 2nd Edition, Lexi-Comp Inc., Cleveland pp. 16–17 (Edits. Jacobs, D. S. et al. 1990). Such vacuum tubes may be free of clot-inhibiting additives, in which case, they are useful for the isolation of mammalian serum from the blood. They may alternatively contain clot-inhibiting additives (such as heparin salts, EDTA salts, citrate salts or oxalate salts), in which case, they are useful for the isolation of mammalian plasma from the blood. The proteins of the present invention are potent inhibitors of blood clotting and as such, can be incorporated into blood collection tubes to prevent clotting of the mammalian blood drawn into them.

The proteins of the present invention are used alone, in combination of other proteins of the present invention, or in combination with other known inhibitors of clotting, in the blood collection tubes, for example, with heparin salts, EDTA salts, citrate salts or oxalate salts.

The amount to be added to such tubes, or effective amount, is that amount sufficient to inhibit the formation of a blood clot when mammalian blood is drawn into the tube. The proteins of the present invention are added to blood collection tubes in such amounts that, when combined with 2 to 10 ml of mammalian blood, the concentration of such proteins will be sufficient to inhibit the formation of blood clots. Typically, this effective amount is that required to give a final concentration in the blood of about 1 to 10,000 nM, with 10 to 1000 nM being preferred.

The proteins of the present invention may also be used to prepare diagnostic compositions. In one embodiment, diagnostic compositions are prepared by dissolving the proteins of the present invention into diagnostically acceptable carriers, which carriers include phosphate buffered saline (0.01M sodium phosphate+0.15M sodium chloride, pH 7.2 or Tris buffered saline (0.05M Tris-HCl+0.15M sodium chloride, pH 8.0). In another embodiment, the proteins of the present invention may be blended with other solid diagnostically acceptable carriers by methods well known in the art to provide solid diagnostic compositions. These carriers include buffer salts.

The addition of the proteins of the present invention to blood collection tubes may be accomplished by methods well known in the art, which methods include introduction of a liquid diagnostic composition thereof, a solid diagnostic composition thereof, or a liquid diagnostic composition which is lyophilized in such tubes to a solid plug of a solid diagnostic composition.

The use of blood collection tubes containing the diagnostic compositions of the present invention comprises contacting a effective amount of such diagnostic composition with mammalian blood drawn into the tube. Typically, when a sample of 2 to 10 ml of mammalian blood is drawn into a blood collection tube and contacted with such diagnostic composition therein; the effective amount to be used will include those concentrations of the proteins formulated as a diagnostic composition which in the blood sample are sufficient to inhibit the formation of blood clots. Preferred effective concentrations would be about 1 to 10,000 nM, with 10 to 1000 nM being especially preferred.

According to an alternate aspect of our invention, the proteins of the present invention are also useful as pharmaceutical agents for preventing thrombosis in a mammals. This prevention of thrombosis includes the preventing of abnormal thrombosis.

Conditions characterized by abnormal thrombosis are well known in the medical arts and include those involving the arterial and venous vasculature of mammals. With respect to the coronary arterial vasculature, abnormal thrombosis (thrombus formation) characterizes the rupture of an established atherosclerotic plaque which is the major cause of acute myocardial infarction and unstable angina, and also characterizes the occlusive coronary thrombus formation resulting from either thrombolytic therapy or percutaneous transluminal coronary angioplasty (PTCA). With respect to the venous vasculature, abnormal thrombosis characterizes the condition observed in patients undergoing major surgery in the lower extremities or the abdominal area who often suffer from thrombus formation in the venous vasculature resulting in reduced blood flow to the affected extremity and a predisposition for pulmonary embolism. Abnormal thrombosis further characterizes disseminated intravascular coagulopathy which commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The recombinant cDNA molecules encoding the proteins of the present invention are useful in one aspect for isolating other recombinant cDNA molecules which also encode the proteins of the present invention. In another aspect, they are useful for expression in host cells of the proteins of the present invention.

To assist in understanding, the present invention will now be be further illustrated by the following examples. These examples as they relate to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Example 1

Isolation of Novel Anticoagulant Protein (NAP) from *Ancylostoma caninum*.

(A) Preparation of the *Ancylostoma caniumum* Lysate. Frozen canine hookworms, *Ancylostoma caniumum*, were obtained from Antibody Systems (Bedford, TX). Hookworms were stored at −80° C. until used for homogenate.

Hookworms were liquid nitrogen frozen and ground in a mortar followed by a homogenization on ice in homogenization buffer using a PotterS homogenizer with a teflon piston (B.Braun Melsungen AG, Germany). The homogenization buffer contained: 0.02M Tris-HCl pH 7.4, 0.05M NaCl, 0.001M $MgCl_2$, 0.001M $CaCl_2$, $1.0 \times 10^{-5}$M E-64 protease inhibitor (Boehringer Mannheim, Germany), $1.0 \times 10^{-5}$M pepstatin A (isovaleryl-Val-Val-4-amino-3-hydroxy-6-methyl-heptanoyl-Ala-4-amino-3-hydroxy-6-methylheptanoic acid, ICN Biomedicals, CA), $1.0 \times 10^{-5}$M chymostatin (Boehringer), $1.0 \times 10^{-5}$M leupeptin (ICN), $5 \times 10^{-5}$M AEBSF (4-(2-aminoethyl)-benzenesulfonyl fluoride, ICN), and 5% (v/v) glycerol. Approximately 4 ml of homogenization buffer was used to homogenize each gram of frozen worms (approximately 500 worms). Insoluble material was pelleted by two sequential centrifugation steps: $19,000 \times g_{max}$ at 4° C. for 30 minutes followed by $110,000 \times g_{max}$ at 4° C. for 40 minutes. The supernatant solution was clarified by passage through a 0.45 micrometer cellulose acetate filter (Corning, N.Y.) to give *Ancylostoma caniumum* lysate.

(B) Concanavalin A Sepharose Chromatography.

*Ancylostoma caniumum* lysate (100 ml) was adsorbed onto 22 ml of Concanavalin A Sepharose (Pharmacia, Sweden) pre-equilibrated with Con A buffer (0.02M Tris-HCl, pH 7.4, 1M NaCl, 0.002M $CaCl_2$) by loading it onto a 1.6×11 cm column of this gel at a flow rate of 3 ml/minute (90 cm/hour). The column was at ambient temperature while the reservoir of lysate was maintained at ice bath temperature throughout the procedure. The column was subsequently washed with 2 column volumes of Con A buffer. The column flow-through and wash were collected (approximately 150 ml) and stored at −80° C. until further processing was done.

(C) Anion-Exchange Chromatography.

The flow-through and wash of the Concanavalin A Sepharose column was buffered by adding solid sodium acetate to a final concentration of 12.5 mM. The conductivity was reduced by dilution with milliQ water and the pH was adjusted with HCl to pH 5.3. The precipitate formed during pH adjustment was pelleted by centrifugation $15,000 \times g_{max}$ at 4° C. for 15 minutes. The supernatant solution was clarified by passage through a 0.2 micrometer cellulose acetate filter (Corning, N.Y.).

This clarified solution (total volume approximately 600 ml) was loaded on to a Poros2O HQ (Perseptive Biosystems, MA) 1×2 cm column pre-equilibrated with Anion buffer (0.05M Na acetate, pH 5.3, 0.1M NaCl) at a flow rate of 10 ml/minute (800 cm/hour). The column and the solution added were at ambient temperature throughout this purification step. The column was subsequently washed with 10 column volumes of Anion buffer. Material that had inhibitory activity in the factor X$a$ amidolytic assay was eluted with Cation buffer containing 0.55M NaCl at a flow rate of 5 ml/minute (400 cm/hour).

(D) Heat Treatment.

Half of the 0.55M NaCl elution pool (3 ml) from anion-exchange chromatography was neutralized by adding 1M Tris-HCl, pH 7.5 to a final concentration of 50 mM, incubated for 5 minutes at 90° C. in a glass tube and subsequently cooled rapidly on ice. Insoluble material was pelleted by centrifugation $19,000 \times g_{max}$ at 4° C. for 20 minutes. The supernatant contained material which inhibited factor X$a$ in the factor X$a$ amidolytic assay. About 89% of the factor X$a$ inhibitory activity was recovered in the supernatant, after this heat treatment after accounting for dilution.

(E) Molecular Sieve Chromatography using Superdex30 (alternative for the heat treatment step).

Half of the 0.55M NaCl elution pool (3 ml) from anion-exchange chromatography was loaded on a Superdex3o PG (Pharmacia, Sweden) 1.6×66 cm column pre-equilibrated with 0.01M sodium phosphate, pH 7.4, 0.15M NaCl at 24° C. The chromatography was conducted at a flow rate of 2 ml/minute. The factor Xa inhibitory activity (determined in the factor Xa amidolytic assay) eluted 56–64 ml into the run ($K_{av}$ Of 0.207). This elution volume would be expected for a globular protein with a molecular mass of 14,000 daltons.
(F) Reverse Phase Chromatography.

Hookworm lysate which was fractionated by chromatography on Concanavalin A Sepharose, anion-exchange and Superdex30 (or with the alternative heat treatment step) was loaded on to a 0.46×25 cm C18 column (218TP54 Vydac) which was then developed with a linear gradient of 10–35% acetonitrile in 0.1% (v/v) trifluoroacetic acid at a flow rate of 1 ml/minute with a rate of 0.625% change in acetonitrile/minute. FXa inhibitory activity (determined in the factor Xa amidolytic assay) eluted at approximately 30% acetonitrile. The HPLC runs were performed on a Vista 5500 connected with a Polychrom 9600 detector set at 215 nm (Varian, Calif.). Detector signals were integrated on a 4290 integrator obtained from the same company. Factor Xa inhibitory activity containing fractions were vacuum dried and then redissolved in PBS (0.01M sodium phosphate, pH 7.4, 0.15M NaCl).

These fractions were pooled and then loaded on to a 0.46×25 cm C18 column (218TP54 Vydac) which was developed with a linear gradient of 10–35% acetonitrile in 0.1% trifluoroacetic acid at a flow rate of 1 ml/minute with a slower rate of 0.4% change in acetonitrile/minute. Factor Xa inhibitory activity containing fractions were pooled and subsequently vacuum dried.

(G) Molecular Weight Determination of NAP from *Ancylostoma caninum*.

The estimated mass for NAP isolated as described in this example was determined using electrospray ionisation mass spectrometry.

A vacuum-dried pellet of NAP was dissolved in 50% (v/v) acetonitrile, 1% (v/v) formic acid. Mass analysis was performed using a VG Bio-Q (Fisons Instruments, Manchester UK).

The NAP sample was pumped through a capillary and at its tip a high voltage of 4 kV was applied. Under the influence of the high electric field, the sample was sprayed out in droplets containing the protein molecules. Aided by the drying effect of a neutral gas ($N_2$) at 60° C., the droplets were further reduced in size until all the solvent had been evaporated and only the protein species remained in the gaseous form. A population of protein species arose which differed from each other in one charge. With a quadrupole analyzer, the different Da/e (mass/charge)-values were detected. Calibration of the instrument was accomplished using Horse Heart Myoglobin (Sigma, Mo.).

The estimated mass of NAP isolated as described in sections A, B, C, D, and F of this example is 8734.60 daltons. The estimated mass of native NAP isolated as described in sections A, B, C, E, and F is 8735.67 daltons.
(H) Amino Acid Sequencing of NAP from *Ancylostoma caninum*.

Amino acid determination was performed on a 476-A Protein/Peptide Sequencer with On Board Microgradient PTH Analyzer and Model 610A Data Analysis System (Applied Biosystems, California). Quantification of the residues was performed by on-line analysis on the system computer (Applied Biosystems, California); residue assignment was performed by visual analysis of the HPLC chromatograms. The first twenty amino acids of the amino-terminus of native NAP were determined to be:

Lys Ala Tyr Pro Glu Cys Gly Glu Asn Glu Trp Leu Asp
Asp Cys Gly Thr Gln Lys Pro [SEQ. ID. NO.10].

The cysteine residues were not directly detected in this analysis because the sample was not reduced and subsequently alkylated. Cysteines were assigned to the positions where no specific amino acid was identified.

Example 2

Cloning and Sequencing of NAP from *Ancylostoma caninum*

(A) Preparation Of Hybridization Probe.

Full-length cDNA clones encoding NAP were isolated by screening a cDNA library, prepared from the mRNA isolated from the nematode, the dog hookworm, *Ancylostoma caninum*, using as a hybridization probe—a radiolabeled degenerate oligonucleotide whose sequence was based on the first eleven amino acids of the amino-terminus of NAP from A. caninum:

Lys Ala Tyr Pro Glu Cys Gly Glu Asn Glu
Trp [SEQ. ID. NO.7].

The 33-mer oligonucleotide hybridization probe, designated YG99, had the following sequence:

AAR GCi TAY CCi GAR TGY GGi GAR AAY GAR
TGG [SEQ. ID. NO.1]

where "R" refers to A or G; "Y" refers to T or C; and "i" refers to inosine. YG99 was radiolabeled by enzymatic 5'-end phosphorylation (5'-end labeling kit; Amersham, Buckinghamshire, England) using gamma-$^{32}$P-ATP (specific activity >7000 Ci/mmole; ICN, Costa Mesa, Calif., USA) and subsequently passed over a NAP® 10 column (Pharmacia, Uppsala, Sweden).
(B) Preparation of cDNA Library.

A cDNA library was constructed using described procedures (Promega Protocols and Applications Guide 2nd Ed.; Promega Corp., Madison, Wis., USA).

Adult canine hookworms, *Ancylostoma caninum*, were obtained from Yale University, Dr. Peter Hotez. Poly(A+) RNA was prepared using the QuickPrep mRNA Purification Kit (Pharmacia). About 3 micrograms of MRNA was reverse transcribed using an oligo(dT)-NotI primer/adaptor, AATTCGCGGCCGC(T)$_{15}$ [SEQ. ID. NO. 8], (Promega Corp.) and AMV (Avian Myeloblastosis Virus) reverse transcriptase (Boehringer, Mannheim, Germany). The enzymes used for double-stranded cDNA synthesis were the following: *E. coli* DNA polymerase I and RNaseH from Life Technologies (Gaithersburg, Md., USA) and T4 DNA polymerase from Pharmacia.

EcoRI linkers (PCGGAATTCCG) [SEQ. ID. NO. 11] were ligated onto the obtained cDNA after treatment with EcoRI methylase (RiboClone EcoRI Linker Ligation System; Promega).

The cDNAs were digested with NotI and EcoRI, passed over a 1.5% agarose gel (all sizeable material was eluted using the Geneclean protocol, BIO101 Inc., La Jolla, Calif.), and unidirectionally ligated into the EcoRI-NotI arms of the lambda gt11 Sfi-NotI vector (Promega). After in vitro packaging (GigapackII-Gold, Stratagene, La Jolla, Calif.) recombinant phage.were obtained by infecting strain Y1090 (Promega).

The usefulness of the cDNA library was demonstrated by PCR analysis (Taq polymerase from Boehringer; 30 temperature cycles: 1 minute at 95° C.; 1 minute at 50° C.; 3 minutes at 72° C.) of a number of randomly picked clones using the lambda gt11 primer #1218, having the sequence, GGTGGCGACG ACTCCTGGAG CCCG [SEQ. ID. NO. 9] (New England Biolabs, Beverly, Mass., USA; targeting sequences located upstream of the cDNA insert) in combination with the above-mentioned oligo(dT)-NotI primer/adaptor; the majority of the clones was found to contain cDNA inserts of variable size.

(C) Identification of Clones.

Approximately $1 \times 10^6$ cDNA clones (duplicate plaque-lift filters were prepared using Hybond®-N; Amersham) were screened with the radiolabeled YG99 oligonucleotide using the following pre-hybridization and hybridization conditions: 5× SSC (SSC: 150 mM NaCl, 15 mM trisodium citrate), 5× Denhardt's solution, 0.5% SDS, 100 micrograms/ml sonicated fish sperm DNA (Boehringer), overnight at 42° C. The filters were washed 4 times in 2× SSC, 0.1% SDS at 37° C. After exposure (about 72 hours) to X-ray film, a total of between 350 and 500 hybridization spots were identified.

Twenty-four positive clones, designated NAP1 through NAP24, were subjected to a second hybridization round at lower plaque-density; except for NAP24, pure isolated clones were identified. The retained clones were analyzed by PCR amplifications (Taq polymerase from Boehringer; 30 temperature cycles: 1 minute at 95° C.; 1 minute at 50° C.; 1.5 minutes at 72° C.) using the oligo (dT)-NotI primer (AATTCGCGGC CGC(T)$_{15}$ [SEQ. ID. NO. 8]) in combination with either (i) YG99 or (ii) the lambda gt11 primer #1218, having the sequence, GGTGGCGACG ACTCCTGGAG CCCG [SEQ. ID. NO. 9] (New England Biolabs). The majority of the clones (20 out of 23) yielded a fragment of about 400 bp when the oligo(dT)-NotI/YG99 primer set was used and a fragment of about 520 bp when the oligo (dT)-NotI/#1218 primer couple was used. Nineteen such possibly full-length clones were further characterized.

The cDNA inserts of five clones were subcloned as SfiI-NotI fragments on both pGEM-5Zf(−) and pGEM-9Zf (−) (Promega). Because the SfiI sites of lambda gt11 and pGEM-5Zf(−) are not compatible with one another, the cloning on this vector required the use of a small adaptor fragment obtained after annealing the following two 5'-end phosphorylated oligonucleotides: pTGGCCTAGCG TCAG-GAGT [SEQ. ID. NO. 12] and PCCTGACGCTA GGC-CATGG [SEQ. ID. NO. 13]. Following preparation of single-stranded DNA, the sequence of these cDNAs was determined with the dideoxy chain termination method using primer #1233 having the sequence, AGCGGATAAC AATTTCACAC AGGA [SEQ. ID. NO. 14] (New England Biolabs). All five clones were found to be full-length including a complete secretion signal. Clones NAP5, NAP7 and NAP22 were found to have an identical coding region. Clones NAP6 and NAP11 are also identical but differ from the NAP5 type of coding region. FIG. 1 depicts the nucleotide sequence of the NAP5 gene and FIG. 2 depicts the amino acid sequence of the protein encoded, NAP isoform 5. Likewise, FIG. 3 depicts the nucleotide sequence of the NAP6 gene and FIG. 4 depicts the amino acid sequence of the protein encoded, NAP isoform 6.

Fourteen other possibly full-length clones were subjected to a restriction analysis. The above mentioned 400 bp PCR product obtained with the YG99/oligo(dT)-NotI primer couple, was digested with four different enzymes capable of discriminating between a NAP5- and NAP6-type of clone: Sau96I, Sau3AI, DdeI, and HpaII. The results were consistent with 10 out of the 14 clones being NAP5-type (e.g. NAP4, NAP8, NAP9, NAP15, NAP16, NAP17, NAP18, NAP20, NAP21, and NAP23) while the remaining four were NAP6-type (e.g. NAP10, NAP12, NAP14, and NAP19).

Example 3

Production and Purification of Recombinant NAP Isoform 5 in *P. pastoris*.

(A) Expression Vector Construction.

The *Pichia pastoris* yeast expression system, including the *E. coli*/P. pastoris shuttle vector, pHIL D2, has been described in a number of United States Patents. See, e.g., U.S. Pat. Nos. 5,330,901; 5,268,273; 5,204,261; 5,166,329; 5,135,868; 5,122,465; 5,032,516; 5,004,688; 5,002,876; 4,895,800; 4,885,242; 4,882,279; 4,879,231; 4,857,467; 4,855,231; 4,837,148; 4,818,700; 4,812,405; 4,808,537; 4,777,242; and 4,683,293.

The pYAM7SP8 vector used to direct expression and secretion of recombinant NAP in *P. pastoris* was a derivative of the pHILD2 plasmid (Despreaux, C. W. and Manning, R. F., Gene 131: 35–41 (1993)), having the same general structure. In addition to the transcription and recombination elements of pHILD2 required for expression and chromosomal integration in *P. pastoris* (see Stroman, D. W. et al., U.S. Pat. No. 4,855,231), this vector contained a chimeric prepro leader sequence inserted downstream of the alcohol oxidase (AOX1) promoter. The prepro leader consisted of the acid phosphatase (PHO1) *P. pastoris* secretion signal fused to a synthetic 19-amino acid pro-sequence. This pro-sequence was one of the two 19-aa pro-sequences designed by Clements et al., Gene 106: 267–272 (1991) on the basis of the *Saccharomyces cerevisiae* alpha-factor leader sequence. Engineered immediately downstream from the prepro leader sequence was a synthetic multi-cloning site with recognition sequences for the enzymes StuI, SacII, EcoRI, BglII, NotI, XhoI, SpeI and BamHI to facilitate the cloning of foreign genes. NAP as expressed from pYAM7SP8 in *Pichia pastoris* was first translated as a prepro-product and subsequently processed by the host cell to remove the pre- and pro- sequences.

Figures 12A, 12B:
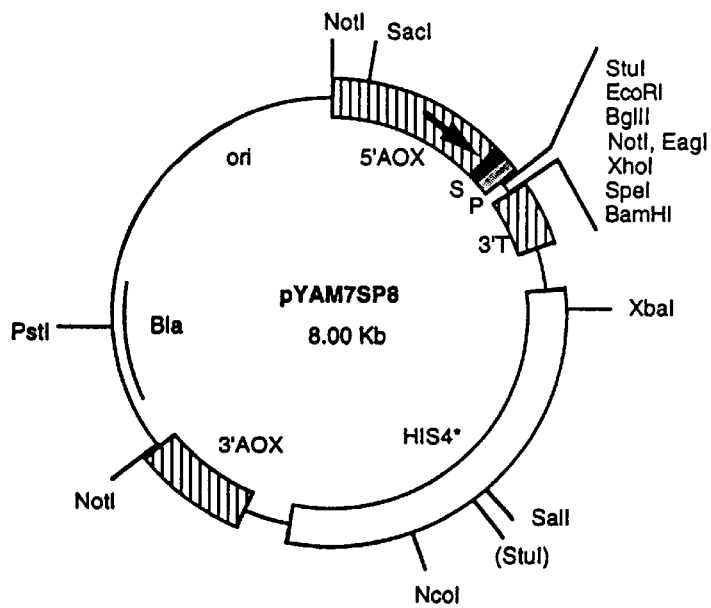
FIG. 12, Parts A and B depict a map of the *P. pastoris* pYAM7SP8 expression/secretion vector (FIG. 12, Part A) and sequences included in the vector (FIG. 12, Part B) [SEQ. ID. NO. 59]. As depicted in FIG. 12, Part A, this plasmid contains the following elements inserted between the methanol-induced AOX1 promoter (dark arrow in the 5'AOX untranslated region) and the AOX1 transcription termination signal (3'T): a synthetic DNA fragment encoding the acid phosphatase secretion signal (S), a synthetic 19-amino acid pro sequence (P) ending with a Lys-Arg processing site for the KEX2 protease and a multicloning site. The HIS4 gene which serves as a selection marker in GS115 transformation was modified by site directed mutagenesis to eliminate the Stu1 recognition sequence (HIS4*). pBR322 sequences, including the B1a gene and origin (ori) for propagation in *E. coli* are represented by a single line.

The structure of this vector is shown in FIG. 12. The signal sequence (S) has the nucleic acid sequence: ATG TTC TCT CCA ATT TTG TCC TTG GAA ATT ATT TTA GCT TTG GCT ACT TTG CAA TCT GTC TTC GCT [SEQ. ID. NO. 15]. The pro sequence (P) has the nucleic acid sequence: CAG CCA GGT ATC TCC ACT ACC GTT GGT TCC GCT GCC GAG GGT TCT TTG GAC AAG AGG [SEQ. ID. NO. 16]. The multiple cloning site (MCS) has the nucleic acid sequence: CCT ATC CGC GGA ATT CAG ATC TGA ATG CGG CCG CTC GAG ACT AGT GGA TCC [SEQ. ID. NO. 17].

The pGEM-9Zf(−) vector (Promega) containing the NAP5 cDNA was used to isolate by amplification ("PCR-rescue") the region encoding the mature NAP isoform 5 protein (using Vent polymerase from New England Biolabs, Beverly, Mass.; 20 temperature cycles: 1 minute at 94° C., 1 minute at 50° C., and 1.5 minutes at 72° C.). The following oligonucleotide primers were used:

YG101 [SEQ. ID. NO.18]:
GCTCGCTCTA-GAAGCTTCAG-ACATGTATAA-TCTCATGTTG-G
TG103 [SEQ. ID. NO.19]:
AAGGCATACC-CGGAGTGTGG-TG

The YG101 primer, targeting C-terminal sequences, contained a non-annealing extension which included XbaI and HindIII restriction sites (underlined).

Following digestion with XbaI enzyme, the amplification product, having the expected size, was isolated from gel and subsequently enzymatically phosphorylated (T4 polynucleotide kinase from New England Biolabs, Beverly, Mass.). After heat-inactivation (10 minutes at 70° C.) of the kinase, the blunt-ended/XbaI fragment was directionally cloned into the vector pYAM7SP8 for expression purposes. The recipient vector-fragment from pYAM7SP8 was prepared by StuI-SpeI restriction, and purified from agarose gel. The *E. coli* strain, WK6 [Zell, R. and Fritz, H.-J., EMBO J., 6: 1809–1815 (1987)], was transformed with the ligation mixture, and ampicillin resistant clones were selected.

Based on restriction analysis, a plasmid clone containing an insert of the expected size, designated pYAM7SP-NAP5, was retained for further characterization. Sequence determination of the clone pYAM7SP-NAP5 confirmed the precise insertion of the mature NAP5 coding region in fusion with the prepro leader signal, as predicted by the construction scheme, as well as the absence of unwanted mutations in the coding region.

(B) Expression Of Recombinant NAP Isoform 5 In *P. pastoris*.

The Pichia strain GTS115 (his4) has been described in Stroman, D. W. et al., U.S. Pat. No. 4,855,231. All of the *P. pastoris* manipulations were performed essentially as described in Stroman, D. W. et al., U.S. Pat. No. 4,855,231.

About 1 microgram of pYAM7SP-NAP5 plasmid DNA was electroporated into the strain GTS115 using a standard electroporation protocol. The plasmid was previously linearized by SalI digestion, theoretically targeting the integration event into the his4 chromosomal locus.

The selection of a NAP isoform 5 high-expresser strain was performed essentially as described hereinbelow. His+ transformants were recovered on MD plates (Yeast Nitrogen Base without amino acids (DIFCO), 13.4 g/l; Biotin, 400 micrograms/L; D-glucose, 20 g/l; agar, 15 g/1). Single colonies (n=60) originating from the electroporation were inoculated into 100 microliters of FM22-glycerol-PTM1 medium in wells of a 96-well plate and were allowed to grow on a plate-agitator at 30° C. for 24 hours. One liter of FM22-glycerol-PTM1 medium contained 42.87 g $KH_2PO_4$, 5 g $(NH_4)_2SO_4$, 1 g $CaSO_4.2H_2O$, 14.28 g $K_2SO_4$, 11.7 g $MgSO_4.7H_2O$, 50 g glycerol sterilized as a 100 ml solution, and 1 ml of PTM1 trace mineral mix filter-sterilized. The FM22 part of the medium was prepared as a 900 ml solution adjusted to pH 4.9 with KOH and sterile filtered. One liter of the PTM1 mix contained 6 g $CuSO_4.5H_2O$, 0.8 g KI, 3 g $MnSO_4.H_2O$, 0.2 g $NaMoO_4.2H_2O$, 0.02 g $H_3BO_3$, 0.5 9 $COCl_2.6H_2O$, 20 g $ZnCl_2$, 5 ml $H_2SO_4$, 65 g $FeSO_4.7H_2O$, 0.2 g biotin.

The cells were then pelleted and resuspended in fresh FM22-methanol-PTM1 medium (same composition as above except that the 50 g glycerol was replaced by 0.5% (v/v) methanol in order to induce the AOX1 promoter). After an additional incubation period of 24 hours at 30° C., the supernatants of the mini-cultures were tested for the presence of secreted NAP isoform 5. Two clones were selected that directed high synthesis and secretion of NAP isoform 5, as was shown by the appearance of high factor X$a$ inhibitory activity in the culture medium (as measured by the amidolytic factor X$a$ assay). After a second screening round, using the same procedure, but this time at the shake-flask level, one isolated host cell was chosen and designated *P. pastoris* GTS115/7SP-NAP5.

The host cell, GTS115/7SP-NAP5, was shown to have a wild type methanol-utilisation phenotype (Mut$^+$), which demonstrated that the integration of the expression cassette into the chromosome of GTS115 did not alter the functionality of the genomic AOX1 gene.

Subsequent production of recombinant NAP isoform 5 material was performed in shake flask cultures, as described in Stroman, D. W. et al., U.S. Pat. No. 4,855,231. The recombinant product was purified from *Pichia pastoris* cell supernatant as described below.

(C) Purification of NAP Isoform 5.

(1) Cation Exchange Chromatography.

The culture supernatant (100 ml) was centrifuged at 16000 r.p.m. (about 30,000×g) for 20 minutes before the pH was adjusted with 1N HCl to pH 3. The conductivity of the supernatant was decreased to less than 10 mS/cm by adding MilliQ water. The diluted supernatant was clarified by passage through a 0.22 micrometer cellulose acetate filter (Corning Inc., Corning, N.Y., USA)

The total volume (approximately 500 ml) of supernatant was loaded on a Poros20 HS (Perseptive Biosystems, Massachusetts) 1×2 cm column pre-equilibrated with Cation Buffer (0.05M sodium citrate, pH 3) at a flow rate of 5 ml/minute (400 cm/hour). The column and the sample were at ambient temperature throughout this purification step. The column was subsequently washed with 50 column volumes Cation Buffer. Material that had inhibitory activity in a factor X$a$ amidolytic assay was eluted with Cation Buffer containing 1M NaCl at a flow rate of 2 ml/minute.

(2) Molecular Sieve Chromatography Using Superdex30.

The 1M NaCl elution pool containing the inhibitory material (3 ml) from the cation-exchange column was loaded on a Superdex30 PG (Pharmacia, Sweden) 1.6×66 cm column pre-equilibrated with 0.01M sodium phosphate, pH 7.4, 0.15M NaCl at ambient temperature. The chromatography was conducted at a flow rate of 2 ml/minute. The factor X$a$ inhibitory activity eluted 56–64 ml into the run ($K_{av}$ of 0.207). This is exact the same elution volume as determined for the native molecule.

(3) Reverse Phase Chromatography.

1 ml of the pooled fractions from the gel filtration chromatography was loaded on to a 0.46×25 cm C18 column (218TP54 Vydac) which was then developed with a linear gradient of 10–35 % acetonitrile in 0.1 % (v/v) trifluoroacetic acid at 1 ml/minute with a rate of 0.4% change in acetonitrile/minute. Factor X$a$ inhibitory activity elutes around 30–35% acetonitrile and was present in several fractions. HPLC runs were performed on the same system as described in Example 1. Fractions from several runs on this column containing the factor X$a$ inhibitory activity were pooled and vacuum dried.

(4) Molecular Weight Determination of NAP Isoform 5.

The estimated mass for the main constituent isolated as described in sections (1) to (3) of this example were determined using the same electrospray ionisation mass spectrometry system as described in Example 1.

The estimated mass of recombinant NAP isoform 5 is 8735.69 daltons.

(5) Amino Acid Secruencing of NAP Isoform 5.

Following purification by section (1) to (3) of this example, the recombinant NAP from *Pichia pastoris* was subjected to amino acid sequence analysis as described in Example 1. The first five amino acids of the aminoterminus of NAP isoform 5 were determined to be: Lys-Ala-Tyr-Pro-Glu [SEQ. ID. NO. 20]. Compared to the authentic NAP protein (see Example 1), the sequence were found to be identical.

Example 4

**Production and Purification of Recombinant NAP Isoform 6 in *P. pastoris*.**

(A) Expression Vector Construction.

The expression vector, pYAM7SP-NAP6, was made in the same manner as described in Example 3.

(B) Expression of Recombinant NAP Isoform 6 in *P. pastoris*.

The vector, pYAM7SP-NAP6, was used to transform the Pichia strain GTS115 (his4) as described in Example 3.

(C) Purification of NAP Isoform 6.

The recombinant NAP isoform 6, expressed from Pichia strain GTS115 (his4) transformed with the expression vector, pYAM7SP-NAP6, was purified as described in Example 3.

The estimated mass of recombinant NAP isoform 6 was determined to be 8393.84 daltons.

The majority of the NAP isoform 6 preparation had the following amino-terminus: Lys-Ala-Tyr-Pro-Glu [SEQ. ID. NO. 20].

Example 5

Expression of Recombinant Pro-NAP Isoform 5 in COS Cells

(A) Expression Vector Construction.

The pGEM-9Zf(-) vector (Promega Corporation, Madison, Wis., USA) onto which the NAP5 cDNA was subcloned, served as target for PCR-rescue of the entire NAP isoform 5 coding region, including the native secretion signal (using Vent polymerase from New England Biolabs, Beverly, Mass., USA; 20 temperature cycles: 1 minute at 95° C., 1 minute at 50° C., and 1.5 minutes at 72° C.) The oligonucleotide primers used were: (1) YG101, targeting the 3'-end of the gene encoding a NAP and having the sequence, GCTCGC<u>TCTAGA</u>AGCTTCAG ACATGTATAA TCTCATGTTG G [SEQ. ID. NO. 18], and (2) YG102, targeting the 5'-end of the gene encoding a NAP and having the sequence, GACCAG<u>TCTAGA</u>CAATGAAG ATGCTTTACG CTATCG [SEQ. ID. NO. 21]. These primers contain non-annealing extensions which include XbaI restriction sites (underlined).

Following digestion with XbaI enzyme, the amplification product having the expected size was isolated from an agarose gel and subsequently substituted for the about 450 basepair XbaI stuffer fragment of the pEF-BOS vector [Mizushima, S. and Nagata, S., Nucl. Acids Res., 18:5322 (1990)] for expression purposes. The recipient vector-fragment was prepared by XbaI digestion and purified from an agarose gel.

*E. coli* strain WK6 [Zell, R. and Fritz, H.-J., EMBO J., 6: 1809–1815 (1987)] was transformed with the ligation mixture. Thirty randomly picked ampicillin-resistant transformants were subjected to PCR analysis (Taq polymerase from Life Technologies Inc., Gaithersburg, Md., USA; 30 cycles of amplification with the following temperature program: 1 minute at 95° C., 1 minute at 50° C., and 1 minute at 72° C.). Primers used were: (i) YG103 having the sequence, AAGGCATACC CGGAGTGTGG TG [SEQ. ID. NO. 19], and matching the amino-terminus of the region encoding mature NAP, and (ii) YG60 having the sequence, GTGGGAGACC TGATACTCTC AAG [SEQ. ID. NO. 22], and targeting vector sequences downstream of the site of insertion, i.e., in the 3'-untranslated region of the pEF-BOS expression cassette. Only clones that harbor the insert in the desired orientation can yield a PCR fragment of predictable length (about 250 basepair). Two such clones were further characterized by sequence determination and were found to contain the intended XbaI insert. One of the clones, designated pEF-BOS-NAP5, was used to transfect COS cells.

(B) Transfection of COS Cells.

COS-7 cells (ATCC CRL 1651) were transfected with pEF-BOS-NAP5, pEF-BOS containing an irrelevant insert or with omission of DNA (mock transfections) using DEAE-dextran. The following media and stock solutions are used with the DEAE-dextran method:

(1) COS-medium: DMEM; 10% FBS (incubated for 30 minutes at 56° C.); 0.03% L-glutamine; penicillin (50 I.U./ml) and streptomycin (50 micrograms/ml) (all products from Life Technologies).

(2) MEM-HEPES: MEM medium from Life Technologies Inc., reconstituted according to the manufacturer's specifications; containing a 25 mM final concentration of HEPES; adjusted to pH 7.1 before filtration (0.22 micrometer).

(3) DNA solution: 6 micrograms DNA per 3 ml MEM-HEPES (4) DEAE-dextran solution: 30 microliters DEAE-dextran stock (Pharmacia, Uppsala, Sweden; 100 mg/ml in $H_2O$) per 3 ml MEM-HEPES.

(5) Transfection mixture: 3 ml of the DEAE-dextran solution is added to 3 ml of the DNA solution and the mixture is left to stand for 30 minutes at ambient temperature.

(6) Chloroquine solution: a 1:100 dilution of chloroquine stock (Sigma, St.Louis, Mo., USA; 10 mM in water; filtered through a 0.22 micrometer membrane) in COS medium.

Transient transfection of the COS cells is performed as follows. COS cells (about $3.5 \times 10^6$), cultured in a 175 cm$^2$ Nunc TC-flask (Life Technologies Inc.) were washed once with MEM-HEPES. Six ml of the Transfection mixture was pipetted onto the washed cells. After incubation for 30 minutes at ambient temperature, 48 ml of the chloroquine solution was added and the cells were incubated for another 4 hours at 37° C. The cells were washed one time with fresh COS-medium and finally incubated in 50 ml of the same medium at 37° C.

(C) Culturing of Transfected COS Cells.

Three, four, and five days after transfection a sample of the culture supernatants was tested in a factor Xa amidolytic assay. Reaction mixtures (150 microliters) were prepared in 96-well plates containing factor Xa and various dilutions of the culture supernatants in assay buffer (100 mM Tris-HCl pH 7.4; 140 mM NaCl; 0.1% BSA). Human factor X was purchased from Enzyme Research Laboratories (South Bend, Ind., USA) and activated with Russell's Viper venom using the procedure of Bock, P. E., Craig, P. A., Olson, S. T., and Singh P., Arch. Biochem. Biophys., 273: 375–388 (1989). Following a 30 minute incubation at ambient temperature, the enzymatic reactions were initiated by addition of 50 microliters of a 1 mM substrate solution in water (N-alpha-benzyloxycarbonyl-D-arginyl-L-glycyl-L-arginine p-nitroanilidedihydrochloride; S-2765; Chromogenix, Mölndal, Sweden) to yield final concentrations of 0.2 nM factor Xa and 0.25 mM S-2765. Substrate hydrolysis was monitored by continuously measuring absorbance at 405 nm using a Vmax kinetic plate reader (Molecular Devices, Menlo Park, Calif., USA).

The results clearly demonstrated that factor Xa inhibitory activity was accumulating in the culture supernatant of the cells transfected with pEF-BOS-NAP5. From the inhibitory activity measurements, it was estimated that the NAP in the culture medium amounts to about 200 micrograms per liter.

The COS culture supernatant was harvested five days after transfection and the NAP protein purified as described in Example 6.

Example 6

Purification of Recombinant Pro-NAP Isoform 5

(A) Anion Exchange Chromatography.

The COS culture supernatant containing Pro-NAP was centrifuged at 1500 r.p.m. (about 500×g) for 10 minutes before adding solid sodium acetate to a final concentration of 50 mM. The following protease inhibitors were added (all protease inhibitors from ICN Biomedicals Inc, Costa Mesa, Calif., USA): $1.0×10^{-5}$M pepstatin A (isovaleryl-Val-Val-4-amino-3-hydroxy-6-methyl-heptanoyl-Ala-4-amino-3-hydroxy-6-methylheptanoic acid), $1.0×10^{-5}$M leupeptin, $5×10^{-5}$M AEBSF (4-(2-aminoethyl)benzenesulfonyl fluoride). The pH was adjusted with HCl to pH 5.3. The supernatant was clarified by passage through a 0.2 micrometer cellulose acetate filter (Corning Inc., Corning, N.Y., USA).

The clarified supernatant (total volume approximately 300 ml) was loaded on a Poros20 HQ (Perseptive Biosystems, Massachusetts) 1×2 cm column pre-equilibrated with Anion buffer (0.05M sodium acetate, pH 5.3, 0.1M NaCl) at a flow rate of 10 ml/minute (800 cm/hour). The column and the sample were at ambient temperature throughout this purification step. The column was subsequently washed with at least 10 column volumes of Anion buffer. Material that had inhibitory activity in a factor X$a$ amidolytic assay was eluted with Anion buffer containing 0.55M NaCl at a flow rate of 5 ml/minute (400 cm/hour) and was collected.

(B) Molecular Sieve Chromatography Using Superdex30.

The 0.55M NaCl elution pool (3 ml) from the anion-exchange chromatography was loaded on a Superdex30 PG (Pharmacia, Sweden) 1.6×66 cm column pre-equilibrated with 0.01M sodium phosphate, pH 7.4, 0.15M NaCl at 24° C. The chromatography was conducted at a flow rate of 2 ml/minute. Material which was inhibitory in the Factor X$a$ amidolytic assay eluted 56–64 ml into the run ($K_{av}$ of 0.207). This was exactly the same elution volume as determined for the native molecule.

(C) Heat Treatment.

The total pool of fractions having factor X$a$ inhibitory activity was incubated for 5 minutes at 90° C. in a glass tube and subsequently cooled rapidly on ice. Insoluble material was pelleted by centrifugation $19,000×g_{max}$ at 4° C. for 20 minutes. The supernatant contained all of the factor X$a$ inhibitory activity.

(D) Reverse Phase HPLC Chromatography.

The supernatant of the heat-treated sample was loaded onto a 0.46×25 cm C18 column (218TP54 Vydac) which was then developed with a linear gradient of 10–35% acetonitrile in 0.1% (v/v) trifluoroacetic acid at 1 ml/minute with a rate of 0.4% change in acetonitrile/minute. Factor X$a$ inhibitory activity eluted at approximately 30% acetonitrile. The HPLC runs were performed on the same system as described in Example 1. Factor X$a$ inhibitory activity containing-fractions were vacuum dried.

(E) Molecular Weight Determination.

The estimated mass for recombinant Pro-NAP, isolated as described in sections A–D of this example, was determined using the same electrospray ionisation mass spectrometry system as described in Example 1.

The estimated mass of recombinant Pro-NAP isoform 5 was 9248.4 daltons.

(F) Amino Acid Sequencing.

Following purification, the recombinant Pro-NAP from COS cells was subjected to amino acid analysis to determine its amino-terminus sequence, as described in Example 1. The first nine amino acids of the amino-terminus of Pro-NAP was determined to be: Arg Thr Val Arg Lys Ala Tyr Pro Glu [SEQ. ID. NO. 23]. Compared to the native NAP protein (see Example 1), Pro-NAP possesses a four additional amino acids on its N-terminus. The amino acid sequence of Pro-NAP isoform 5 is shown in FIG. 5.

Example 7

Expression of Recombinant Pro-NAP Isoform 6 in COS Cells

Pro-NAP isoform 6 was transiently produced in COS cells essentially as described for Pro-NAP isoform 5 in Example 5.

The NAP6 coding region, including the secretion signal, was PCR-rescued with the same two oligonucleotide primers used for NAP5: (1) YG101 [SEQ. ID. NO. 18] targeting the 3'-end of the gene and having the sequence, GCTCGCTCTA GAAGCTTCAG ACATGTATAA TCT-CATGTTG G, and (2) YG102 [SEQ. ID. NO. 22] targeting the 5'-end of the gene and having the sequence, GAC-CAGTCTA GACAATGAAG ATGCTTTACG CTATCG. The YG101-primer contains a non-matching nucleotide when used with NAP6 as target (underlined T-residue; compare with FIG. 1 and FIG. 3); this mismatch results in the replacement an ATT Ile-codon by a ATA Ile-codon. The mismatch did not markedly influence the amplification efficiency.

The following modification was introduced: twenty-four hours after transfection of the COS cells (which is described in Example 5, section B) the COS-medium containing 10% FBS was replaced 50 ml of a medium consisting of a 1:1 mixture of DMEM and Nutrient Mixture Ham's F-12 (Life Technologies). The cells were then further incubated at 37° C. and the production of factor X$a$ inhibitory activity detected as described in Example 5.

Example 8

Purification Of Recombinant Pro-NAP Isoform 6

(A) Anion Exchange Chromatography.

The COS culture supernatant containing Pro-NAP was centrifuged at 1500 r.p.m. for 10 minutes before adding solid sodium acetate to a final concentration of 50 mM. The following protease inhibitors were added (all protease inhibitors from ICN Biomedicals Inc, Costa Mesa, Calif., USA): $1.0×10^{-5}$M pepstatin A (isovaleryl-Val-Val-4-amino-3-hydroxy-6-methyl-heptanoyl-Ala-4-amino-3-hydroxy-6-methylheptanoic acid), $1.0×10^{-5}$M leupeptin, $5×10^{-5}$M AEBSF (4-(2-aminoethyl)-benzenesulfonyl fluoride). The pH was adjusted with HCl to pH 5.3. The supernatant was clarified by passage through a 0.2 micrometer cellulose acetate filter (Corning Inc., Corning, N.Y., USA).

The clarified supernatant (total volume approximately 450 ml) was loaded on a Poros20 HQ (Perseptive Biosystems, Massachusetts) 1×2 cm column pre-equilibrated with Anion buffer (0.05M Na sodium acetate, pH 5.3, 0.1M NaCl) at a flow rate of 10 ml/minute (800 cm/hour). The column and the sample were at ambient temperature throughout this purification step. The column was subsequently washed with at least 10 column volumes of Anion buffer. Material that had inhibitory activity in a factor X$a$ amidolytic assay was eluted with Anion buffer containing 0.55M NaCl at a flow rate of 5 ml/minute (400 cm/hour) and was collected.

(B) Molecular Sieve Chromatography Using Superdex30.

The 0.55M NaCl elution pool (3 ml) from the anion-exchange chromatography was loaded on a Superdex30 PG (Pharmacia, Sweden) 1.6×66 cm column pre-equilibrated with 0.01M sodium phosphate, pH 7.4, 0.15M NaCl at 24° C. The chromatography was conducted at a flow rate of 2 ml/minute. Material which was inhibitory in the Factor Xa amidolytic assay eluted 56–64 ml into the run ($K_{av}$ of 0.207). This was exactly the same elution volume as determined for the native NAP.

(C) Reverse Phase HPLC Chromatography.

The pooled fractions from the gel filtration were loaded onto a 0.46×25 cm C18 column (218TP54 Vydac) which was then developed with a linear gradient of 10–35% acetonitrile in 0.1% (v/v) trifluoroacetic acid at a flow rate of 1 ml/minute with a rate of 0.4% change in acetonitrile/minute. Factor Xa inhibitory activity eluted at approximately 30% acetonitrile. The HPLC runs were performed on the same system as described in Example 1. Factor Xa inhibitory activity containing-fractions were vacuum dried.

(D) Molecular Weight Determination.

The estimated mass for recombinant Pro-NAP isoform 6, isolated as described in sections A to C of this example, was determined using the same electrospray ionisation mass spectrometry system as described in Example 1.

The estimated mass of recombinant Pro-NAP isoform 6 was 8906.9 daltons.

(E) Amino Acid Sequencing.

Following purification, the recombinant Pro-NAP isoform 6 from COS cells was subjected to amino acid sequence analysis as described in Example 1. The first five amino acids of the N-terminus of Pro-NAP isoform 6 was determined to be: Arg Thr Val Arg Lys [SEQ. ID. NO. 24]. Compared to the native NAP protein (see Example 1), Pro-NAP isoform 6 possesses a four additional amino acids on its amino-terminus. The amino acid sequence of Pro-NAP isoform 6 is shown in FIG. 6.

Example 9

The Use of NAP DNA Sequences to Isolate Genes Encoding Other NAP Proteins.

The NAP5 and NAP6 cDNA sequences (from Example 2) were used to isolate related molecules from other parasitic species by cross-hybridization.

The pGEM-9Zf(-) vectors (Promega) containing the NAP5 and NAP6 cDNAs were used to PCR-rescue the regions encoding the mature NAP proteins (Taq polymerase from Life Technologies; 20 temperature cycles: 1 minute at 95° C., 1 minute at 50° C., and 1.5 minutes at 72° C.). The oligonucleotide primers used were: (1) YG109 [SEQ. ID. NO. 25], targeting the C-terminal sequences of cDNA encoding NAP, and having the sequence, TCAGACATGT-ATAATCTCAT-GTTGG, and (2) YG103 [SEQ. ID. NO. 19] having the sequence, AAGGCATACC-CGGAGTGTGG-TG. The YG109 primer contains a single nucleotide mismatch (underlined T-residue; compare with the sequences shown in FIGS. 1 and 3) when used with NAP6 as target. This did not markedly influence the amplification efficiency. The correctly sized PCR products (about 230 basepairs) were both isolated from a 1.5% agarose gel. An equimolar mixture was radiolabeled by random primer extension (T7 QuickPrime kit; Pharmacia) and subsequently passed over a Bio-Spin 30 column (Bio-Rad, Richmond, Calif., USA).

*Ancylostoma ceylanicum* (Ace), *Ancylostoma duodenale* (Adu), and *Heligmosomoides polygyrus* (Hpo) cDNA libraries were prepared essentially as described for *Ancylostoma caninum* in Example 2.

*Ancylostoma ceylanicum* and *Heligmosomoides polygyrus* were obtained from Dr. D. I. Pritchard, Department of Life Science, University of Nottingham, Nottingham, UK. *Ancylostoma duodenale* was obtained from Dr. G. A. Schad, The School of Veterinary Medicine, Department of Pathobiology, University of Pennsylvania, Philadelphia, Pa., USA.

In each case, the cDNAs were directionally cloned as EcoRI-NotI fragments in lambda gt11. Approximately 2×10⁵ cDNA clones from each library (duplicate plaque-lift filters were prepared using Hybond™-N; Amersham) were screened with the radiolabeled NAP5 and NAP6 fragments using the following prehybridization and hybridization conditions: 5× SSC (SSC: 150 mM NaCl, 15 mM trisodium citrate), 5× Denhardt's solution, 0.5% SDS, 20% formamide, 100 micrograms/ml sonicated fish sperm DNA (Boehringer), overnight at 42° C. The filters were washed 4 times for 30 minutes in 2× SSC, 0.1% SDS at 37° C. After exposure (about 60 hours) to X-ray film, a total of between 100 and 200 hybridization spots were identified in the case of Ace and Adu. A small number of very faint spots were visible in the case of the Hpo cDNA library. For each of the libraries, eight positives were subjected to a second hybridization round at lower plaque-density so as to isolate single pure clones.

The retained clones were further characterized by a PCR amplification of the cDNA-inserts using the oligo(dT)-NotI primer (Promega; this is the same primer used to prepare first strand cDNA; see Example 2) in combination with the lambda-gt11 primer #1218 having the sequence, GGTGGC-GACG ACTCCTGGAG CCCG [SEQ. ID. NO. 9] (New England Biolabs; primer #1218 targets lambda sequences located upstream of the site of cDNA insertion). PCR amplifications were performed as follows: Taq polymerase from Boehringer; 30 temperature cycles: 1 minute at 95° C.; 1 minute at 50° C.; 1.5 minutes at 72° C. Gel-electrophoretic analysis of the PCR products clearly demonstrated that cDNAs of roughly the same size as the NAP5 cDNA (e.g., 400 to 500 bp) were obtained for each species. In addition to these NAP5-sized cDNAs, some Ace and Adu cDNAs were estimated to be about 700 bp long.

A number of clones, containing either a 500 bp or an 800 bp insert, were chosen for sequence determination. To that end the cDNA inserts were subcloned, as SfiI-NotI fragments, onto pGEM-type phagemids (Promega; refer to Example 2 for details) which permit the preparation of single stranded DNA. The sequencing results led to the identification of six different new NAP-like proteins, designated as follows: AceNAP4, AceNAP5, AceNAP7, AduNAP4, AduNAP7, and HpoNAP5. The nucleotide sequences of the cDNAs as well as the deduced amino acid sequences of the encoded proteins are shown in FIGS. 7A-1 to 7A-2 (AceNAP4), FIG. 7B (AceNAP5), FIG. 7C (AceNAP7), FIG. 7D (AduNAP4), FIGS. 7E-1 to 7E-2 (AduNAP7), and FIG. 7F (HpoNAP5). The AceNAP4 and AduNAP7 cDNAs, each about 700 bp long, each encoded proteins which incorporated two NAP domains; the other cDNAs isolated coded for a protein having a single NAP domain. The AduNAP4 cDNA clone was not full-length, i.e,. the clone lacked the 5'-terminal part of the coding region; the correct reading frame could, however, be assigned based on amino acid sequence homology with the NAP family of related molecules.

The identified cDNA sequences can be used to produce the encoded proteins as disclosed in Examples 3, 4, 5, and 7 using the same or alternative suitable expression systems. Conditioned media or cell lysates, depending on the system used, can be tested as such or after fractionation (using such methodology as outlined in Example 3, 4, 6 and 8) for protease inhibitory and anticoagulant activity. Proteins that are encoded by cDNAs which hybridize to probes derived from fragments of the NAP5 gene (FIG. 1) and/or the NAP6 gene (FIG. 3) and that possess anticoagulant properties are considered to belong to the NAP family of related molecules.

Example 10

Identification of NAP by Functional Display of cDNA Encoded Proteins.

(A) The pDONG Series of Vectors.

The nucleotide sequences of the PDONG vectors, pDONG61, pDONG62 and pDONG63, derivatives of pUC119 [Vieira, J. and Messing, J., Methods in Enzymology, 153:311 (1987)], are depicted in FIGS. 8A to 8C respectively.

To construct these three vectors, HindIII and SfiI restriction sites were added at the 5'-end and 3'-end of the filamentous phage gene 6 by PCR amplification of the M13KO7 single stranded DNA [Vieira, J. and Messing, J., Ibid] with the G6BACKHIND backward primer and G6FORSFI61, G6FORSFI62 or G6FORSFI63 as forward primers. In a second PCR, the three obtained fragments were re-amplified with G6BACKHIND and G6FORNOTBAMH as forward primer to append NotI and BamHI sites at the 3'-end of the fragments. The sequences of the above mentioned PCR-primers are as follows (restriction sites are underlined):

G6BACKIND:ATCCGAAGCT TGCTAACAT ACTGCGTAAT AAG [SEQ. ID. NO.26]
G6FORSFI61:TATGGGATGG CCGACTTGGC CTCCGCCTGA
GCCTCCACCT TTATCCCAAT CCAAATAAGA [SEQ. ID. NO.27]
G6FORSFI62:ATGGGATGGC CGACTTGGCC CTCCGCCTGA
GCCTCCACCT TTATCCCAAT CCAAATAAGA [SEQ. ID. NO.28]
G6FORSFI63:TATGGGATGG CCGACTTGGC CGATCCGCCT
GAGCCTCCAC CTTTATCCCA ATCCAAATAA [SEQ. ID. NO.29]
GAG6FORNOTBAMH:AGGAGGGGAT CCGCGGCCGC
GTGATATGGG ATGGCCGACT TGGCC [SEQ. ID. NO.30]

Finally, the PCR products were gel-purified, individually digested with HindIII and BamHI and inserted between the corresponding sites of pUC119. Sequence determination confirmed that pDONG61, pDONG62, and pDONG63 all contained the intended insert.

The pDONG series of vectors permit the cloning of cDNAs, as SfiI-NotI fragments. This cloning fuses the cDNAs in each of the three reading frames to the 3'-end of filamentous phage gene 6 which encodes one of the phage's coat proteins. Infection of a male-specific *E. coli* strain harboring a pDONG-derivative, with VCSM13 helper phage (Stratagene, La Jolla, Calif.), results in the rescuing of pseudo-virions which encapsidate one specific single strand of the pDONG-derivative and which may also incorporate a recombinant protein 6 (p6) fusion protein in their coat. cDNAs which are such that the encoded protein is functionally displayed on the phage surface as a recombinant p6 fusion protein become identifiable by means of a panning experiment described below.

(B) Transfer of the *Ancyloscoma caninum* cDNA Library from Lambda gt11 to the pDONG Series of Vectors.

A phage lambda preparation of the pooled *A. caninum* cDNAclones (about 1×10⁶ plaques, see Example 2) was used to PCR-rescue the cDNA inserts (Taq polymerase from Life Technologies, Gaithersburg, Md., USA; 20 temperature cycles: 1 minute at 95° C., 1 minute at 50° C., and 3 minutes at 72° C. followed by 10 minutes at 65° C.), with the lambda gt11 primer #1218 having the sequence, GGTGGCGACG ACTCCTGGAG CCCG [SEQ. ID. NO. 9] (New England Biolabs, Beverly, Mass., USA; targeting sequences located upstream of the cDNA insert) in combination with the oligo(dT)-NotI primer/adaptor (Promega) used for first strand cDNA synthesis. Following digestion with the restriction enzymes SfiI and NotI, the whole size-range of amplification products were recovered from agarose gel.

All fragments were directionally cloned into the pDONG61, pDONG62, and pDONG63 vectors. The recipient vector-fragments were prepared by digestion of the CsCl purified vectors with SfiI and NotI and purification with the "Wizard™ PCR Preps DNA Purification System" (Promega Corp, Madison, Wis., USA).

*E. coli* strain TG1 [Sambrook, J., Fritsch, E. F. and Maniatis, T., *Molecular Cloning, A Laboratory Manual, Second Edition*, volumes 1 to 3, Cold Spring Harbor Laboratory Press (1989)] was transformed by electroporation with the pDONG/cDNA ligation mixtures. Electrotransformed cells were incubated 1 hour at 37° C. in SOC medium (Sambrook, J. et al., Ibid.] and plated on LB-agar containing 0.1% glucose and 100 micrograms/ml carbenicillin (245×245×25 mm plates; Nunc). 2.2×10⁶, 1.6×10⁶, and 1.4×10⁶ carbenicillin resistant transformants were obtained with pDONG61, pDONG62, and pDONG63, respectively. From each library, designated 20L, 21L and 22L, a number of randomly picked transformants were subjected to PCR analysis (Taq polymerase from Life Technologies; 30 cycles of amplification with the following temperature program: 1 minute at 95° C., 1 minute at 50° C., and 1 to 3 minutes at 72° C.) using two primers that match with sequences flanking the multiple cloning site of pUC119 (primers #1224 having the sequence, CGCCAGGGTTTTC-CCAGTCA CGAC [SEQ. ID. NO. 31], and #1233 having the sequence, AGCGGATAAC AATTTCACAC AGGA [SEQ. ID. NO. 14]; New England Biolabs). The results showed that the vast majority of the clones contained a cDNA-insert of variable size.

(C) Factor Xa Based Affinity-Selection of cDNA Clones Encoding a NAP Protein.

Phage particles from the 20L, 21L and 22L libraries were rescued as follows: each library was scraped from the plates and grown at 37° C. in 100 ml LB medium supplemented with 1% glucose and 100 micrograms/ml carbenicillin until the optical absorbance at 600 nm reaches the value of 0.5. After addition of VCSM13 helper phage (Stratagene) at a multiplicity of infection (moi) of 20, the culture was left to stand for 30 minutes at 37° C. and then slowly shaken for another 30 minutes. The cells were pelleted by centrifugation and resuspended in 250 ml LB medium supplemented with 100 micrograms/ml carbenicillin and 50 micrograms/ml kanamycin. These cultures were allowed to grow overnight at 30° C. under vigorous agitation. The resulting phage particles were purified by two consecutive precipitations with polyethylene glycol/NaCl and resuspended at 1×10¹³ virions per ml in TRIS-buffered saline (0.05M Tris, 0.15M sodium chloride, pH 7.4) (TBS). Equal amounts of phage particles from the 20L, 21L and 22L were then mixed together.

Human factor Xa (see Example A for preparation) was biotinylated with biotin-XX-NHS (Pierce). The amidolytic activity of the protease was not affected by this modification as shown by an enzymatic assay using the chromogenic substrate S-2765 (Chromogenix; see Example 3). Streptavidin-coated magnetic beads (Dynal; 1 mg per panning round) were washed three times with TBS and blocked in TBS supplemented with 2% skim milk (Difco) at ambient temperature. After one hour, the magnetic beads were washed twice with TBS before use.

For the first round of panning, 1×10^13 phage from the pooled libraries were incubated for 75 minutes at 4° C. in 200 microliters of TBS buffer supplemented with 250 nM biotinylated factor Xa, 5 mM CaCl$_2$ and 2% skim milk. After this time, 1 mg blocked streptavidin-coated magnetic beads, resuspended in 200 microliters of TBS containing 5 mM CaCl$_2$ and 2% skim milk, was added to the phage solution and incubated for 1 hour at 4° C. with gentle agitation. With a magnet (Dynal), the magnetic beads were then rinsed ten times with 500 microliters of TBS containing 0.1% Tween-20. Bound phage were eluted from the magnetic beads by incubating them with 500 microliters of 0.1M glycine-HCl buffer (pH 2.0) for 10 minutes. The supernatant was neutralized with 150 microliters 1M Tris-HCl buffer (pH 8.0).

For phage propagation, *E. coli* strain TG1 [Sambrook, J., Fritsch, E. F. and Maniatis, T., *Molecular Cloning, A Laboratory Manual, Second Edition*, volumes 1 to 3, Cold Spring Harbor Laboratory Press (1989)] was grown at 37° C. in 10 ml LB medium until the optical absorbance at 600 nm reached the value of 0.5. The culture was infected with 650 microliters of phage eluted from the magnetic beads and briefly incubated at 37° C. with no shaking. After centrifugation, the infected cells were resuspended in 2 ml LB medium and plated onto 245×245×25 mm plates filled with LB-agar containing 1% glucose and 100 micrograms/ml carbenicillin. After overnight incubation at 37° C., the cells were scraped from the plates and resuspended in 40 ml LB medium supplemented with 1% glucose and 100 micrograms/ml carbenicillin. A cell aliquot corresponding to 15 optical densities at 600 nm was then used to inoculate 100 ml LB medium containing 1% glucose and 100 micrograms/ml carbenicillin. Phage rescue for the next panning round was done as outlined above.

For the second panning round, 6×10^12 phage were incubated during 90 minutes with 1 mg blocked streptavidin-coated magnetic beads in 200 microliters of TBS containing 2.5 mM Ca$^{2+}$ and 2% skim milk (this step was introduced in the procedure to avoid selection of streptavidin-binding clones). After removal of the beads, the same protocol was followed as for round 1. Rounds 3, 4 and 5 were accomplished as round 2, except that the phage input was lowered to 2×10^12 phage.

Twenty-four individual carbenicillin resistant clones that were isolated after five rounds of panning against biotinylated factor Xa, were then analysed by ELISA. Streptavidin-coated 96-well plates (Pierce) were blocked for 1 hour with 200 microliters of TBS containing 2% skim milk per well, then were incubated for 1 hour with 100 microliters of 20 nM biotinylated factor Xa in TBS per well. For each clone, about 10^10 phage diluted in 100 microliters TBS containing 2% skim milk and 0.1% Tween-20 were added to the wells. After a 2-hour incubation, the wells were rinsed four times with 200 microliters TBS containing 0.1% Tween-20. Bound phage were visualized by consecutively incubating with a rabbit anti-M13 anti-serum (see Example 11), an alkaline phosphatase conjugated antirabbit serum (Sigma), and p-nitrophenylphosphate as substrate (Sigma). Absorbances were taken at 405 nm after 20 minutes. Out of the 24 clones, five bound strongly to factor Xa. No significant non-specific binding was observed with these phage when tested in the same ELISA with omission of biotinylated factor Xa.

Single stranded DNA was then prepared from the five positive clones and the inserts 3' to the gene 6 were submitted to automated DNA sequencing using the primer #1224 having the sequence, CGCCAGGGTT TTC-CCAGTCA CGAC [SEQ. ID. NO. 31] (New England Biolabs). All five clones were found to contain the same 470 bp 5'-truncated cDNA fused in frame to gene 6 in pDONG63. The nucleotide sequence of this cDNA as well as the deduced amino acid sequence are depicted in FIG. 9. The cDNA, designated NAPc2, encodes a protein, designated NAP isoform c2, that belongs to the NAP family of related proteins.

Example 11

Preparation of Antiserum Against M13 Phage

Antiserum against M13 phage was prepared in rabbits by subcutaneous injections of about 10^13 M13KO7 phage in 500 microliters of PBS (0.01M sodium phosphate, pH 7.4+0.15M sodium chloride) combined with an equal volume of adjuvant. The M13KO7 phage were CsCl-purified essentially as described by Glaser-Wuttke, G., Keppner, J., and Rasched, I., Biochim. Biophys. Acta, 985: 239–247 (1989). The initial injection was done with Complete Freunds adjuvant on day 0, followed by subsequent injections with Incomplete Freunds adjuvant on days 7, 14 and 35. Antiserum was harvested on day 42.

The IgG fraction of the antiserum was enriched by passage over a Protein A-Sepharose column using conditions well known in the art.

Example A

Factor Xa Amidolytic Assay

The ability of NAPs of the present invention to act a inhibitors of factor Xa catalytic activity was assessed by determining the inhibition of amidolytic activity catalyzed by the human enzyme.

The buffer used for all assays was HBSA (10 mM HEPES, pH 7.5, 150 mM sodium chloride, 0.1% bovine serum albumin).

The assay was conducted by combining in appropriate wells of a Corning microliter plate, 50 microliters of HBSA, 50 microliters of the test compound diluted in HBSA (or HBSA alone for uninhibited velocity measurement), and 50 microliters of the enzyme diluted in HBSA (prepared from purified human factor X obtained from Enzyme Research Laboratories according to the method described by Bock, P. E. et al., Archives of Biochem. Biophys. 273: 375 (1989). The enzyme was diluted into HBSA prior to the assay in which the final concentration was 0.5 nM). Following a 30 minute incubation at ambient temperature, 50 microliters of the substrate S2765 (N-alpha-benzyloxycarbonyl-D-argininyl-L-glycyl-L-arginine-p-nitroanilide dihydrochloride, obtained from Kabi Diagnostica and made up in deionized water followed by dilution in HBSA prior to the assay) was added to the wells yielding a final total volume of 200 microliters and a final concentration of 250 micromolar (about 5-times Km). The initial velocity of chromogenic substrate hydrolysis was measured by the change in absorbance at 405 nm using a Thermo Max® Kinetic Microplate Reader over a 5 minute period in which less than 5% of the added substrate was utilized.

Example B

Prothrombin Time (PT) and Activated Partial Thromboplastin Time (aPPT) Assays

The ex vivo anticoagulant effects of NAP, Pro-NAP isoform 5 and NAP isoform 5 in human plasma was evaluated by measuring the prolongation of the activated partial thromboplastin time (aPTT) and prothrombin time (PT) over a broad concentration range of each inhibitor.

Fresh frozen pooled normal human plasma was obtained from George King Biomedical, Overland Park, Kans. Respective measurements of aPTT and PT were made using the Coag-A-Mate RA4 automated coagulometer (General Diagnostics, Organon Technica, Oklahoma City, Okla.) using the Automated aPTT Platelin® L reagent (Organon Technica, Durham, N.C.) and Simplastlin® Excel (Organon Technica, Durham, N.C.) respectively, as initiators of clotting according to the manufacturers instructions.

Figure 10B:
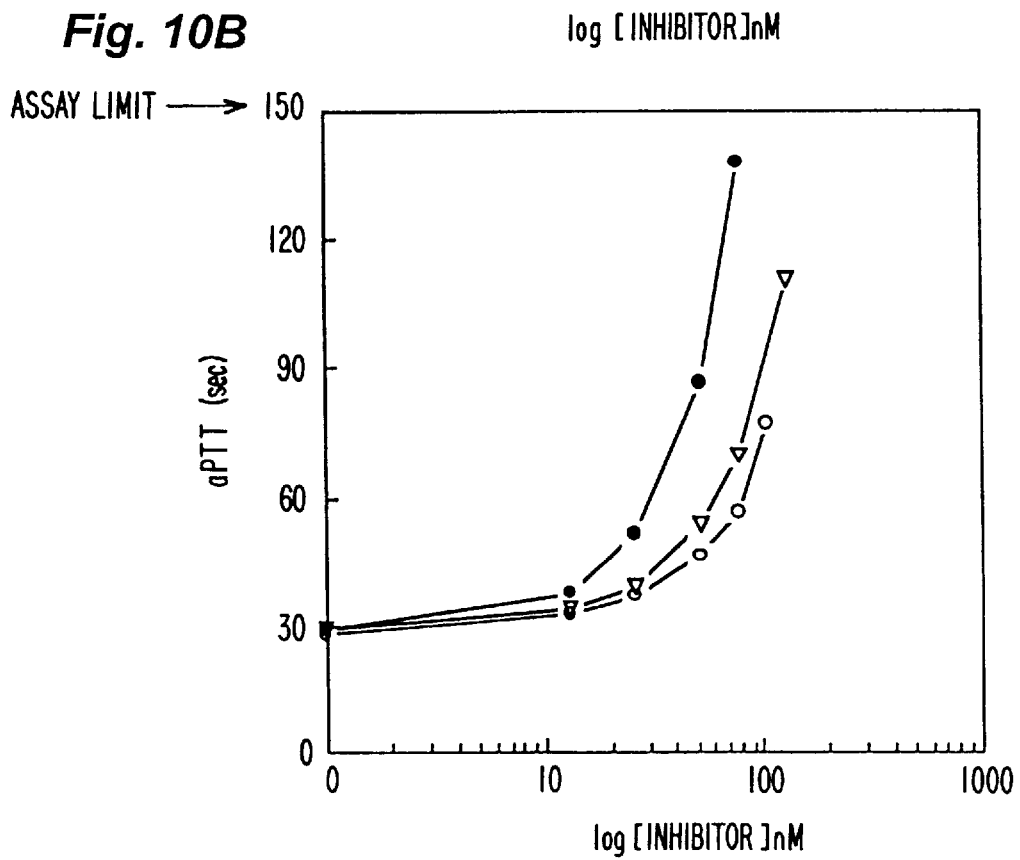

The assay was conducted by making a series of dilutions of each inhibitor in rapidly thawed plasma followed by adding 200 microliters or 100 microliters to the wells of the assay carousel for the aPTT or PT measurements, respectively. As shown in FIGS. 10A and 10B the inhibitors prolonged the PT (FIG. 10A) and aPTT (FIG. 10B) in a dose-dependent manner.

Table 1 shows the concentrations of the NAPs of the present invention at which the PT or aPTT clotting times were doubled relative to a control assay where no such NAP was present.

TABLE 1

| Inhibitor | Concentration, nM | |
|---|---|---|
| | PT Assay | aPPT Assay |
| NAP, native protein | 26.9 | 76.2 |
| NAP, isoform 5[a] | 39.2 | 60.0 |
| Pro-NAP, isoform 5[b] | 21.9 | 31.0 |

[a]This was made as a recombinant protein in *Pichia pastoris* cells.
[b]This was made as a recombinant protein in COS cells.

We claim:

1. An isolated nematode protein having anticoagulant activity and including at least one Nematode-extracted Anticoagulant Protein domain ("NAP domain"), wherein said NAP domain has an amino acid sequence having a molecular weight of about 8.7 kilodaltons to about 8.8 kilodaltons, as determined by mass spectrometry, and contains ten cysteine amino acid residues wherein the first cysteine residue of said NAP domain is within the amino acid sequence: Lys-Ala-Tyr-Pro-Glu-Cys-Gly-Glu-Asn-Glu-Trp-Leu-Asp (SEQ. ID. NO. 6) and wherein said isolated protein is derived from hematophagous nematode species.

2. A nematode protein of claim 1, wherein said anticoagulant activity, as assessed by clothing time in a prothrombin time assay, is demonstrated by doubled clothing time at a concentration of about 10 to about 50 nomomolar of said protein; and, as assessed by clothing time in an activated partial thromboplastin time assay, is demonstrated by doubled clothing time at a concentration of about 10 to about 100 nanomolar of said protein.

3. An isolated protein characterized by having the amino acid sequence depicted in FIG. 2 (SEQ. ID. NO. 32).

4. An isolated protein characterized by having the amino acid sequence in FIG. 4 (SEQ. ID. NO. 35).

5. An isolated protein characterized by having the amino acid sequence depicted in FIG. 5 (SEQ. ID. NO. 36).

6. An isolated protein characterized by having the amino acid sequence depicted in FIG. 6 (SEQ. ID. NO. 37).

7. An isolated protein encoded by the recombinant cDNA molecule having the nucleic acid sequence depicted in FIG. 7A (SEQ. ID. NO. 38), FIG. 7B (SEQ. ID. NO. 39), FIG. 7C (SEQ. ID. NO. 40), FIG. 7D (SEQ. ID. NO. 41), FIG. 7E (SEQ. ID. NO. 42), FIG. 7F (SEQ. ID. NO. 43) or FIG. 9 (SEQ. ID. NO. 47).

8. A protein of claim 7, wherein anticoagulant activity, as assessed by clotting time in a prothrombin time assay, is demonstrated by doubled clotting time at a concentration of about 5 to about 100 nanomolar of said protein; and, as assessed by clotting time in an activated partial thromboplastin time assay, is demonstrated by doubled clotting time at a concentration of about 5 to about 200 nanomolar of said protein.

9. A recombinant protein having anticoagulant activity and including at least one Nematode-extracted Anticoagulant Protein domain ("NAP domaina"), wherein said anticoagulant activity may be assessed by activity in increasing clotting time of human plasma in prothrombin time and activated partial thromboplastin time assays, and wherein said NAP domain is an amino acid sequence having a molecular weight of about 5.0 to 8.0 kilodaltons and containing 10 cysteine amino acid residues wherein said recombinant protein is made by a method comprising the steps of:

(a) isolating a cDNA library from *Ancylostoma caninum* nematode species;

(b) ligating said cDNA library into a cloning vector;

(c) introducing said cloning vector containing said cDNA library into first host cell;

(d) contacting the cDNA molecules of said first host cell with a solution of hybridization probe having a nucleic acid sequence comprising AAR GCi TAY CCi GAR TGY GGi GAR AAY GAR TTG (SEQ. ID. NO. 1), wherein R is A or G, Y is T or C, and i is inosine;

(e) detecting a recombinant cDNA molecule which hybridizes to said probe;
(f) isolating said recombinant cDNA molecule;
(c) ligating the nucleic acid sequence of said cDNA molecule which encodes said recombinant protein into an expression vector;
(h) transforming a second host cell with said expression vector containing said nucleic acid sequence of said cDNA molecule which encodes said recombinant protein;
(i) culturing transformed second host cell; and
(j) isolating said recombinant protein expressed by said second host cell.

10. A recombinant protein of claim 9, wherein said NAP domain comprises the amino acid sequence: Cys-$A_1$-Cys-$A_2$-Cys-$A_3$-Cys-$A_4$-Cys-$A_5$-Cys-$A_6$-Cys-$A_7$-Cys-$A_8$-Cys-$A_9$-Cys, wherein
(a) $A_1$ is an amino acid sequence containing 7 to 8 amino acid residues;
(b) $A_2$ is an amino acid sequence containing 2 to 5 amino acid residues;
(c) $A_3$ is an amino acid sequence containing 3 amino acid residues;
(d) $A_4$ is an amino acid sequence containing 6 to 17 amino acid residues;
(e) $A_5$ is an amino acid sequence containing 3 to 4 amino acid residues;
(f) $A_6$ is an amino acid sequence containing 3 to 5 amino acid residues;
(g) $A_7$ is an amino acid residue;
(h) $A_8$ is an amino acid sequence containing 10 to 12 amino acid residues; and
(i) $A_9$ is an amino acid sequence containing 5 to 6 amino acid residues.

11. A recombinant protein of claim 10 wherein
(a) $A_2$ is an amino acid sequence containing 4 to 5 amino acid residues; and
(b) $A_4$ is an amino acid sequence containing 6 to 16 amino acid residues.

12. A recombinant protein of claim 11, wherein:
(a) $A_1$ has Glu as its fourth amino acid residue;
(b) $A_2$ has Gly as its first amino acid residue;
(c) $A_8$ has Gly as its third amino acid residue and Arg as its sixth amino acid residue; and
(d) $A_9$ has Val as its first amino acid residue.

13. A recombinant protein of claim 12, wherein $A_3$ has Asp or Glu as its first amino acid residue and Lys or Arg as its third amino acid residue.

14. A recombinant protein of claim 13, wherein $A_7$ is Val or Gln.

15. A recombinant protein of claim 14, wherein $A_8$ has Leu or Phe as its fourth amino acid residue and Lys or Tyr as its fifth amino acid residue.

16. A recombinant protein of claim 15, wherein, when $A_8$ contains 11 or 12 amino acid residues, $A_8$ has Asp or Gly as its penultimate amino acid residue, and when $A_8$ contains 10 amino acid residues, $A_8$ has Gly as its tenth amino acid residue.

17. A recombinant protein of claim 16, further characterized by having the amino acid sequence depicted in FIG. 2 (SEQ. ID. NO. 32).

18. A recombinant protein of claim 16, further characterized by having the amino acid sequence depicted in FIG. 4 (SEQ. ID. NO. 35).

19. A recombinant protein of claim 16, further characterized by having the amino acid sequence depicted in FIG. 5 (SEQ. ID. NO. 36).

20. A recombinant protein of claim 16, further characterized by having the amino acid sequence depicted in FIG. 6 (SEQ. ID. NO. 37).

21. A recombinant protein of claim 16, wherein anticoagulant activity, as assessed by clotting time in a prothrombin time assay, is demonstrated by doubled clotting time at a concentration of about 10 to about 50 nanomolar of said protein; and, as assessed by clotting time in an activated partial thromboplastin time assay, is demonstrated by doubled clotting time at a concentration of about 10 to about 100 nanomolar of said protein.

22. A recombinant protein encoded by a recombinant cDNA molecule, wherein said cDNA molecule is made by a method comprising the steps of:

(a) isolating a cDNA library from a species of nematode selected from the group consisting of *Ancylostoma caninum, Ancylostoma ceylanicum, Ancylostoma duodenale, Necator americanus* and *Heligmosomoides polygyrus;*

(b) ligating said cDNA library into a cloning vector;

(c) introducing said cloning vector containing said cDNA library into a host cell;

(d) contacting cDNA molecules of said host cells with a solution comprising first and second hybridization probes, wherein said first hybridization probe has a nucleic acid sequence comprising:

```
AAG GCA TAC CCG GAG TGT GGT GAG AAT GAA TGG CTC GAC GAC
TGT GGA ACT CAG AAG CCA TGC GAG GCC AAG TGC AAT GAG GAA
CCC CCT GAG GAG GAA GAT CCG ATA TGC CGC TCA CGT GGT TGT
TTA TTA CCT CCT GCT TGC GTA TGC AAA GAC GGA TTC TAC AGA
GAC ACG GTG ATC GGC GAC TGT GTT AGG GAA GAA GAA TGC GAC
CAA CAT GAG ATT ATA CAT GTC TGA (SEQ ID NO:2),
``` and said second hybridization probe has a nucleic acid sequence comprising:

```
AAG GCA TAC CCG GAG TGT GGT GAG AAT GAA TGG CTC GAC GTC
TGT GGA ACT AAG AAG CCA TGC GAG GCC AAG TGC AGT GAG GAA
GAG GAG GAA GAT CCG ATA TGC CGA TCA TTT TCT TGT CCG GGT
CCC GCT GCT TGC GTA TGC GAA GAC GGA TTC TAC AGA GAC ACG
GTG ATC GGC GAC TGT GTT AAG GAA GAA GAA TGC GAC CAA CAT
GAG ATT ATA CAT GTC TGA (SEQ ID NO:3);
```

(e) detecting a recombinant cDNA molecule which hybridizes to said mixture of said probes; and (f) isolating said recombinant cDNA molecule, wherein said protein is further characterized as having anticoagulant activity and including at least one Nematode-extracted Anticoagulant Protein domain ("NAP domain"), wherein said anticoagulant activity may be assessed by activity in increasing clotting time of human plasma in prothrombin time and activated partial thromboplastin time assays, and wherein said NAP domain is an amino acid sequence having a molecular weight of about 5.0 to 8.0 kilodaltons and containing 10 cysteine amino acid residues.

23. A recombinant protein of claim 22, wherein said NAP domain comprises the amino acid sequence, Cys-$A_1$-Cys-$A_2$-Cys-$A_3$-Cys-$A_4$-Cys-$A_5$-Cys-$A_6$-Cys-$A_7$-Cys-$A_8$-Cys-$A_9$-Cys, wherein (a) $A_1$ is an amino acid sequence containing 7 to 8 amino acid residues;

(b) $A_2$ is an amino acid sequence containing 2 to 5 amino acid residues;

(c) $A_3$ is an amino acid sequence containing 3 amino acid residues;

(d) $A_4$ is an amino acid sequence containing 6 to 17 amino acid residues;

(e) $A_5$ is an amino acid sequence containing 3 to 4 amino acid residues;

(f) $A_6$ is an amino acid sequence containing 3 to 5 amino acid residues;

(g) $A_7$ is an amino acid residue;

(h) $A_8$ is an amino acid sequence containing 10 to 12 amino acid residues; and (i) $A_9$ is an amino acid sequence containing 5 to 6 amino acid residues.

24. A recombinant protein of claim 23, wherein (a) $A_2$ is an amino acid sequence containing 4 to 5 amino acid residues; and (b) $A_4$ is an amino acid sequence containing 6 to 16 amino acid residues.

25. A recombinant protein of claim 24, wherein:

(a) $A_1$ has Glu as its fourth amino acid residue;

(b) $A_2$ has Gly as its first amino acid residue;

(c) $A_8$ has Gly as its third amino acid residue and Arg as its sixth amino acid residue; and (d) $A_9$ has Val as its first amino acid residue.

26. A recombinant protein of claim 25, wherein $A_3$ has Asp or Glu as its first amino acid residue and Lys or Arg as its third amino acid residue.

27. A recombinant protein of claim 1, wherein $A_7$ is Val or Gln.

28. A recombinant protein of claim 27 wherein $A_8$ has Leu or Phe as its fourth amino acid residue and Lys or Tyr as its fifth amino acid residue.

29. A recombinant protein of claim 28 wherein, when $A_8$ contains 11 or 12 amino acid residues, $A_8$ has Asp or Gly as its penultimate amino acid residue, and when $A_8$ contains 10 amino acid residues, $A_8$ has Gly as its tenth amino acid.

30. A recombinant protein of claim 29, wherein anticoagulant activity as assessed by clotting time in a prothrombin time assay is doubled at a concentration of about 5 to about 100 nanomolar of said protein, and by clotting time in an activated partial thromboplastin time assay is doubled at a concentration of about 5 to about 200 nanomolar of said protein.

31. A recombinant protein encoded by a recombinant cDNA molecule, wherein said cDNA molecule is made by a method comprising the steps of:

(a) isolating a cDNA library from a species of nematode selected from the group consisting of *Ancylostoma caninum, Ancylostoma ceylanicum, Ancylostoma duodenale, Necator americanus* and *Heligmosomoides polygyrus;*

(b) ligating said cDNA library into a phagemid vector selected from the group consisting of pDONG61, pDONG62 and pDONG63;

(c) transforming *E. coli* strain TG1 host cells with said vector containing said cDNA library;

(d) culturing said host cells;

(e) infecting said host cells with a helper phage;

(f) separating phage containing said cDNA library from said host cells;

(g) combining a solution of said phage containing said cDNA library with a solution of biotinylated human factor X*a;*

(h) contacting streptavidin-coated solid phase with said solution containing said phage containing said cDNA library, and said biotinylated human factor X*a;*

(i) isolating phage which bind to said streptavidin-coated solid phase; and (j) isolating the recombinant cDNA molecule from phase which bind to said streptavidin-coated solid phase, wherein said protein is further characterized as having anticoagulant activity and including at least one NAP domain, wherein said anticoagulant activity may be assessed by prothrombin time and activated partial thromboplastin time assays, and wherein said NAP domain is an amino acid sequence having a molecular weight of about 5.0 to 8.0 kilodaltons and containing 10 cysteine amino acid residues.

32. A recombinant protein of claim 31, wherein said NAP domain comprises the amino acid sequence, Cys-$A_1$-Cys-$A_2$-Cys-$A_3$-Cys-$A_4$-Cys-$A_5$-Cys-$A_6$-Cys-$A_7$-Cys-$A_8$-Cys-$A_9$-Cys, wherein (a) $A_1$ is an amino acid sequence containing 7 to 8 amino acid residues;

(b) $A_2$ is an amino acid sequence containing 2 to 5 amino acid residues;

(c) $A_3$ is an amino acid sequence containing 3 amino acid residues;

(d) $A_4$ is an amino acid sequence containing 6 to 17 amino acid residues;

(e) $A_5$ is an amino acid sequence containing 3 to 4 amino acid residues;

(f) $A_6$ is an amino acid sequence containing 3 to 5 amino acid residues;

(g) $A_7$ is an amino acid residue;

(h) $A_8$ is an amino acid sequence containing 10 to 12 amino acid residues; and (i) $A_9$ is an amino acid sequence containing 5 to 6 amino acid residues.

33. A recombinant protein of claim 32, wherein (a) $A_2$ is an amino acid sequence containing 4 to 5 amino acid residues; and (b) $A_4$ is an amino acid sequence containing 6 to 16 amino acid residues.

34. A recombinant protein of claim 33, wherein:

(a) $A_1$ has Glu as its fourth amino acid residue;

(b) $A_2$ has Gly as its first amino acid residue;

(c) $A_8$ has Gly as its third amino acid residue and Arg as its sixth amino acid residue; and (d) $A_9$ has Val as its first amino acid residue.

35. A recombinant protein of claim 34, wherein:

(a) $A_3$ has Asp or Glu as its first amino acid residue and Lys or Arg as its third amino acid residue;

(b) $A_7$ is Val or Gln; and (c) $A_8$ has Leu or Phe as its fourth amino acid residue and Lys or Tyr as its fifth amino acid residue.

36. A recombinant protein of claim 35, wherein, when $A_8$ contains 11 or 12 amino acid residues, $A_8$ has Asp or Gly as its penultimate amino acid residue, and when $A_8$ contains 10 amino acid residues, $A_8$ has Gly as its tenth amino acid.

37. A recombinant protein of claim 36, wherein anticoagulant activity, as assessed by clotting time in the prothrombin time assay, is demonstrated by doubled clotting time at a concentration of about 5 to about 100 nanomolar of said protein, and, as assessed by clotting time in the activated partial thromboplastin time assay, is demonstrated by doubled clotting time at a concentration of about 5 to about 200 nanomolar of said protein.

* * * * *

SEQUENCE LISTING ( 1 ) GENERAL INFORMATION:

( i i i ) NUMBER OF SEQUENCES: 86

( 2 ) INFORMATION FOR SEQ ID NO: 1:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i x ) FEATURE:
        ( A ) NAME/KEY: Modified Base
        ( B ) LOCATION: 6...6
        ( D ) OTHER INFORMATION: N is i
        ( A ) NAME/KEY: Modified Base
        ( B ) LOCATION: 12...12
        ( D ) OTHER INFORMATION: N is i
        ( A ) NAME/KEY: Modified Base
        ( B ) LOCATION: 21...21
        ( D ) OTHER INFORMATION: N is i ( x i ) SEQUENCE DESCRIPTION: SEQ ID NO: 1:

AARGCNTAYC CNGARTGYGG NGARAAYGAR TGG                    33

( 2 ) INFORMATION FOR SEQ ID NO: 2:

( i ) SEQUENCE CHARACTERISTICS:
        ( A ) LENGTH: 234 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

AAGGCATACC CGGAGTGTGG TGAGAATGAA TGGCTCGACG ACTGTGGAAC TCAGAAGCCA    60

TGCGAGGCCA AGTGCAATGA GGAACCCCCT GAGGAGGAAG ATCCGATATG CCGCTCACGT    120

GGTTGTTTAT TACCTCCTGC TTGCGTATGC AAAGACGGAT TCTACAGAGA CACGGTGATC    180

GGCGACTGTG TTAGGGAAGA AGAATGCGAC CAACATGAGA TTATACATGT CTGA    234

( 2 ) INFORMATION FOR SEQ ID NO: 3:

( i ) SEQUENCE CHARACTERISTICS:
        ( A ) LENGTH: 228 base pairs ( B ) TYPE: nucleic acid
( C ) STRANDEDNESS: single
( D ) TOPOLOGY: linear ( x i ) SEQUENCE DESCRIPTION: SEQ ID NO: 3:

| | | | | | | |
|---|---|---|---|---|---|---|
| AAGGCATACC | CGGAGTGTGG | TGAGAATGAA | TGGCTCGACG | TCTGTGGAAC | TAAGAAGCCA | 60 |
| TGCGAGGCCA | AGTGCAGTGA | GGAAGAGGAG | GAAGATCCGA | TATGCCGATC | ATTTTCTTGT | 120 |
| CCGGGTCCCG | CTGCTTGCGT | ATGCGAAGAC | GGATTCTACA | GAGACACGGT | GATCGGCGAC | 180 |
| TGTGTTAAGG | AAGAAGAATG | CGACCAACAT | GAGATTATAC | ATGTCTGA | | 228 |

( 2 ) INFORMATION FOR SEQ ID NO: 4:

( i ) SEQUENCE CHARACTERISTICS:
        ( A ) LENGTH: 6 amino acids
        ( B ) TYPE: amino acid
        ( D ) TOPOLOGY: linear ( x i ) SEQUENCE DESCRIPTION: SEQ ID NO: 4:

Gly  Gly  Gly  Ser  Gly  Gly
1                  5

( 2 ) INFORMATION FOR SEQ ID NO: 5:

( i ) SEQUENCE CHARACTERISTICS:
        ( A ) LENGTH: 9 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in any location 2 to 9
        is an amino acid.

( x i ) SEQUENCE DESCRIPTION: SEQ ID NO: 5:

Cys  Xaa  Xaa  Xaa  Xaa  Xaa  Xaa  Xaa  Xaa
1                  5

( 2 ) INFORMATION FOR SEQ ID NO: 6:

( i ) SEQUENCE CHARACTERISTICS:
        ( A ) LENGTH: 13 amino acids
        ( B ) TYPE: amino acid
        ( D ) TOPOLOGY: linear ( v ) FRAGMENT TYPE: N-terminal fragment ( x i ) SEQUENCE DESCRIPTION: SEQ ID NO: 6:

Lys  Ala  Tyr  Pro  Glu  Cys  Gly  Glu  Asn  Glu  Trp  Leu  Asp
1                  5                           10

( 2 ) INFORMATION FOR SEQ ID NO: 7:

( i ) SEQUENCE CHARACTERISTICS:
        ( A ) LENGTH: 11 amino acids
        ( B ) TYPE: amino acid
        ( D ) TOPOLOGY: linear ( x i ) SEQUENCE DESCRIPTION: SEQ ID NO: 7:

Lys  Ala  Tyr  Pro  Glu  Cys  Gly  Glu  Asn  Glu  Trp
1                  5                           10

( 2 ) INFORMATION FOR SEQ ID NO: 8:

( i ) SEQUENCE CHARACTERISTICS:
        ( A ) LENGTH: 28 base pairs
        ( B ) TYPE: nucleic acid ( C ) STRANDEDNESS: single
( D ) TOPOLOGY: linear ( x i ) SEQUENCE DESCRIPTION: SEQ ID NO: 8:

AATTCGCGGC CGCTTTTTTT TTTTTTTT                    28

( 2 ) INFORMATION FOR SEQ ID NO: 9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 9:

GGTGGCGACG ACTCCTGGAG CCCG                        24

( 2 ) INFORMATION FOR SEQ ID NO: 10:

( i ) SEQUENCE CHARACTERISTICS:
        ( A ) LENGTH: 20 amino acids
        ( B ) TYPE: amino acid
        ( D ) TOPOLOGY: linear ( x i ) SEQUENCE DESCRIPTION: SEQ ID NO: 10:

Lys Ala Tyr Pro Glu Cys Gly Glu Asn Glu Trp Leu Asp Asp Cys Gly Thr
1               5                   10                  15

Gln Lys Pro
        20

( 2 ) INFORMATION FOR SEQ ID NO: 11:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 11:

CGGAATTCCG                                        10

( 2 ) INFORMATION FOR SEQ ID NO: 12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 12:

TGGCCTAGCG TCAGGAGT                               18

( 2 ) INFORMATION FOR SEQ ID NO: 13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 13:

CCTGACGCTA GGCCATGG                               18

( 2 ) INFORMATION FOR SEQ ID NO: 14:

( i ) SEQUENCE CHARACTERISTICS:
        ( A ) LENGTH: 24 base pairs ( B ) TYPE: nucleic acid
( C ) STRANDEDNESS: single
( D ) TOPOLOGY: linear ( x i ) SEQUENCE DESCRIPTION: SEQ ID NO: 14:

AGCGGATAAC AATTTCACAC AGGA                                                       24

( 2 ) INFORMATION FOR SEQ ID NO: 15:

( i ) SEQUENCE CHARACTERISTICS:
( A ) LENGTH: 66 base pairs
( B ) TYPE: nucleic acid
( C ) STRANDEDNESS: single
( D ) TOPOLOGY: linear ( x i ) SEQUENCE DESCRIPTION: SEQ ID NO: 15:

ATGTTCTCTC CAATTTGTC CTTGGAAATT ATTTTAGCTT TGGCTACTTT GCAATCTGTC                  60

TTCGCT                                                                            66

( 2 ) INFORMATION FOR SEQ ID NO: 16:

( i ) SEQUENCE CHARACTERISTICS:
( A ) LENGTH: 57 base pairs
( B ) TYPE: nucleic acid
( C ) STRANDEDNESS: single
( D ) TOPOLOGY: linear ( x i ) SEQUENCE DESCRIPTION: SEQ ID NO: 16:

CAGCCAGGTA TCTCCACTAC CGTTGGTTCC GCTGCCGAGG GTTCTTTGGA CAAGAGG                    57

( 2 ) INFORMATION FOR SEQ ID NO: 17:

( i ) SEQUENCE CHARACTERISTICS:
( A ) LENGTH: 51 base pairs
( B ) TYPE: nucleic acid
( C ) STRANDEDNESS: single
( D ) TOPOLOGY: linear ( x i ) SEQUENCE DESCRIPTION: SEQ ID NO: 17:

CCTATCCGCG GAATTCAGAT CTGAATGCGG CCGCTCGAGA CTAGTGGATC C                          51

( 2 ) INFORMATION FOR SEQ ID NO: 18:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( x i ) SEQUENCE DESCRIPTION: SEQ ID NO: 18:

GCTCGCTCTA GAAGCTTCAG ACATGTATAA TCTCATGTTG G                                     41

( 2 ) INFORMATION FOR SEQ ID NO: 19:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO: 19:

AAGGCATACC CGGAGTGTGG TG                                                          22

( 2 ) INFORMATION FOR SEQ ID NO: 20:

( i ) SEQUENCE CHARACTERISTICS:
( A ) LENGTH: 5 amino acids (B) TYPE: amino acid
(D) TOPOLOGY: linear (v) FRAGMENT TYPE: N-terminal fragment (xi) SEQUENCE DESCRIPTION: SEQ ID NO: 20:

```
Lys Ala Tyr Pro Glu
 1               5
```

(2) INFORMATION FOR SEQ ID NO: 21:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO: 21:

GACCAGTCTA GACAATGAAG ATGCTTTACG CTATCG   36

(2) INFORMATION FOR SEQ ID NO: 22:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 22:

GTGGGAGACC TGATACTCTC AAG   23

(2) INFORMATION FOR SEQ ID NO: 23:

(i) SEQUENCE CHARACTERISTICS:
(A) LENGTH: 9 amino acids
(B) TYPE: amino acid
(D) TOPOLOGY: linear (v) FRAGMENT TYPE: N-terminal fragment (xi) SEQUENCE DESCRIPTION: SEQ ID NO: 23:

```
Arg Thr Val Arg Lys Ala Tyr Pro Glu
 1               5
```

(2) INFORMATION FOR SEQ ID NO: 24:

(i) SEQUENCE CHARACTERISTICS:
(A) LENGTH: 5 amino acids
(B) TYPE: amino acid
(D) TOPOLOGY: linear (v) FRAGMENT TYPE: N-terminal fragment (xi) SEQUENCE DESCRIPTION: SEQ ID NO: 24:

```
Arg Thr Val Arg Lys
 1               5
```

(2) INFORMATION FOR SEQ ID NO: 25:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 25:

TCAGACATGT ATAATCTCAT GTTGG   25

( 2 ) INFORMATION FOR SEQ ID NO: 26:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 26:

```
ATCCGAAGCT  TTGCTAACAT  ACTGCGTAAT  AAG                                33
```

( 2 ) INFORMATION FOR SEQ ID NO: 27:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 27:

```
TATGGGATGG  CCGACTTGGC  CTCCGCCTGA  GCCTCCACCT  TTATCCCAAT  CCAAATAAGA    60
```

( 2 ) INFORMATION FOR SEQ ID NO: 28:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 28:

```
ATGGGATGGC  CGACTTGGCC  CTCCGCCTGA  GCCTCCACCT  TTATCCCAAT  CCAAATAAGA    60
```

( 2 ) INFORMATION FOR SEQ ID NO: 29:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 29:

```
TATGGGATGG  CCGACTTGGC  CGATCCGCCT  GAGCCTCCAC  CTTTATCCCA  ATCCAAATAA    60
```

( 2 ) INFORMATION FOR SEQ ID NO: 30:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 30:

```
AGGAGGGGAT  CCGCGGCCGC  GTGATATGGG  ATGGCCGACT  TGGCC                    45
```

( 2 ) INFORMATION FOR SEQ ID NO: 31:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 31:

```
CGCCAGGGTT  TTCCCAGTCA  CGAC                                             24
```

( 2 ) INFORMATION FOR SEQ ID NO: 32:

( i ) SEQUENCE CHARACTERISTICS:
  ( A ) LENGTH: 461 base pairs
  ( B ) TYPE: nucleic acid
  ( C ) STRANDEDNESS: single
  ( D ) TOPOLOGY: linear ( i x ) FEATURE:
  ( A ) NAME/KEY: Coding Sequence
  ( B ) LOCATION: 22...321
  ( D ) OTHER INFORMATION:

( x i ) SEQUENCE DESCRIPTION: SEQ ID NO: 32:

| G AATTCCGCT ACTACTCAACA | ATG | AAG | ATG | CTT | TAC | GCT | ATC | GCT | ATA | ATG | 51 |
|---|---|---|---|---|---|---|---|---|---|---|---|
| | Met | Lys | Met | Leu | Tyr | Ala | Ile | Ala | Ile | Met | |
| | 1 | | | 5 | | | | | | 10 | |

| TTT | CTC | CTG | GTA | TCA | TTA | TGC | AGC | GCA | AGA | ACA | GTG | AGG | AAG | GCA | TAC | 99 |
|---|---|---|---|---|---|---|---|---|---|---|---|---|---|---|---|---|
| Phe | Leu | Leu | Val | Ser | Leu | Cys | Ser | Ala | Arg | Thr | Val | Arg | Lys | Ala | Tyr | |
| | | | | 15 | | | | | 20 | | | | | 25 | | |

| CCG | GAG | TGT | GGT | GAG | AAT | GAA | TGG | CTC | GAC | GAC | TGT | GGA | ACT | CAG | AAG | 147 |
|---|---|---|---|---|---|---|---|---|---|---|---|---|---|---|---|---|
| Pro | Glu | Cys | Gly | Glu | Asn | Glu | Trp | Leu | Asp | Asp | Cys | Gly | Thr | Gln | Lys | |
| | | | | 30 | | | | 35 | | | | | 40 | | | |

| CCA | TGC | GAG | GCC | AAG | TGC | AAT | GAG | GAA | CCC | CCT | GAG | GAG | GAA | GAT | CCG | 195 |
|---|---|---|---|---|---|---|---|---|---|---|---|---|---|---|---|---|
| Pro | Cys | Glu | Ala | Lys | Cys | Asn | Glu | Glu | Pro | Pro | Glu | Glu | Glu | Asp | Pro | |
| | | | 45 | | | | 50 | | | | | 55 | | | | |

| ATA | TGC | CGC | TCA | CGT | GGT | TGT | TTA | TTA | CCT | CCT | GCT | TGC | GTA | TGC | AAA | 243 |
|---|---|---|---|---|---|---|---|---|---|---|---|---|---|---|---|---|
| Ile | Cys | Arg | Ser | Arg | Gly | Cys | Leu | Leu | Pro | Pro | Ala | Cys | Val | Cys | Lys | |
| | 60 | | | | | 65 | | | | | 70 | | | | | |

| GAC | GGA | TTC | TAC | AGA | GAC | ACG | GTG | ATC | GGC | GAC | TGT | GTT | AGG | GAA | GAA | 291 |
|---|---|---|---|---|---|---|---|---|---|---|---|---|---|---|---|---|
| Asp | Gly | Phe | Tyr | Arg | Asp | Thr | Val | Ile | Gly | Asp | Cys | Val | Arg | Glu | Glu | |
| 75 | | | | | 80 | | | | | 85 | | | | | 90 | |

| GAA | TGC | GAC | CAA | CAT | GAG | ATT | ATA | CAT | GTC | TGAACGAGAA | AGCAACAATA | ACCA | 345 |
|---|---|---|---|---|---|---|---|---|---|---|---|---|---|
| Glu | Cys | Asp | Gln | His | Glu | Ile | Ile | His | Val | | | | |
| | | | | 95 | | | | | 100 | | | | |

AAGGTTCCAA CTCTCGCTCT GCAAAATCGC TAGTTGGATG TCTCTTTTGC GTCCGAATAG   405
TTTTAGTTGA TGTTAAGTAA GAACTCCTGC TGGAGAGAAT AAAGCTTTCC AACTCC   461

( 2 ) INFORMATION FOR SEQ ID NO: 33:

( i ) SEQUENCE CHARACTERISTICS:
    ( A ) LENGTH: 77 amino acids
    ( B ) TYPE: amino acid
    ( D ) TOPOLOGY: linear ( x i ) SEQUENCE DESCRIPTION: SEQ ID NO: 33:

| Lys | Ala | Tyr | Pro | Glu | Cys | Gly | Glu | Asn | Glu | Trp | Leu | Asp | Asp | Cys | Gly | Thr | Gln |
|---|---|---|---|---|---|---|---|---|---|---|---|---|---|---|---|---|---|
| 1 | | | | 5 | | | | | 10 | | | | | 15 | | | |

| Lys | Pro | Cys | Glu | Ala | Lys | Cys | Asn | Glu | Glu | Pro | Pro | Glu | Glu | Glu | Asp | Pro | Ile |
|---|---|---|---|---|---|---|---|---|---|---|---|---|---|---|---|---|---|
| | | 20 | | | | | 25 | | | | | 30 | | | | | 35 |

| Cys | Arg | Ser | Arg | Gly | Cys | Leu | Leu | Pro | Pro | Ala | Cys | Val | Cys | Lys | Asp | Gly | Phe |
|---|---|---|---|---|---|---|---|---|---|---|---|---|---|---|---|---|---|
| | | | 40 | | | | | 45 | | | | | 50 | | | | |

| Tyr | Arg | Asp | Thr | Val | Ile | Gly | Asp | Cys | Val | Arg | Glu | Glu | Glu | Cys | Asp | Gln | His |
|---|---|---|---|---|---|---|---|---|---|---|---|---|---|---|---|---|---|
| 55 | | | | | 60 | | | | | 65 | | | | | 70 | | |

| Glu | Ile | Ile | His | Val |
|---|---|---|---|---|
| | | | 75 | |

( 2 ) INFORMATION FOR SEQ ID NO: 34:

( i ) SEQUENCE CHARACTERISTICS:
    ( A ) LENGTH: 455 base pairs
    ( B ) TYPE: nucleic acid
    ( C ) STRANDEDNESS: single
    ( D ) TOPOLOGY: linear ( i x ) FEATURE:

( A ) NAME/KEY: Coding Sequence
        ( B ) LOCATION: 22...315
        ( D ) OTHER INFORMATION:

( x i ) SEQUENCE DESCRIPTION: SEQ ID NO: 34:

G  AATTCCGCTA  CTACTCAACA  ATG  AAG  ATG  CTT  TAC  GCT  ATC  GCT  ATA  ATG         51
                                 Met  Lys  Met  Leu  Tyr  Ala  Ile  Ala  Ile  Met
                                  1              5                         10

TTT  CTC  CTG  GTG  TCA  TTA  TGC  AGC  ACA  AGA  ACA  GTG  AGG  AAG  GCA  TAC      99
Phe  Leu  Leu  Val  Ser  Leu  Cys  Ser  Thr  Arg  Thr  Val  Arg  Lys  Ala  Tyr
               15                           20                      25

CCG  GAG  TGT  GGT  GAG  AAT  GAA  TGG  CTC  GAC  GTC  TGT  GGA  ACT  AAG  AAG     147
Pro  Glu  Cys  Gly  Glu  Asn  Glu  Trp  Leu  Asp  Val  Cys  Gly  Thr  Lys  Lys
               30                      35                      40

CCA  TGC  GAG  GCC  AAG  TGC  AGT  GAG  GAA  GAG  GAG  GAA  GAT  CCG  ATA  TGC     195
Pro  Cys  Glu  Ala  Lys  Cys  Ser  Glu  Glu  Glu  Glu  Glu  Asp  Pro  Ile  Cys
          45                      50                          55

CGA  TCA  TTT  TCT  TGT  CCG  GGT  CCC  GCT  GCT  TGC  GTA  TGC  GAA  GAC  GGA     243
Arg  Ser  Phe  Ser  Cys  Pro  Gly  Pro  Ala  Ala  Cys  Val  Cys  Glu  Asp  Gly
 60                           65                      70

TTC  TAC  AGA  GAC  ACG  GTG  ATC  GGC  GAC  TGT  GTT  AAG  GAA  GAA  GAA  TGC     291
Phe  Tyr  Arg  Asp  Thr  Val  Ile  Gly  Asp  Cys  Val  Lys  Glu  Glu  Glu  Cys
 75                      80                      85                      90

GAC  CAA  CAT  GAG  ATT  ATT  CAT  GTC  TGAACGAGAG  AGCAGTAATA  ACCAAAGGTT  C       346
Asp  Gln  His  Glu  Ile  Ile  His  Val
                     95

CAACTTTCGC  TCTACAAAAT  CGCTAGTTGG  ATTTCTCCTT  TGCGTGCGAA  TAGTTTTAGT              406

TGATATTAAG  TAAAACCTCC  TGTTGAAGAG  AATAAAGCTT  TCCAACTTC                           455

( 2 ) INFORMATION FOR SEQ ID NO: 35:

( i ) SEQUENCE CHARACTERISTICS:
            ( A ) LENGTH: 75 amino acids
            ( B ) TYPE: amino acid
            ( D ) TOPOLOGY: linear ( x i ) SEQUENCE DESCRIPTION: SEQ ID NO: 35:

Lys  Ala  Tyr  Pro  Glu  Cys  Gly  Glu  Asn  Glu  Trp  Leu  Asp  Val  Cys  Gly  Thr  Lys
 1              5                        10                        15

Lys  Pro  Cys  Glu  Ala  Lys  Cys  Ser  Glu  Glu  Glu  Glu  Asp  Pro  Ile  Cys  Arg
      20                  25                       30                        35

Ser  Phe  Ser  Cys  Pro  Gly  Pro  Ala  Ala  Cys  Val  Cys  Glu  Asp  Gly  Phe  Tyr  Arg
               40                       45                        50

Asp  Thr  Val  Ile  Gly  Asp  Cys  Val  Lys  Glu  Glu  Glu  Cys  Asp  Gln  His  Glu  Ile
 55                       60                       65                        70

Ile  His  Val ( 2 ) INFORMATION FOR SEQ ID NO: 36:

( i ) SEQUENCE CHARACTERISTICS:
            ( A ) LENGTH: 81 amino acids
            ( B ) TYPE: amino acid
            ( D ) TOPOLOGY: linear ( x i ) SEQUENCE DESCRIPTION: SEQ ID NO: 36:

Arg  Thr  Val  Arg  Lys  Ala  Tyr  Pro  Glu  Cys  Gly  Glu  Asn  Glu  Trp  Leu  Asp  Asp
 1              5                        10                        15

Cys  Gly  Thr  Gln  Lys  Pro  Cys  Glu  Ala  Lys  Cys  Asn  Glu  Glu  Pro  Pro  Glu  Glu
      20                  25                       30                        35

Glu  Asp  Pro  Ile  Cys  Arg  Ser  Arg  Gly  Cys  Leu  Leu  Pro  Pro  Ala  Cys  Val  Cys
               40                       45                        50

```
Lys  Asp  Gly  Phe  Tyr  Arg  Asp  Thr  Val  Ile  Gly  Asp  Cys  Val  Arg  Glu  Glu  Glu
 55             60                      65                      70

Cys  Asp  Gln  His  Glu  Ile  Ile  His  Val
              75                  80
```

( 2 ) INFORMATION FOR SEQ ID NO: 37:

( i ) SEQUENCE CHARACTERISTICS:
        ( A ) LENGTH: 79 amino acids
        ( B ) TYPE: amino acid
        ( D ) TOPOLOGY: linear ( x i ) SEQUENCE DESCRIPTION: SEQ ID NO: 37:

```
Arg  Thr  Val  Arg  Lys  Ala  Tyr  Pro  Glu  Cys  Gly  Glu  Asn  Glu  Trp  Leu  Asp  Val
 1              5                       10                      15

Cys  Gly  Thr  Lys  Lys  Pro  Cys  Glu  Ala  Lys  Cys  Ser  Glu  Glu  Glu  Glu  Glu  Asp
        20                  25                      30                          35

Pro  Ile  Cys  Arg  Ser  Phe  Ser  Cys  Pro  Gly  Pro  Ala  Ala  Cys  Val  Cys  Glu  Asp
              40                      45                      50

Gly  Phe  Tyr  Arg  Asp  Thr  Val  Ile  Gly  Asp  Cys  Val  Lys  Glu  Glu  Glu  Cys  Asp
 55             60                      65                      70

Gln  His  Glu  Ile  Ile  His  Val
              75
```

( 2 ) INFORMATION FOR SEQ ID NO: 38:

( i ) SEQUENCE CHARACTERISTICS:
        ( A ) LENGTH: 711 base pairs
        ( B ) TYPE: nucleic acid
        ( C ) STRANDEDNESS: single
        ( D ) TOPOLOGY: linear ( i x ) FEATURE:
        ( A ) NAME/KEY: Coding Sequence
        ( B ) LOCATION: 21...590
        ( D ) OTHER INFORMATION:

( x i ) SEQUENCE DESCRIPTION: SEQ ID NO: 38:

```
GAATTCACTA  TTATCCAACA  ATG  GCG  GTG  CTT  TAT  TCA  GTA  GCA  ATA  GCG                 50
                       Met  Ala  Val  Leu  Tyr  Ser  Val  Ala  Ile  Ala
                        1              5                       10

TTA  CTA  CTG  GTA  TCA  CAA  TGC  AGT  GGG  AAA  CCG  AAC  AAT  GTG  ATG  ACT           98
Leu  Leu  Leu  Val  Ser  Gln  Cys  Ser  Gly  Lys  Pro  Asn  Asn  Val  Met  Thr
                    15                      20                      25

AAC  GCT  TGT  GGT  CTT  AAT  GAA  TAT  TTC  GCT  GAG  TGT  GGC  AAT  ATG  AAG          146
Asn  Ala  Cys  Gly  Leu  Asn  Glu  Tyr  Phe  Ala  Glu  Cys  Gly  Asn  Met  Lys
          30                      35                      40

GAA  TGC  GAG  CAC  AGA  TGC  AAT  GAG  GAG  GAA  AAT  GAG  GAA  AGG  GAC  GAG          194
Glu  Cys  Glu  His  Arg  Cys  Asn  Glu  Glu  Glu  Asn  Glu  Glu  Arg  Asp  Glu
               45                      50                      55

GAA  AGA  ATA  ACG  GCA  TGC  CTC  ATC  CGT  GTG  TGT  TTC  CGT  CCT  GGT  GCT          242
Glu  Arg  Ile  Thr  Ala  Cys  Leu  Ile  Arg  Val  Cys  Phe  Arg  Pro  Gly  Ala
      60                      65                      70

TGC  GTA  TGC  AAA  GAC  GGA  TTC  TAT  AGA  AAC  AGA  ACA  GGC  AGC  TGT  GTG          290
Cys  Val  Cys  Lys  Asp  Gly  Phe  Tyr  Arg  Asn  Arg  Thr  Gly  Ser  Cys  Val
 75                      80                      85                      90

GAA  GAA  GAT  GAC  TGC  GAG  TAC  GAG  AAT  ATG  GAG  TTC  ATT  ACT  TTT  GCA          338
Glu  Glu  Asp  Asp  Cys  Glu  Tyr  Glu  Asn  Met  Glu  Phe  Ile  Thr  Phe  Ala
                    95                      100                     105

CCA  GAA  GTA  CCG  ATA  TGT  GGT  TCC  AAC  GAA  AGG  TAC  TCC  GAC  TGC  GGC          386
Pro  Glu  Val  Pro  Ile  Cys  Gly  Ser  Asn  Glu  Arg  Tyr  Ser  Asp  Cys  Gly
               110                     115                     120
```

| | | | | | | | | | | | | | | | |
|---|---|---|---|---|---|---|---|---|---|---|---|---|---|---|---|
| AAT | GAC | AAA | CAA | TGC | GAG | CGC | AAA | TGC | AAC | GAG | GAC | GAT | TAT | GAG | AAG | 434
| Asn | Asp | Lys | Gln | Cys | Glu | Arg | Lys | Cys | Asn | Glu | Asp | Asp | Tyr | Glu | Lys |
| | | 125 | | | | 130 | | | | | | 135 | | | |
| GGA | GAT | GAG | GCA | TGC | CGC | TCA | CAT | GTT | TGT | GAA | CGT | CCT | GGT | GCC | TGT | 482
| Gly | Asp | Glu | Ala | Cys | Arg | Ser | His | Val | Cys | Glu | Arg | Pro | Gly | Ala | Cys |
| | 140 | | | | | 145 | | | | | 150 | | | | |
| GTA | TGC | GAA | GAC | GGG | TTC | TAC | AGA | AAC | AAA | AAA | GGT | AGC | TGT | GTG | GAA | 530
| Val | Cys | Glu | Asp | Gly | Phe | Tyr | Arg | Asn | Lys | Lys | Gly | Ser | Cys | Val | Glu |
| 155 | | | | | 160 | | | | | 165 | | | | | 170 |
| AGC | GAT | GAC | TGC | GAA | TAC | GAT | AAT | ATG | GAT | TTC | ATC | ACT | TTT | GCA | CCA | 578
| Ser | Asp | Asp | Cys | Glu | Tyr | Asp | Asn | Met | Asp | Phe | Ile | Thr | Phe | Ala | Pro |
| | | | | 175 | | | | | 180 | | | | | 185 | |
| GAA | ACC | TCA | CGA | TAACCAAGA | TGCTACCTCT | CGTACGCAAC | TCCGCTGATT | GAGGTT | | | | | | | 636
| Glu | Thr | Ser | Arg | | | | | | | | | | | | |
| | | | 190 | | | | | | | | | | | | |

GATTCACTCC CTTGCATCTC AACATTTTTT TTGTGATGCT GTGCATCTGA GCTTAACCTG    696

ATAAAGCCTA TGGTG    711

( 2 ) INFORMATION FOR SEQ ID NO: 39:

( i ) SEQUENCE CHARACTERISTICS:
        ( A ) LENGTH: 425 base pairs
        ( B ) TYPE: nucleic acid
        ( C ) STRANDEDNESS: single
        ( D ) TOPOLOGY: linear ( i x ) FEATURE:
        ( A ) NAME/KEY: Coding Sequence
        ( B ) LOCATION: 10...291
        ( D ) OTHER INFORMATION:

( x i ) SEQUENCE DESCRIPTION: SEQ ID NO: 39:

| | | | | | | | | | | | | | | | |
|---|---|---|---|---|---|---|---|---|---|---|---|---|---|---|---|
| GAATTCCGC | ATG | CGG | ACG | CTC | TAC | CTC | ATT | TCT | ATC | TGG | TTG | TTC | CTC | ATC | 51
| | Met | Arg | Thr | Leu | Tyr | Leu | Ile | Ser | Ile | Trp | Leu | Phe | Leu | Ile |
| | 1 | | | | 5 | | | | | 10 | | | | | |
| TCG | CAA | TGT | AAT | GGA | AAA | GCA | TTC | CCG | AAA | TGT | GAC | GTC | AAT | GAA | AGA | 99
| Ser | Gln | Cys | Asn | Gly | Lys | Ala | Phe | Pro | Lys | Cys | Asp | Val | Asn | Glu | Arg |
| 15 | | | | | 20 | | | | | 25 | | | | | 30 |
| TTC | GAG | GTG | TGT | GGC | AAT | CTG | AAG | GAG | TGC | GAG | CTC | AAG | TGC | GAT | GAG | 147
| Phe | Glu | Val | Cys | Gly | Asn | Leu | Lys | Glu | Cys | Glu | Leu | Lys | Cys | Asp | Glu |
| | | | | 35 | | | | | 40 | | | | | 45 | |
| GAC | CCT | AAG | ATA | TGC | TCT | CGT | GCA | TGT | ATT | CGT | CCC | CCT | GCT | TGC | GTA | 195
| Asp | Pro | Lys | Ile | Cys | Ser | Arg | Ala | Cys | Ile | Arg | Pro | Pro | Ala | Cys | Val |
| | | 50 | | | | 55 | | | | | | 60 | | | |
| TGC | GAT | GAC | GGA | TTC | TAC | AGA | GAC | AAA | TAT | GGC | TTC | TGT | GTT | GAA | GAA | 243
| Cys | Asp | Asp | Gly | Phe | Tyr | Arg | Asp | Lys | Tyr | Gly | Phe | Cys | Val | Glu | Glu |
| | | 65 | | | | 70 | | | | | 75 | | | | |
| GAC | GAA | TGT | AAC | GAT | ATG | GAG | ATT | ATT | ACT | TTT | CCA | CCA | GAA | ACC | AAA TG | 293
| Asp | Glu | Cys | Asn | Asp | Met | Glu | Ile | Ile | Thr | Phe | Pro | Pro | Glu | Thr | Lys |
| | 80 | | | | | 85 | | | | | | 90 | | | |

ATGACCGAAG CTTCCACCTT TCTATACATA TCTTCACTGC TTGACAGGCT TCTCGACAAT    353

TTAGAAGTTC TGCTTGACTT TGTCTATTTG AAATTGTTCA CACTAATGGG GGAAGTAAAG    413

CATTTTCACG AC    425

( 2 ) INFORMATION FOR SEQ ID NO: 40:

( i ) SEQUENCE CHARACTERISTICS:
        ( A ) LENGTH: 471 base pairs
        ( B ) TYPE: nucleic acid
        ( C ) STRANDEDNESS: single
        ( D ) TOPOLOGY: linear ( i x ) FEATURE:

(A) NAME/KEY: Coding Sequence
(B) LOCATION: 23...310
(D) OTHER INFORMATION:

(xi) SEQUENCE DESCRIPTION: SEQ ID NO: 40:

| | | | | | | | | | | | | | | | | |
|---|---|---|---|---|---|---|---|---|---|---|---|---|---|---|---|---|
| GAATTCCGCT | ACATTTCAA | CA | ATG<br>Met<br>1 | TCG<br>Ser | ACG<br>Thr | CTT<br>Leu | TAT<br>Tyr<br>5 | GTT<br>Val | ATC<br>Ile | GCA<br>Ala | ATA<br>Ile | TGT<br>Cys<br>10 | | | | 52 |
| TTG<br>Leu | CTG<br>Leu | CTT<br>Leu | GTT<br>Val | TCG<br>Ser<br>15 | CAA<br>Gln | TGC<br>Cys | AAT<br>Asn | GGA<br>Gly | AGA<br>Arg<br>20 | ACG<br>Thr | GTG<br>Val | AAG<br>Lys | AAG<br>Lys<br>25 | TGT<br>Cys | GGC<br>Gly | 100 |
| AAG<br>Lys | AAT<br>Asn | GAA<br>Glu | AGA<br>Arg<br>30 | TAC<br>Tyr | GAC<br>Asp | GAC<br>Asp | TGT<br>Cys | GGC<br>Gly<br>35 | AAT<br>Asn | GCA<br>Ala | AAG<br>Lys | GAC<br>Asp | TGC<br>Cys<br>40 | GAG<br>Glu | ACC<br>Thr | 148 |
| AAG<br>Lys | TGC<br>Cys | GGT<br>Gly<br>45 | GAA<br>Glu | GAG<br>Glu | GAA<br>Glu | AAG<br>Lys | GTG<br>Val<br>50 | TGC<br>Cys | CGT<br>Arg | TCG<br>Ser | CGT<br>Arg | GAG<br>Glu<br>55 | TGT<br>Cys | ACT<br>Thr | AGT<br>Ser | 196 |
| CCT<br>Pro | GGT<br>Gly<br>60 | GCC<br>Ala | TGC<br>Cys | GTA<br>Val | TGC<br>Cys | GAA<br>Glu<br>65 | CAA<br>Gln | GGA<br>Gly | TTC<br>Phe | TAC<br>Tyr | AGA<br>Arg<br>70 | GAT<br>Asp | CCG<br>Pro | GCT<br>Ala | GGC<br>Gly | 244 |
| GAC<br>Asp<br>75 | TGT<br>Cys | GTC<br>Val | ACT<br>Thr | GAT<br>Asp | GAA<br>Glu<br>80 | GAA<br>Glu | TGT<br>Cys | GAT<br>Asp | GAA<br>Glu | TGG<br>Trp<br>85 | AAC<br>Asn | AAT<br>Asn | ATG<br>Met | GAG<br>Glu | ATC<br>Ile<br>90 | 292 |
| ATT<br>Ile | ACT<br>Thr | ATG<br>Met | CCA<br>Pro | AAA<br>Lys<br>95 | CAG<br>Gln | TAGTGCGAAG | TTCCCTTCTT | TCTCCAAATC | TGCTCCGTG | | | | | | | 349 |
| CTCAATTATC | ACACACCTCC | ACTAGTTAAG | ATTGACTGAC | TCTCTTGCAT | TGTAGTATTT | | | | | | | | | | | 409 |
| TCGCTTGACT | CTGTGCATTT | AAGCATGAGA | TACTACTAGG | GAGAATAAAA | ATTACTAACT | | | | | | | | | | | 469 |
| AC | | | | | | | | | | | | | | | | 471 |

(2) INFORMATION FOR SEQ ID NO: 41:

(i) SEQUENCE CHARACTERISTICS:
(A) LENGTH: 396 base pairs
(B) TYPE: nucleic acid
(C) STRANDEDNESS: single
(D) TOPOLOGY: linear (ix) FEATURE:
(A) NAME/KEY: Coding Sequence
(B) LOCATION: 10...237
(D) OTHER INFORMATION:

(xi) SEQUENCE DESCRIPTION: SEQ ID NO: 41:

| | | | | | | | | | | | | | | | |
|---|---|---|---|---|---|---|---|---|---|---|---|---|---|---|---|
| GAATTCCGG | AAA<br>Lys<br>1 | TGT<br>Cys | CCT<br>Pro | ACC<br>Thr | GAT<br>Asp<br>5 | GAA<br>Glu | TGG<br>Trp | TTC<br>Phe | GAT<br>Asp | TGG<br>Trp<br>10 | TGT<br>Cys | GGA<br>Gly | ACT<br>Thr | TAC<br>Tyr | 51 |
| AAG<br>Lys<br>15 | CAT<br>His | TGC<br>Cys | GAA<br>Glu | CTC<br>Leu<br>20 | AAG<br>Lys | TGC<br>Cys | GAT<br>Asp | AGG<br>Arg | GAG<br>Glu<br>25 | CTA<br>Leu | ACT<br>Thr | GAG<br>Glu | AAA<br>Lys | GAA<br>Glu | GAG<br>Glu<br>30 | 99 |
| CAG<br>Gln | GCA<br>Ala | TGT<br>Cys | CTC<br>Leu | TCA<br>Ser<br>35 | CGT<br>Arg | GTT<br>Val | TGT<br>Cys | GAG<br>Glu | AAG<br>Lys<br>40 | TCC<br>Ser | GCT<br>Ala | TGC<br>Cys | GTA<br>Val | TGC<br>Cys<br>45 | AAT<br>Asn | 147 |
| GAC<br>Asp | GGA<br>Gly | TTA<br>Leu | TAC<br>Tyr<br>50 | AGA<br>Arg | GAC<br>Asp | AAG<br>Lys | TTT<br>Phe | GGC<br>Gly<br>55 | AAC<br>Asn | TGT<br>Cys | GTT<br>Val | GAA<br>Glu | AAA<br>Lys<br>60 | GAC<br>Asp | GAA<br>Glu | 195 |
| TGC<br>Cys | AAC<br>Asn | GAT<br>Asp<br>65 | ATG<br>Met | GAG<br>Glu | ATT<br>Ile | ATT<br>Ile | ACT<br>Thr<br>70 | TTT<br>Phe | GCA<br>Ala | CCA<br>Pro | GAA<br>Glu | ACC<br>Thr<br>75 | AAA<br>Lys | TAATGGCCTA | | 247 |
| AGGTTCCAAA | CCTTGCTACA | CACCGTCAGT | GCTTACTGT | TTCCTCACG | TGTTAGTAGT | | | | | | | | | | | 307 |
| TTTGCTTGAC | TCTGTGTATT | TAAGCATTGT | CTACTAATGG | GCAAAGTAAA | GCATTGTAAG | | | | | | | | | | | 367 |

GACATAATAA TGAGTAAACC TTCTGATTT                                                                  396

( 2 ) INFORMATION FOR SEQ ID NO: 42:

( i ) SEQUENCE CHARACTERISTICS:
      ( A ) LENGTH: 688 base pairs
      ( B ) TYPE: nucleic acid
      ( C ) STRANDEDNESS: single
      ( D ) TOPOLOGY: linear ( i x ) FEATURE:
      ( A ) NAME/KEY: Coding Sequence
      ( B ) LOCATION: 21...560
      ( D ) OTHER INFORMATION:

( x i ) SEQUENCE DESCRIPTION: SEQ ID NO: 42:

```
GAATTCCGGG CGGCAGAAAG ATG CGA ATG CTC TAC CTT GTT CCT ATC TGG          50
                     Met Arg Met Leu Tyr Leu Val Pro Ile Trp
                      1               5                  10

TTG CTG CTC ATT TCG CTA TGC AGT GGA AAA GCT GCG AAG AAA TGT GGT        98
Leu Leu Leu Ile Ser Leu Cys Ser Gly Lys Ala Ala Lys Lys Cys Gly
             15                  20                  25

CTC AAT GAA AGG CTG GAC TGT GGC AAT CTG AAG CAA TGC GAG CCC AAG       146
Leu Asn Glu Arg Leu Asp Cys Gly Asn Leu Lys Gln Cys Glu Pro Lys
         30                  35                  40

TGC AGC GAC TTG GAA AGT GAG GAG TAT GAG GAG GAA GAT GAG TCG AAA       194
Cys Ser Asp Leu Glu Ser Glu Glu Tyr Glu Glu Glu Asp Glu Ser Lys
         45                  50                  55

TGT CGA TCA CGT GAA TGT TCT CGT CGT GTT TGT GTA TGC GAT GAA GGA       242
Cys Arg Ser Arg Glu Cys Ser Arg Arg Val Cys Val Cys Asp Glu Gly
     60                  65                  70

TTC TAC AGA AAC AAG AAG GGC AAG TGT GTT GCA AAA GAT GTT TGC GAG       290
Phe Tyr Arg Asn Lys Lys Gly Lys Cys Val Ala Lys Asp Val Cys Glu
 75                  80                  85                  90

GAC GAC AAT ATG GAG ATT ATC ACT TTT CCA CCA GAA GAC GAA TGT GGT       338
Asp Asp Asn Met Glu Ile Ile Thr Phe Pro Pro Glu Asp Glu Cys Gly
             95                 100                 105

CCC GAT GAA TGG TTC GAC TAC TGT GGA AAT TAT AAG AAG TGC GAA CGC       386
Pro Asp Glu Trp Phe Asp Tyr Cys Gly Asn Tyr Lys Lys Cys Glu Arg
            110                 115                 120

AAG TGC AGT GAG GAG ACA AGT GAG AAA AAT GAG GAG GCA TGC CTC TCT       434
Lys Cys Ser Glu Glu Thr Ser Glu Lys Asn Glu Glu Ala Cys Leu Ser
            125                 130                 135

CGT GCT TGT ACT GGT CGT GCT TGC GTA TGC AAA GAC GGA TTG TAC AGA       482
Arg Ala Cys Thr Gly Arg Ala Cys Val Cys Lys Asp Gly Leu Tyr Arg
        140                 145                 150

GAC GAC TTT GGC AAC TGT GTT CCA CAT GAC GAA TGC AAC GAT ATG GAG       530
Asp Asp Phe Gly Asn Cys Val Pro His Asp Glu Cys Asn Asp Met Glu
155                 160                 165                 170

ATC ATC ACT TTT CCA CCG GAA ACC AAA CAT TGACCAGAGG CTCCAACTCT CGCT    584
Ile Ile Thr Phe Pro Pro Glu Thr Lys His
                175                 180

ACACAACGTC AGGGCTAGAA TGGCCCCTCT GCGAGTTAGT AGTTTTGCTT GACTCTGCTT    644

ATTTGAGCAC TTTCTATTGA TGGCGAAAAT AAAGCATTTA AAAC                      688
```

( 2 ) INFORMATION FOR SEQ ID NO: 43:

( i ) SEQUENCE CHARACTERISTICS:
      ( A ) LENGTH: 349 base pairs
      ( B ) TYPE: nucleic acid
      ( C ) STRANDEDNESS: single
      ( D ) TOPOLOGY: linear ( i x ) FEATURE:

(A) NAME/KEY: Coding Sequence
            (B) LOCATION: 49...276
            (D) OTHER INFORMATION:

(xi) SEQUENCE DESCRIPTION: SEQ ID NO: 43:

GAATTCCGCG CACCTGAGAG GTGAGCTACG CAAGTCTTCG CTGGTACA ATG ATC CGA                 57
                                                      Met Ile Arg
                                                       1

AAG CTC GTT CTG CTG ACT GCT ATC GTC ACG GTG GTG CTA AGT GCG AAG                 105
Lys Leu Val Leu Leu Thr Ala Ile Val Thr Val Val Leu Ser Ala Lys
     5              10                  15

ACC TGT GGA CCA AAC GAG GAG TAC ACT GAA TGC GGG ACG CCA TGC GAG                 153
Thr Cys Gly Pro Asn Glu Glu Tyr Thr Glu Cys Gly Thr Pro Cys Glu
 20              25                  30                      35

CCG AAG TGC AAT GAA CCG ATG CCA GAC ATC TGT ACT CTG AAC TGC ATC                 201
Pro Lys Cys Asn Glu Pro Met Pro Asp Ile Cys Thr Leu Asn Cys Ile
             40                  45                  50

GTG AAC GTG TGT CAG TGC AAA CCC GGC TTC AAG CGC GGA CCG AAA GGA                 249
Val Asn Val Cys Gln Cys Lys Pro Gly Phe Lys Arg Gly Pro Lys Gly
                 55              60                  65

TGC GTC GCC CCC GGA CCA GGC TGT AAA TAGTTCTCCA CCTGCCCTTT CGTTGGAA              304
Cys Val Ala Pro Gly Pro Gly Cys Lys
             70              75

CAAATGGCTG TCTTTTTACA TTCTGAATCA ATAAAGCCGA ACGGT                               349

(2) INFORMATION FOR SEQ ID NO: 44:

(i) SEQUENCE CHARACTERISTICS:
            (A) LENGTH: 432 base pairs
            (B) TYPE: nucleic acid
            (C) STRANDEDNESS: single
            (D) TOPOLOGY: linear (ix) FEATURE:
            (A) NAME/KEY: Coding Sequence
            (B) LOCATION: 40...393
            (D) OTHER INFORMATION:

(xi) SEQUENCE DESCRIPTION: SEQ ID NO: 44:

AAGCTTTGCT AACATACTGC GTAATAAGGA GTCTTAATC ATG CCA GTT CTT TTG                  54
                                             Met Pro Val Leu Leu
                                              1               5

GGT ATT CCG TTA TTA TTG CGT TTC CTC GGT TTC CTT CTG GTA ACT TTG                 102
Gly Ile Pro Leu Leu Leu Arg Phe Leu Gly Phe Leu Leu Val Thr Leu
             10                  15                      20

TTC GGC TAT CTG CTT ACT TTC CTT AAA AAG GGC TTC GGT AAG ATA GCT                 150
Phe Gly Tyr Leu Leu Thr Phe Leu Lys Lys Gly Phe Gly Lys Ile Ala
             25                  30                  35

ATT GCT ATT TCA TTG TTT CTT GCT CTT ATT ATT GGG CTT AAC TCA ATT                 198
Ile Ala Ile Ser Leu Phe Leu Ala Leu Ile Ile Gly Leu Asn Ser Ile
             40                  45                  50

CTT GTG GGT TAT CTC TCT GAT ATT AGC GCA CAA TTA CCC TCT GAT TTT                 246
Leu Val Gly Tyr Leu Ser Asp Ile Ser Ala Gln Leu Pro Ser Asp Phe
     55                  60                  65

GTT CAG GGC GTT CAG TTA ATT CTC CCG TCT AAT GCG CTT CCC TGT TTT                 294
Val Gln Gly Val Gln Leu Ile Leu Pro Ser Asn Ala Leu Pro Cys Phe
 70                  75                  80                  85

TAT GTT ATT CTC TCT GTA AAG GCT GCT ATT TTC ATT TTT GAC GTT AAA                 342
Tyr Val Ile Leu Ser Val Lys Ala Ala Ile Phe Ile Phe Asp Val Lys
                 90                  95                 100

CAA AAA ATC GTT TCT TAT TTG GAT TGG GAT AAA GGT GGA GGC TCA GGC                 390
Gln Lys Ile Val Ser Tyr Leu Asp Trp Asp Lys Gly Gly Gly Ser Gly
             105                 110                 115

```
GGA  GGCCAAGTCG  GCCATCCCAT  ATCACGCGGC  CGCGGATCC                                              432
Gly
```

( 2 ) INFORMATION FOR SEQ ID NO: 45:

( i ) SEQUENCE CHARACTERISTICS:
        ( A ) LENGTH: 433 base pairs
        ( B ) TYPE: nucleic acid
        ( C ) STRANDEDNESS: single
        ( D ) TOPOLOGY: linear ( i x ) FEATURE:
        ( A ) NAME/KEY: Coding Sequence
        ( B ) LOCATION: 40...393
        ( D ) OTHER INFORMATION:

( x i ) SEQUENCE DESCRIPTION: SEQ ID NO: 45:

```
AAGCTTTGCT  AACATACTGC  GTAATAAGGA  GTCTTAATC  ATG  CCA  GTT  CTT  TTG                           54
                                                    Met  Pro  Val  Leu  Leu
                                                    1                    5

GGT  ATT  CCG  TTA  TTA  TTG  CGT  TTC  CTC  GGT  TTC  CTT  CTG  GTA  ACT  TTG                  102
Gly  Ile  Pro  Leu  Leu  Leu  Arg  Phe  Leu  Gly  Phe  Leu  Leu  Val  Thr  Leu
               10                       15                      20

TTC  GGC  TAT  CTG  CTT  ACT  TTC  CTT  AAA  AAG  GGC  TTC  GGT  AAG  ATA  GCT                  150
Phe  Gly  Tyr  Leu  Leu  Thr  Phe  Leu  Lys  Lys  Gly  Phe  Gly  Lys  Ile  Ala
               25                       30                      35

ATT  GCT  ATT  TCA  TTG  TTT  CTT  GCT  CTT  ATT  ATT  GGG  CTT  AAC  TCA  ATT                  198
Ile  Ala  Ile  Ser  Leu  Phe  Leu  Ala  Leu  Ile  Ile  Gly  Leu  Asn  Ser  Ile
               40                       45                      50

CTT  GTG  GGT  TAT  CTC  TCT  GAT  ATT  AGC  GCA  CAA  TTA  CCC  TCT  GAT  TTT                  246
Leu  Val  Gly  Tyr  Leu  Ser  Asp  Ile  Ser  Ala  Gln  Leu  Pro  Ser  Asp  Phe
          55                       60                      65

GTT  CAG  GGC  GTT  CAG  TTA  ATT  CTC  CCG  TCT  AAT  GCG  CTT  CCC  TGT  TTT                  294
Val  Gln  Gly  Val  Gln  Leu  Ile  Leu  Pro  Ser  Asn  Ala  Leu  Pro  Cys  Phe
70                       75                      80                       85

TAT  GTT  ATT  CTC  TCT  GTA  AAG  GCT  GCT  ATT  TTC  ATT  TTT  GAC  GTT  AAA                  342
Tyr  Val  Ile  Leu  Ser  Val  Lys  Ala  Ala  Ile  Phe  Ile  Phe  Asp  Val  Lys
                    90                       95                      100

CAA  AAA  ATC  GTT  TCT  TAT  TTG  GAT  TGG  GAT  AAA  GGT  GGA  GGC  TCA  GGC                  390
Gln  Lys  Ile  Val  Ser  Tyr  Leu  Asp  Trp  Asp  Lys  Gly  Gly  Gly  Ser  Gly
               105                      110                     115

GGA  GGGCCAAGTC  GGCCATCCCA  TATCACGCGG  CCGCGGATCC                                             43
Gly
```

( 2 ) INFORMATION FOR SEQ ID NO: 46:

( i ) SEQUENCE CHARACTERISTICS:
        ( A ) LENGTH: 434 base pairs
        ( B ) TYPE: nucleic acid
        ( C ) STRANDEDNESS: single
        ( D ) TOPOLOGY: linear ( i x ) FEATURE:
        ( A ) NAME/KEY: Coding Sequence
        ( B ) LOCATION: 40...393
        ( D ) OTHER INFORMATION:

( x i ) SEQUENCE DESCRIPTION: SEQ ID NO: 46:

```
AAGCTTTGCT  AACATACTGC  GTAATAAGGA  GTCTTAATC  ATG  CCA  GTT  CTT  TTG                           54
                                                    Met  Pro  Val  Leu  Leu

GGT  ATT  CCG  TTA  TTA  TTG  CGT  TTC  CTC  GGT  TTC  CTT  CTG  GTA  ACT  TTG                  102
Gly  Ile  Pro  Leu  Leu  Leu  Arg  Phe  Leu  Gly  Phe  Leu  Leu  Val  Thr  Leu
               10                       15                      20

TTC  GGC  TAT  CTG  CTT  ACT  TTC  CTT  AAA  AAG  GGC  TTC  GGT  AAG  ATA  GCT                  150
Phe  Gly  Tyr  Leu  Leu  Thr  Phe  Leu  Lys  Lys  Gly  Phe  Gly  Lys  Ile  Ala
               25                       30                      35
```

```
ATT  GCT  ATT  TCA  TTG  TTT  CTT  GCT  CTT  ATT  ATT  GGG  CTT  AAC  TCA  ATT        198
Ile  Ala  Ile  Ser  Leu  Phe  Leu  Ala  Leu  Ile  Ile  Gly  Leu  Asn  Ser  Ile
          40                            45                       50

CTT  GTG  GGT  TAT  CTC  TCT  GAT  ATT  AGC  GCA  CAA  TTA  CCC  TCT  GAT  TTT        246
Leu  Val  Gly  Tyr  Leu  Ser  Asp  Ile  Ser  Ala  Gln  Leu  Pro  Ser  Asp  Phe
     55                            60                       65

GTT  CAG  GGC  GTT  CAG  TTA  ATT  CTC  CCG  TCT  AAT  GCG  CTT  CCC  TGT  TTT        294
Val  Gln  Gly  Val  Gln  Leu  Ile  Leu  Pro  Ser  Asn  Ala  Leu  Pro  Cys  Phe
70                       75                       80                       85

TAT  GTT  ATT  CTC  TCT  GTA  AAG  GCT  GCT  ATT  TTC  ATT  TTT  GAC  GTT  AAA        342
Tyr  Val  Ile  Leu  Ser  Val  Lys  Ala  Ala  Ile  Phe  Ile  Phe  Asp  Val  Lys
               90                            95                      100

CAA  AAA  ATC  GTT  TCT  TAT  TTG  GAT  TGG  GAT  AAA  GGT  GGA  GGC  TCA  GGC        390
Gln  Lys  Ile  Val  Ser  Tyr  Leu  Asp  Trp  Asp  Lys  Gly  Gly  Gly  Ser  Gly
               105                           110                     115

GGA  TCGGCCAAGT  CGGCCATCCC  ATATCACGCG  GCCGCGGATC  C                                434
Gly
```

( 2 ) INFORMATION FOR SEQ ID NO: 47:

( i ) SEQUENCE CHARACTERISTICS:
      ( A ) LENGTH: 430 base pairs
      ( B ) TYPE: nucleic acid
      ( C ) STRANDEDNESS: single
      ( D ) TOPOLOGY: linear ( i x ) FEATURE:
      ( A ) NAME/KEY: Coding Sequence
      ( B ) LOCATION: 10...282
      ( D ) OTHER INFORMATION:

( x i ) SEQUENCE DESCRIPTION: SEQ ID NO: 47:

```
GAATTCCGG  CTG  GTW  TCC  TAC  TGC  AGT  GGA  AAA  GCA  ACG  ATG  CAG  TGT  GGT        51
           Leu  Val  Ser  Tyr  Cys  Ser  Gly  Lys  Ala  Thr  Met  Gln  Cys  Gly
           1                   5                             10

GAG  AAT  GAA  AAG  TAC  GAT  TCG  TGC  GGT  AGC  AAG  GAG  TGC  GAT  AAG  AAG        99
Glu  Asn  Glu  Lys  Tyr  Asp  Ser  Cys  Gly  Ser  Lys  Glu  Cys  Asp  Lys  Lys
15                       20                       25                       30

TGC  AAA  TAT  GAC  GGA  GTT  GAG  GAG  GAA  GAC  GAC  GAG  GAA  CCT  AAT  GTG        147
Cys  Lys  Tyr  Asp  Gly  Val  Glu  Glu  Glu  Asp  Asp  Glu  Glu  Pro  Asn  Val
               35                            40                      45

CCA  TGC  CTA  GTA  CGT  GTG  TGT  CAT  CAA  GAT  TGC  GTA  TGC  GAA  GAA  GGA        195
Pro  Cys  Leu  Val  Arg  Val  Cys  His  Gln  Asp  Cys  Val  Cys  Glu  Glu  Gly
               50                            55                      60

TTC  TAT  AGA  AAC  AAA  GAT  GAC  AAA  TGT  GTA  TCA  GCA  GAA  GAC  TGC  GAA        243
Phe  Tyr  Arg  Asn  Lys  Asp  Asp  Lys  Cys  Val  Ser  Ala  Glu  Asp  Cys  Glu
               65                            70                      75

CTT  GAC  AAT  ATG  GAC  TTT  ATA  TAT  CCC  GGA  ACT  CGA  AAC  TGAACGAAGG  CTC      295
Leu  Asp  Asn  Met  Asp  Phe  Ile  Tyr  Pro  Gly  Thr  Arg  Asn
               80                            85                      90

CATTCTTGCT  GCACAAGATC  GATTGTCTCT  CCCCTGCATC  TCAGTAGTTT  TGCTACATTG               355

TATATGGTAG  CAAAAAATTA  GCTTAGGGAG  AATAAAATCT  TTACCTATAT  TTAATCAATG               415

AAGTATTCTC  TTTCT                                                                      430
```

( 2 ) INFORMATION FOR SEQ ID NO: 48:

( i ) SEQUENCE CHARACTERISTICS:
      ( A ) LENGTH: 100 amino acids
      ( B ) TYPE: amino acid
      ( D ) TOPOLOGY: linear ( x i ) SEQUENCE DESCRIPTION: SEQ ID NO: 48:

```
Met  Lys  Met  Leu  Tyr  Ala  Ile  Ala  Ile  Met  Phe  Leu  Leu  Val  Ser  Leu
```

```
              1                    5                        10                        15
Cys   Ser   Ala   Arg   Thr   Val   Arg   Lys   Ala   Tyr   Pro   Glu   Cys   Gly   Glu   Asn
                        20                        25                        30

Glu   Trp   Leu   Asp   Asp   Cys   Gly   Thr   Gln   Lys   Pro   Cys   Glu   Ala   Lys   Cys
                        35                        40                        45

Asn   Glu   Glu   Pro   Pro   Glu   Glu   Glu   Asp   Pro   Ile   Cys   Arg   Ser   Arg   Gly
                  50                        55                        60
Cys   Leu   Leu   Pro   Pro   Ala   Cys   Val   Cys   Lys   Asp   Gly   Phe   Tyr   Arg   Asp
 65                           70                        75                              80

Thr   Val   Ile   Gly   Asp   Cys   Val   Arg   Glu   Glu   Glu   Cys   Asp   Gln   His   Glu
                        85                        90                              95

Ile   Ile   His   Val
                  100
```

(2) INFORMATION FOR SEQ ID NO: 49:

(i) SEQUENCE CHARACTERISTICS:
        (A) LENGTH: 98 amino acids
        (B) TYPE: amino acid
        (D) TOPOLOGY: linear (xi) SEQUENCE DESCRIPTION: SEQ ID NO: 49:

```
Met   Lys   Met   Leu   Tyr   Ala   Ile   Ala   Ile   Met   Phe   Leu   Leu   Val   Ser   Leu
 1                            5                        10                              15

Cys   Ser   Thr   Arg   Thr   Val   Arg   Lys   Ala   Tyr   Pro   Glu   Cys   Gly   Glu   Asn
                        20                        25                        30

Glu   Trp   Leu   Asp   Val   Cys   Gly   Thr   Lys   Lys   Pro   Cys   Glu   Ala   Lys   Cys
                  35                        40                        45

Ser   Glu   Glu   Glu   Glu   Glu   Asp   Pro   Ile   Cys   Arg   Ser   Phe   Ser   Cys   Pro
      50                        55                        60

Gly   Pro   Ala   Ala   Cys   Val   Cys   Glu   Asp   Gly   Phe   Tyr   Arg   Asp   Thr   Val
 65                           70                        75                              80

Ile   Gly   Asp   Cys   Val   Lys   Glu   Glu   Glu   Cys   Asp   Gln   His   Glu   Ile   Ile
                        85                        90                              95

His   Val
```

(2) INFORMATION FOR SEQ ID NO: 50:

(i) SEQUENCE CHARACTERISTICS:
        (A) LENGTH: 91 amino acids
        (B) TYPE: amino acid
        (D) TOPOLOGY: linear (xi) SEQUENCE DESCRIPTION: SEQ ID NO: 50:

```
Leu   Val   Ser   Tyr   Cys   Ser   Gly   Lys   Ala   Thr   Met   Gln   Cys   Gly   Glu   Asn
 1                            5                        10                              15

Glu   Lys   Tyr   Asp   Ser   Cys   Gly   Ser   Lys   Glu   Cys   Asp   Lys   Lys   Cys   Lys
                  20                        25                        30

Tyr   Asp   Gly   Val   Glu   Glu   Asp   Asp   Glu   Glu   Pro   Asn   Val   Pro   Cys
                  35                        40                        45

Leu   Val   Arg   Val   Cys   His   Gln   Asp   Cys   Val   Cys   Glu   Glu   Gly   Phe   Tyr
            50                        55                        60

Arg   Asn   Lys   Asp   Asp   Lys   Cys   Val   Ser   Ala   Glu   Asp   Cys   Glu   Leu   Asp
 65                           70                        75                              80

Asn   Met   Asp   Phe   Ile   Tyr   Pro   Gly   Thr   Arg   Asn
                        85                        90
```

(2) INFORMATION FOR SEQ ID NO: 51:

( i ) SEQUENCE CHARACTERISTICS:
  ( A ) LENGTH: 94 amino acids
  ( B ) TYPE: amino acid
  ( D ) TOPOLOGY: linear ( x i ) SEQUENCE DESCRIPTION: SEQ ID NO: 51:

| Met | Arg | Thr | Leu | Tyr | Leu | Ile | Ser | Ile | Trp | Leu | Phe | Leu | Ile | Ser | Gln |
|---|---|---|---|---|---|---|---|---|---|---|---|---|---|---|---|
| 1 | | | | 5 | | | | | 10 | | | | | 15 | |
| Cys | Asn | Gly | Lys | Ala | Phe | Pro | Lys | Cys | Asp | Val | Asn | Glu | Arg | Phe | Glu |
| | | | | 20 | | | | | 25 | | | | | 30 | |
| Val | Cys | Gly | Asn | Leu | Lys | Glu | Cys | Glu | Leu | Lys | Cys | Asp | Glu | Asp | Pro |
| | | | 35 | | | | | 40 | | | | | 45 | | |
| Lys | Ile | Cys | Ser | Arg | Ala | Cys | Ile | Arg | Pro | Pro | Ala | Cys | Val | Cys | Asp |
| | | | 50 | | | | | 55 | | | | | 60 | | |
| Asp | Gly | Phe | Tyr | Arg | Asp | Lys | Tyr | Gly | Phe | Cys | Val | Glu | Glu | Asp | Glu |
| 65 | | | | | 70 | | | | | 75 | | | | | 80 |
| Cys | Asn | Asp | Met | Glu | Ile | Ile | Thr | Phe | Pro | Pro | Glu | Thr | Lys | | |
| | | | | 85 | | | | | 90 | | | | | | |

( 2 ) INFORMATION FOR SEQ ID NO: 52:

( i ) SEQUENCE CHARACTERISTICS:
  ( A ) LENGTH: 96 amino acids
  ( B ) TYPE: amino acid
  ( D ) TOPOLOGY: linear ( x i ) SEQUENCE DESCRIPTION: SEQ ID NO: 52:

| Met | Ser | Thr | Leu | Tyr | Val | Ile | Ala | Ile | Cys | Leu | Leu | Leu | Val | Ser | Gln |
|---|---|---|---|---|---|---|---|---|---|---|---|---|---|---|---|
| 1 | | | | 5 | | | | | 10 | | | | | 15 | |
| Cys | Asn | Gly | Arg | Thr | Val | Lys | Lys | Cys | Gly | Lys | Asn | Glu | Arg | Tyr | Asp |
| | | | | 20 | | | | | 25 | | | | | 30 | |
| Asp | Cys | Gly | Asn | Ala | Lys | Asp | Cys | Glu | Thr | Lys | Cys | Gly | Glu | Glu | Glu |
| | | | 35 | | | | | 40 | | | | | 45 | | |
| Lys | Val | Cys | Arg | Ser | Arg | Glu | Cys | Thr | Ser | Pro | Gly | Ala | Cys | Val | Cys |
| | | | 50 | | | | | 55 | | | | | 60 | | |
| Glu | Gln | Gly | Phe | Tyr | Arg | Asp | Pro | Ala | Gly | Asp | Cys | Val | Thr | Asp | Glu |
| 65 | | | | | 70 | | | | | 75 | | | | | 80 | |
| Glu | Cys | Asp | Glu | Trp | Asn | Asn | Met | Glu | Ile | Ile | Thr | Met | Pro | Lys | Gln |
| | | | | 85 | | | | | 90 | | | | | 95 | |

( 2 ) INFORMATION FOR SEQ ID NO: 53:

( i ) SEQUENCE CHARACTERISTICS:
  ( A ) LENGTH: 108 amino acids
  ( B ) TYPE: amino acid
  ( D ) TOPOLOGY: linear ( x i ) SEQUENCE DESCRIPTION: SEQ ID NO: 53:

| Met | Ala | Val | Leu | Tyr | Ser | Val | Ala | Ile | Ala | Leu | Leu | Leu | Val | Ser | Gln |
|---|---|---|---|---|---|---|---|---|---|---|---|---|---|---|---|
| 1 | | | | 5 | | | | | 10 | | | | | 15 | |
| Cys | Ser | Gly | Lys | Pro | Asn | Asn | Val | Met | Thr | Asn | Ala | Cys | Gly | Leu | Asn |
| | | | | 20 | | | | | 25 | | | | | 30 | |
| Glu | Tyr | Phe | Ala | Glu | Cys | Gly | Asn | Met | Lys | Glu | Cys | Glu | His | Arg | Cys |
| | | | 35 | | | | | 40 | | | | | 45 | | |
| Asn | Glu | Glu | Glu | Asn | Glu | Glu | Arg | Asp | Glu | Glu | Arg | Ile | Thr | Ala | Cys |
| | | | 50 | | | | | 55 | | | | | 60 | | |
| Leu | Ile | Arg | Val | Cys | Phe | Arg | Pro | Gly | Ala | Cys | Val | Cys | Lys | Asp | Gly |
| 65 | | | | | 70 | | | | | 75 | | | | | 80 | |
| Phe | Tyr | Arg | Asn | Arg | Thr | Gly | Ser | Cys | Val | Glu | Glu | Asp | Asp | Cys | Glu |
| | | | | 85 | | | | | 90 | | | | | 95 | |

Tyr Glu Asn Met Glu Phe Ile Thr Phe Ala Pro Glu
                100                 105

(2) INFORMATION FOR SEQ ID NO: 54:

(i) SEQUENCE CHARACTERISTICS:
        (A) LENGTH: 82 amino acids
        (B) TYPE: amino acid
        (D) TOPOLOGY: linear (xi) SEQUENCE DESCRIPTION: SEQ ID NO: 54:

Val Pro Ile Cys Gly Ser Asn Glu Arg Tyr Ser Asp Cys Gly Asn Asp
 1               5                  10                  15
Lys Gln Cys Glu Arg Lys Cys Asn Glu Asp Asp Tyr Glu Lys Gly Asp
            20                  25                  30
Glu Ala Cys Arg Ser His Val Cys Glu Arg Pro Gly Ala Cys Val Cys
            35                  40                  45
Glu Asp Gly Phe Tyr Arg Asn Lys Lys Gly Ser Cys Val Glu Ser Asp
        50                  55                  60
Asp Cys Glu Tyr Asp Asn Met Asp Phe Ile Thr Phe Ala Pro Glu Thr
65                  70                  75                  80
Ser Arg (2) INFORMATION FOR SEQ ID NO: 55:

(i) SEQUENCE CHARACTERISTICS:
        (A) LENGTH: 76 amino acids
        (B) TYPE: amino acid
        (D) TOPOLOGY: linear (xi) SEQUENCE DESCRIPTION: SEQ ID NO: 55:

Lys Cys Pro Thr Asp Glu Trp Phe Asp Trp Cys Gly Thr Tyr Lys His
 1               5                  10                  15
Cys Glu Leu Lys Cys Asp Arg Glu Leu Thr Glu Lys Glu Glu Gln Ala
            20                  25                  30
Cys Leu Ser Arg Val Cys Glu Lys Ser Ala Cys Val Cys Asn Asp Gly
            35                  40                  45
Leu Tyr Arg Asp Lys Phe Gly Asn Cys Val Glu Lys Asp Glu Cys Asn
        50                  55                  60
Asp Met Glu Ile Ile Thr Phe Ala Pro Glu Thr Lys
65                  70                  75

(2) INFORMATION FOR SEQ ID NO: 56:

(i) SEQUENCE CHARACTERISTICS:
        (A) LENGTH: 102 amino acids
        (B) TYPE: amino acid
        (D) TOPOLOGY: linear (xi) SEQUENCE DESCRIPTION: SEQ ID NO: 56:

Met Arg Met Leu Tyr Leu Val Pro Ile Trp Leu Leu Leu Ile Ser Leu
 1               5                  10                  15
Cys Ser Gly Lys Ala Ala Lys Lys Cys Gly Leu Asn Glu Arg Leu Asp
            20                  25                  30
Cys Gly Asn Leu Lys Gln Cys Glu Pro Lys Cys Ser Asp Leu Glu Ser
            35                  40                  45
Glu Glu Tyr Glu Glu Glu Asp Glu Ser Lys Cys Arg Ser Arg Glu Cys
        50                  55                  60
Ser Arg Arg Val Cys Val Cys Asp Glu Gly Phe Tyr Arg Asn Lys Lys
65                  70                  75                  80

| Gly | Lys | Cys | Val | Ala | Lys | Asp | Val | Cys | Glu | Asp | Asp | Asn | Met | Glu | Ile |
|---|---|---|---|---|---|---|---|---|---|---|---|---|---|---|---|
| | | | | 85 | | | | 90 | | | | | | 95 | |

Ile Thr Phe Pro Pro Glu
              100

(2) INFORMATION FOR SEQ ID NO: 57:

(i) SEQUENCE CHARACTERISTICS:
        (A) LENGTH: 78 amino acids
        (B) TYPE: amino acid
        (D) TOPOLOGY: linear (xi) SEQUENCE DESCRIPTION: SEQ ID NO: 57:

Asp Glu Cys Gly Pro Asp Glu Trp Phe Asp Tyr Cys Gly Asn Tyr Lys
 1               5                  10                  15
Lys Cys Glu Arg Lys Cys Ser Glu Glu Thr Ser Glu Lys Asn Glu Glu
             20                  25                  30
Ala Cys Leu Ser Arg Ala Cys Thr Gly Arg Ala Cys Val Cys Lys Asp
             35                  40                  45
Gly Leu Tyr Arg Asp Asp Phe Gly Asn Cys Val Pro His Asp Glu Cys
 50                  55                  60
Asn Asp Met Glu Ile Ile Thr Phe Pro Pro Glu Thr Lys His
 65                  70                  75

(2) INFORMATION FOR SEQ ID NO: 58:

(i) SEQUENCE CHARACTERISTICS:
        (A) LENGTH: 76 amino acids
        (B) TYPE: amino acid
        (D) TOPOLOGY: linear (xi) SEQUENCE DESCRIPTION: SEQ ID NO: 58:

Met Ile Arg Lys Leu Val Leu Leu Thr Ala Ile Val Thr Val Val Leu
 1               5                  10                  15
Ser Ala Lys Thr Cys Gly Pro Asn Glu Glu Tyr Thr Glu Cys Gly Thr
             20                  25                  30
Pro Cys Glu Pro Lys Cys Asn Glu Pro Met Pro Asp Ile Cys Thr Leu
             35                  40                  45
Asn Cys Ile Val Asn Val Cys Gln Cys Lys Pro Gly Phe Lys Arg Gly
 50                  55                  60
Pro Lys Gly Cys Val Ala Pro Gly Pro Gly Cys Lys
 65                  70                  75

(2) INFORMATION FOR SEQ ID NO: 59:

(i) SEQUENCE CHARACTERISTICS:
        (A) LENGTH: 187 base pairs
        (B) TYPE: nucleic acid
        (C) STRANDEDNESS: single
        (D) TOPOLOGY: linear (xi) SEQUENCE DESCRIPTION: SEQ ID NO: 59:

```
TTATTCGAAA CGATGTTCTC TCCAATTTTG TCCTTGGAAA TTATTTAGC TACTTTGCAA        60
TCTGTCTTCG CCCAGCCAGT TATCTCCACT ACCGTTGGTT CCGCTGCCGA GGGTTCTTTG      120
GACAAGAGGC CTATCCGCGG AATTCAGATC TGAATGCGGC CGCTCGAGAC TAGTGGATCC      180
TTAGACA                                                                187
```

(2) INFORMATION FOR SEQ ID NO: 60:

(i) SEQUENCE CHARACTERISTICS:

(A) LENGTH: 8 amino acids
(B) TYPE: amino acid
(D) TOPOLOGY: linear (v) FRAGMENT TYPE: internal fragment (ix) FEATURE:
(D) OTHER INFORMATION: Xaa in any location 2 to 8 is an amino acid.

(xi) SEQUENCE DESCRIPTION: SEQ ID NO: 60:

Cys Xaa Xaa Xaa Xaa Xaa Xaa Xaa
1               5

(2) INFORMATION FOR SEQ ID NO: 61:

(i) SEQUENCE CHARACTERISTICS:
(A) LENGTH: 7 amino acids
(B) TYPE: amino acid
(D) TOPOLOGY: linear (v) FRAGMENT TYPE: internal fragment (ix) FEATURE:
(D) OTHER INFORMATION: Xaa in any location 2 to 6 is an amino acid.

(xi) SEQUENCE DESCRIPTION: SEQ ID NO: 61:

Cys Xaa Xaa Xaa Xaa Xaa Cys
1               5

(2) INFORMATION FOR SEQ ID NO: 62:

(i) SEQUENCE CHARACTERISTICS:
(A) LENGTH: 6 amino acids
(B) TYPE: amino acid
(D) TOPOLOGY: linear (v) FRAGMENT TYPE: internal fragment (ix) FEATURE:
(D) OTHER INFORMATION: Xaa in any location 2 to 5 is an amino acid.

(xi) SEQUENCE DESCRIPTION: SEQ ID NO: 62:

Cys Xaa Xaa Xaa Xaa Cys
1               5

(2) INFORMATION FOR SEQ ID NO: 63:

(i) SEQUENCE CHARACTERISTICS:
(A) LENGTH: 5 amino acids
(B) TYPE: amino acid
(D) TOPOLOGY: linear (v) FRAGMENT TYPE: internal fragment (ix) FEATURE:
(D) OTHER INFORMATION: Xaa in any location 2 to 4 is an amino acid.

(xi) SEQUENCE DESCRIPTION: SEQ ID NO: 63:

Cys Xaa Xaa Xaa Cys
1               5

(2) INFORMATION FOR SEQ ID NO: 64:

(i) SEQUENCE CHARACTERISTICS:
(A) LENGTH: 4 amino acids
(B) TYPE: amino acid
(D) TOPOLOGY: linear ( v ) FRAGMENT TYPE: internal fragment ( i x ) FEATURE:
    ( D ) OTHER INFORMATION: Xaa in any location 2 to 3
    is an amino acid.

( x i ) SEQUENCE DESCRIPTION: SEQ ID NO: 64:

Cys Xaa Xaa Cys
1

( 2 ) INFORMATION FOR SEQ ID NO: 65:

( i ) SEQUENCE CHARACTERISTICS:
    ( A ) LENGTH: 21 amino acids
    ( B ) TYPE: amino acid
    ( D ) TOPOLOGY: linear ( v ) FRAGMENT TYPE: internal fragment ( i x ) FEATURE:
    ( D ) OTHER INFORMATION: Xaa in any location 1 to 3, or 5
    to 21 is an amino acid.

( x i ) SEQUENCE DESCRIPTION: SEQ ID NO: 65:

Xaa Xaa Xaa Cys Xaa Xaa Xaa Xaa Xaa Xaa Xaa Xaa Xaa Xaa Xaa Xaa
1               5                       10                      15

Xaa Xaa Xaa Xaa Xaa
            20

( 2 ) INFORMATION FOR SEQ ID NO: 66:

( i ) SEQUENCE CHARACTERISTICS:
    ( A ) LENGTH: 20 amino acids
    ( B ) TYPE: amino acid
    ( D ) TOPOLOGY: linear ( v ) FRAGMENT TYPE: internal fragment ( i x ) FEATURE:
    ( D ) OTHER INFORMATION: Xaa in any location 1 to 3, or 5
    to 20 is an amino acid.

( x i ) SEQUENCE DESCRIPTION: SEQ ID NO: 66:

Xaa Xaa Xaa Cys Xaa Xaa Xaa Xaa Xaa Xaa Xaa Xaa Xaa Xaa Xaa Xaa
1               5                       10                      15

Xaa Xaa Xaa Xaa
            20

( 2 ) INFORMATION FOR SEQ ID NO: 67:

( i ) SEQUENCE CHARACTERISTICS:
    ( A ) LENGTH: 19 amino acids
    ( B ) TYPE: amino acid
    ( D ) TOPOLOGY: linear ( v ) FRAGMENT TYPE: internal fragment ( i x ) FEATURE:
    ( D ) OTHER INFORMATION: Xaa in any location 1 to 3, or 5
    to 19 is an amino acid.

( x i ) SEQUENCE DESCRIPTION: SEQ ID NO: 67:

Xaa Xaa Xaa Cys Xaa Xaa Xaa Xaa Xaa Xaa Xaa Xaa Xaa Xaa Xaa Xaa
1               5                       10                      15

Xaa Xaa Xaa ( 2 ) INFORMATION FOR SEQ ID NO: 68:

( i ) SEQUENCE CHARACTERISTICS:

( A ) LENGTH: 18 amino acids
            ( B ) TYPE: amino acid
            ( D ) TOPOLOGY: linear ( v ) FRAGMENT TYPE: internal fragment ( i x ) FEATURE:
            ( D ) OTHER INFORMATION: Xaa in any location 1 to 3, or 5
                to 18 is an amino acid.

( x i ) SEQUENCE DESCRIPTION: SEQ ID NO: 68:

Xaa Xaa Xaa Cys Xaa Xaa Xaa Xaa Xaa Xaa Xaa Xaa Xaa Xaa Xaa Xaa
1               5                   1 0                 1 5
Xaa Xaa ( 2 ) INFORMATION FOR SEQ ID NO: 69:

( i ) SEQUENCE CHARACTERISTICS:
            ( A ) LENGTH: 17 amino acids
            ( B ) TYPE: amino acid
            ( D ) TOPOLOGY: linear ( i x ) FEATURE:
            ( D ) OTHER INFORMATION: Xaa in any location 1 to 3, or 5
                to 17 is an amino acid.

( v ) FRAGMENT TYPE: internal fragment ( x i ) SEQUENCE DESCRIPTION: SEQ ID NO: 69:

Xaa Xaa Xaa Cys Xaa Xaa Xaa Xaa Xaa Xaa Xaa Xaa Xaa Xaa Xaa Xaa
1               5                   1 0                 1 5
Xaa ( 2 ) INFORMATION FOR SEQ ID NO: 70:

( i ) SEQUENCE CHARACTERISTICS:
            ( A ) LENGTH: 16 amino acids
            ( B ) TYPE: amino acid
            ( D ) TOPOLOGY: linear ( v ) FRAGMENT TYPE: internal fragment ( i x ) FEATURE:
            ( D ) OTHER INFORMATION: Xaa in any location 1 to 3, or 5
                to 16 is an amino acid.

( x i ) SEQUENCE DESCRIPTION: SEQ ID NO: 70:

Xaa Xaa Xaa Cys Xaa Xaa Xaa Xaa Xaa Xaa Xaa Xaa Xaa Xaa Xaa Xaa
1               5                   1 0                 1 5

( 2 ) INFORMATION FOR SEQ ID NO: 71:

( i ) SEQUENCE CHARACTERISTICS:
            ( A ) LENGTH: 15 amino acids
            ( B ) TYPE: amino acid
            ( D ) TOPOLOGY: linear ( v ) FRAGMENT TYPE: internal fragment ( i x ) FEATURE:
            ( D ) OTHER INFORMATION: Xaa in any location 1 to 3, or 5
                to 15 is an amino acid.

( x i ) SEQUENCE DESCRIPTION: SEQ ID NO: 71:

Xaa Xaa Xaa Cys Xaa Xaa Xaa Xaa Xaa Xaa Xaa Xaa Xaa Xaa Xaa
1               5                   1 0                 1 5

( 2 ) INFORMATION FOR SEQ ID NO: 72:

( i ) SEQUENCE CHARACTERISTICS:

( A ) LENGTH: 14 amino acids
( B ) TYPE: amino acid
( D ) TOPOLOGY: linear ( v ) FRAGMENT TYPE: internal fragment ( i x ) FEATURE:
( D ) OTHER INFORMATION: Xaa in any location 1 to 3, or 5 to 14 is an amino acid.

( x i ) SEQUENCE DESCRIPTION: SEQ ID NO: 72:

Xaa Xaa Xaa Cys Xaa Xaa Xaa Xaa Xaa Xaa Xaa Xaa Xaa Xaa
1               5                   10

( 2 ) INFORMATION FOR SEQ ID NO: 73:

( i ) SEQUENCE CHARACTERISTICS:
( A ) LENGTH: 13 amino acids
( B ) TYPE: amino acid
( D ) TOPOLOGY: linear ( v ) FRAGMENT TYPE: internal fragment ( i x ) FEATURE:
( D ) OTHER INFORMATION: Xaa in any location 1 to 3, or 5 to 13 is an amino acid.

( x i ) SEQUENCE DESCRIPTION: SEQ ID NO: 73:

Xaa Xaa Xaa Cys Xaa Xaa Xaa Xaa Xaa Xaa Xaa Xaa Xaa
1               5                   10

( 2 ) INFORMATION FOR SEQ ID NO: 74:

( i ) SEQUENCE CHARACTERISTICS:
( A ) LENGTH: 12 amino acids
( B ) TYPE: amino acid
( D ) TOPOLOGY: linear ( v ) FRAGMENT TYPE: internal fragment ( i x ) FEATURE:
( D ) OTHER INFORMATION: Xaa in any location 1 to 3, or 5 to 12 is an amino acid.

( x i ) SEQUENCE DESCRIPTION: SEQ ID NO: 74:

Xaa Xaa Xaa Cys Xaa Xaa Xaa Xaa Xaa Xaa Xaa Xaa
1               5                   10

( 2 ) INFORMATION FOR SEQ ID NO: 75:

( i ) SEQUENCE CHARACTERISTICS:
( A ) LENGTH: 11 amino acids
( B ) TYPE: amino acid
( D ) TOPOLOGY: linear ( i x ) FEATURE:
( D ) OTHER INFORMATION: Xaa in any location 1 to 3, or 5 to 11 is an amino acid.

( v ) FRAGMENT TYPE: internal fragment ( x i ) SEQUENCE DESCRIPTION: SEQ ID NO: 75:

Xaa Xaa Xaa Cys Xaa Xaa Xaa Xaa Xaa Xaa Xaa
1               5                   10

( 2 ) INFORMATION FOR SEQ ID NO: 76:

( i ) SEQUENCE CHARACTERISTICS:
( A ) LENGTH: 10 amino acids
( B ) TYPE: amino acid
( D ) TOPOLOGY: linear (v) FRAGMENT TYPE: internal fragment (ix) FEATURE:
(D) OTHER INFORMATION: Xaa in any location 1 to 3, or 5 to 10 is an amino acid.

(xi) SEQUENCE DESCRIPTION: SEQ ID NO: 76:

Xaa Xaa Xaa Cys Xaa Xaa Xaa Xaa Xaa Xaa
1           5                       10

(2) INFORMATION FOR SEQ ID NO: 77:

(i) SEQUENCE CHARACTERISTICS:
(A) LENGTH: 5 amino acids
(B) TYPE: amino acid
(D) TOPOLOGY: linear (v) FRAGMENT TYPE: internal fragment (ix) FEATURE:
(D) OTHER INFORMATION: Xaa in any location 2 to 5 is an amino acid.

(xi) SEQUENCE DESCRIPTION: SEQ ID NO: 77:

Cys Xaa Xaa Xaa Xaa
1               5

(2) INFORMATION FOR SEQ ID NO: 78:

(i) SEQUENCE CHARACTERISTICS:
(A) LENGTH: 4 amino acids
(B) TYPE: amino acid
(D) TOPOLOGY: linear (v) FRAGMENT TYPE: internal fragment (ix) FEATURE:
(D) OTHER INFORMATION: Xaa in any location 2 to 4 is an amino acid.

(xi) SEQUENCE DESCRIPTION: SEQ ID NO: 78:

Cys Xaa Xaa Xaa
1

(2) INFORMATION FOR SEQ ID NO: 79:

(i) SEQUENCE CHARACTERISTICS:
(A) LENGTH: 6 amino acids
(B) TYPE: amino acid
(D) TOPOLOGY: linear (v) FRAGMENT TYPE: internal fragment (ix) FEATURE:
(D) OTHER INFORMATION: Xaa in any location 2 to 6 is an amino acid.

(xi) SEQUENCE DESCRIPTION: SEQ ID NO: 79:

Cys Xaa Xaa Xaa Xaa Xaa
1               5

(2) INFORMATION FOR SEQ ID NO: 80:

(i) SEQUENCE CHARACTERISTICS:
(A) LENGTH: 5 amino acids
(B) TYPE: amino acid
(D) TOPOLOGY: linear (v) FRAGMENT TYPE: internal fragment (ix) FEATURE:
(D) OTHER INFORMATION: Xaa in any location 2 to 5 is an amino acid.

( x i ) SEQUENCE DESCRIPTION: SEQ ID NO: 80:

Cys Xaa Xaa Xaa Xaa
1               5

( 2 ) INFORMATION FOR SEQ ID NO: 81:

( i ) SEQUENCE CHARACTERISTICS:
        ( A ) LENGTH: 4 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in any location 2 to 4 is
            an amino acid.

( x i ) SEQUENCE DESCRIPTION: SEQ ID NO: 81:

Cys Xaa Xaa Xaa
1

( 2 ) INFORMATION FOR SEQ ID NO: 82:

( i ) SEQUENCE CHARACTERISTICS:
        ( A ) LENGTH: 15 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in any location 2, or
            4 to 15 is an amino acid.

( x i ) SEQUENCE DESCRIPTION: SEQ ID NO: 82:

Cys Xaa Cys Xaa Xaa Xaa Xaa Xaa Xaa Xaa Xaa Xaa Xaa Xaa Xaa
1               5                   1 0                 1 5

( 2 ) INFORMATION FOR SEQ ID NO: 83:

( i ) SEQUENCE CHARACTERISTICS:
        ( A ) LENGTH: 14 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in any location 2, or
            4 to 14 is an amino acid.

( x i ) SEQUENCE DESCRIPTION: SEQ ID NO: 83:

Cys Xaa Cys Xaa Xaa Xaa Xaa Xaa Xaa Xaa Xaa Xaa Xaa Xaa
1               5                   1 0

( 2 ) INFORMATION FOR SEQ ID NO: 84:

( i ) SEQUENCE CHARACTERISTICS:
        ( A ) LENGTH: 13 amino acids
        ( B ) TYPE: amino acid
        ( D ) TOPOLOGY: linear ( v ) FRAGMENT TYPE: internal fragment ( i x ) FEATURE:
        ( D ) OTHER INFORMATION: Xaa in any location 2, or
            4 to 13 is an amino acid.

( x i ) SEQUENCE DESCRIPTION: SEQ ID NO: 84:

```
Cys  Xaa  Cys  Xaa  Xaa  Xaa  Xaa  Xaa  Xaa  Xaa  Xaa  Xaa  Xaa
 1             5                             1 0
```

(2) INFORMATION FOR SEQ ID NO: 85:

(i) SEQUENCE CHARACTERISTICS:
        (A) LENGTH: 8 amino acids
        (B) TYPE: amino acid
        (D) TOPOLOGY: linear (v) FRAGMENT TYPE: internal fragment (ix) FEATURE:
        (D) OTHER INFORMATION: Xaa in any location 2 to 7
        is an amino acid.

(xi) SEQUENCE DESCRIPTION: SEQ ID NO: 85:

```
Cys  Xaa  Xaa  Xaa  Xaa  Xaa  Xaa  Cys
 1                  5
```

(2) INFORMATION FOR SEQ ID NO: 86:

(i) SEQUENCE CHARACTERISTICS:
        (A) LENGTH: 7 amino acids
        (B) TYPE: amino acid
        (D) TOPOLOGY: linear (v) FRAGMENT TYPE: internal fragment (ix) FEATURE:
        (D) OTHER INFORMATION: Xaa in any location 2 to 6
        is an amino acid.

(xi) SEQUENCE DESCRIPTION: SEQ ID NO: 86:

```
Cys  Xaa  Xaa  Xaa  Xaa  Xaa  Cys
 1                  5
```